United States Patent
Crespo-Hernandez et al.

(10) Patent No.: US 10,864,273 B2
(45) Date of Patent: *Dec. 15, 2020

(54) THIOBASE COMPOUNDS FOR PHOTODYNAMIC THERAPY

(71) Applicant: CASE WESTERN RESERVE UNIVERSITY, Cleveland, OH (US)

(72) Inventors: Carlos E. Crespo-Hernandez, Cleveland, OH (US); Marvin Pollum, Cleveland, OH (US)

(73) Assignee: CASE WESTERN RESERVE UNIVERSITY, Cleveland, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/573,682

(22) Filed: Sep. 17, 2019

(65) Prior Publication Data

US 2020/0009249 A1   Jan. 9, 2020

Related U.S. Application Data

(63) Continuation of application No. 15/003,225, filed on Jan. 21, 2016, now Pat. No. 10,413,608.

(60) Provisional application No. 62/105,949, filed on Jan. 21, 2015.

(51) Int. Cl.
*A61K 41/00* (2020.01)
*A61N 5/06* (2006.01)

(52) U.S. Cl.
CPC .......... *A61K 41/0057* (2013.01); *A61N 5/062* (2013.01); *A61N 2005/0659* (2013.01); *A61N 2005/0661* (2013.01); *A61N 2005/0662* (2013.01)

(58) Field of Classification Search
None
See application file for complete search history.

(56) References Cited

PUBLICATIONS

Detty et al., "Current Clinical and Preclinical Photosensitizers for Use in Photodynamic Therapy", 2004, Journal of Medicinal Chemistry, vol. 4 7, No. 16, pp. 3897-3915.

*Primary Examiner* — Kortney L. Klinkel
*Assistant Examiner* — Tori Strong
(74) *Attorney, Agent, or Firm* — Tarolli, Sundheim, Covell & Tummino LLP

(57) ABSTRACT

A method of using a compound in a phototherapy procedure includes administering to a subject in need of treatment a therapeutically effective amount of a thio-substituted nucleobase, nucleoside, nucleotide, and/or analogs thereof; and exposing the administered compound to electromagnetic radiation.

17 Claims, 9 Drawing Sheets

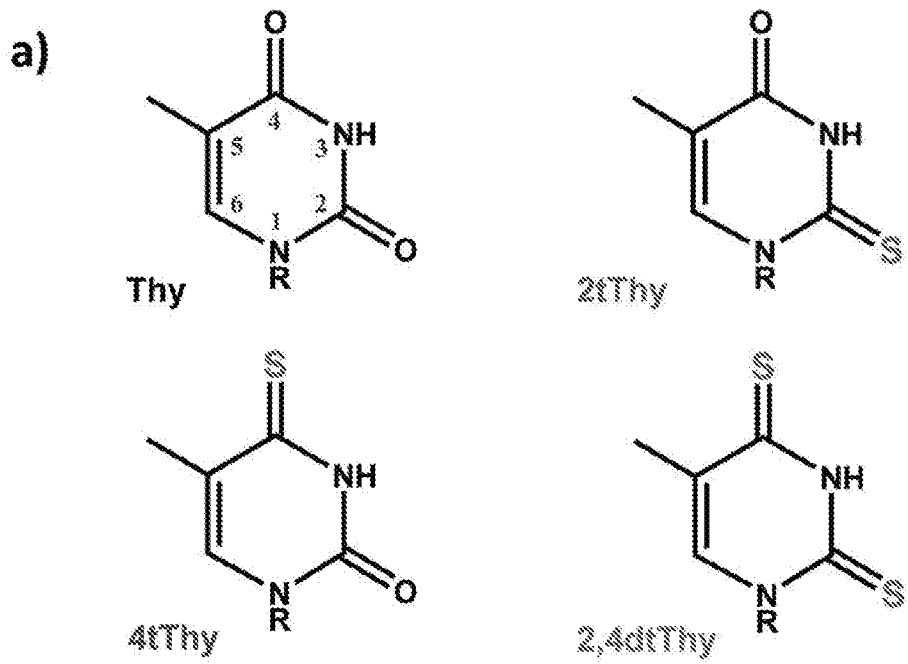
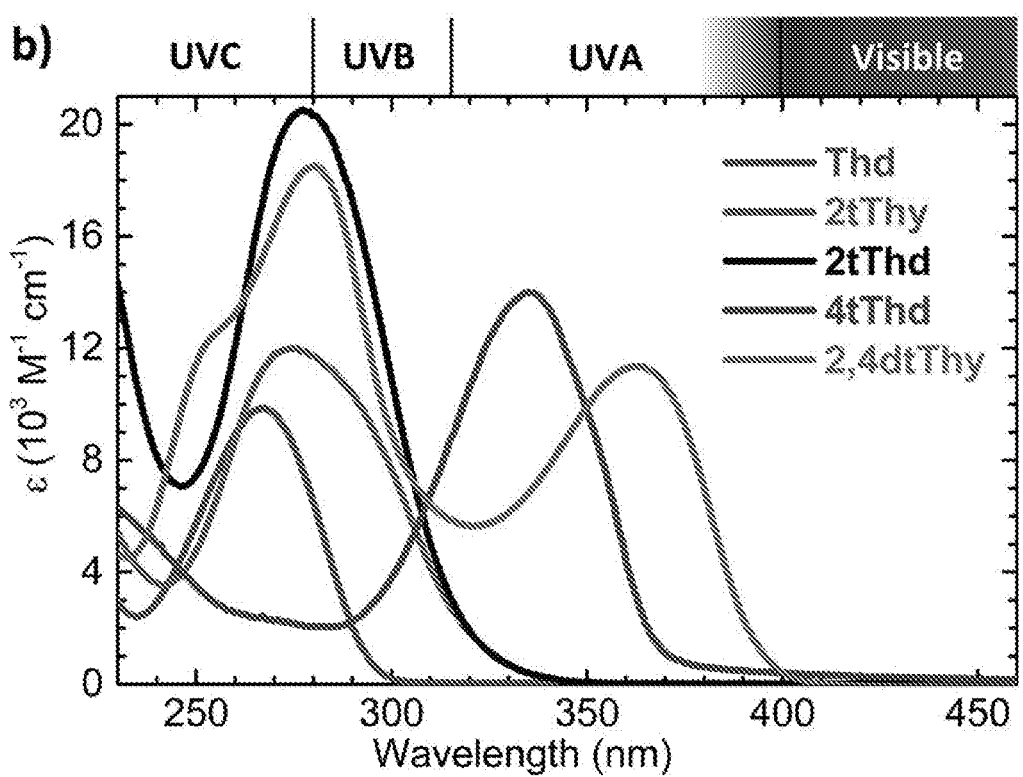
Figs. 1A-B

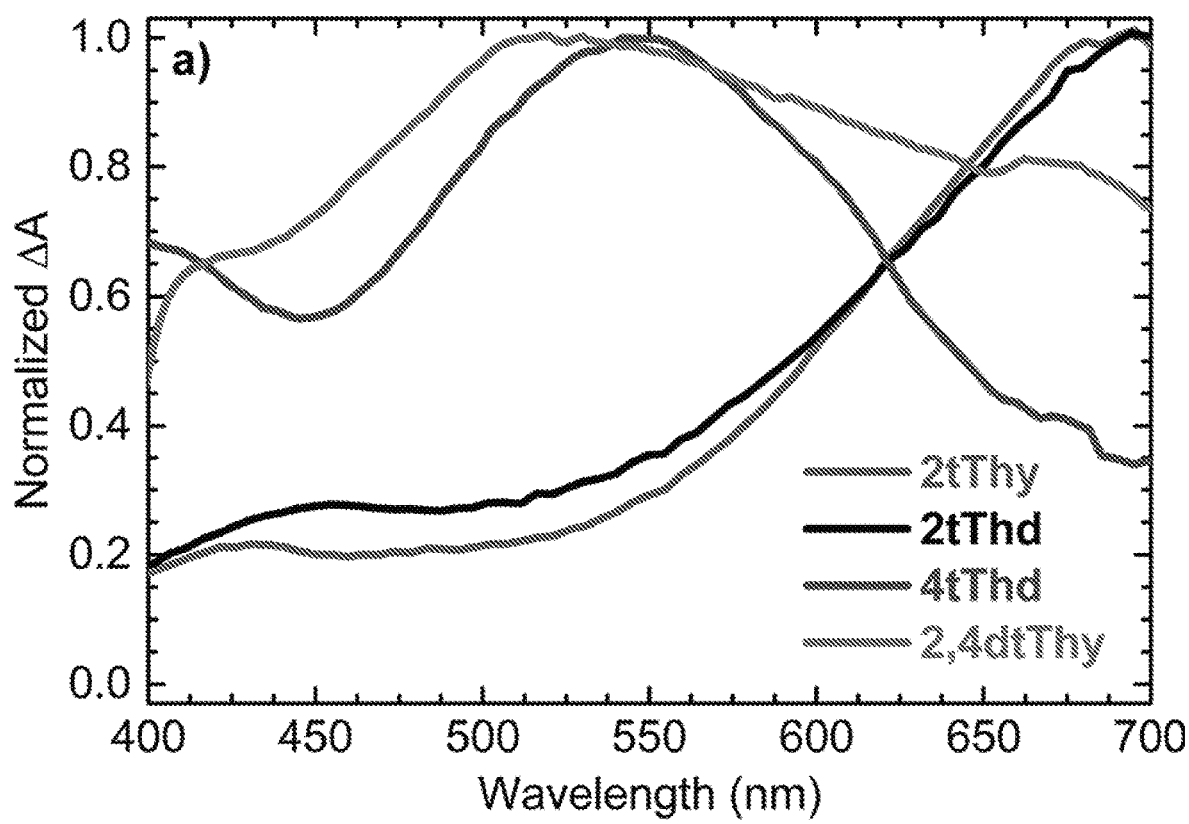
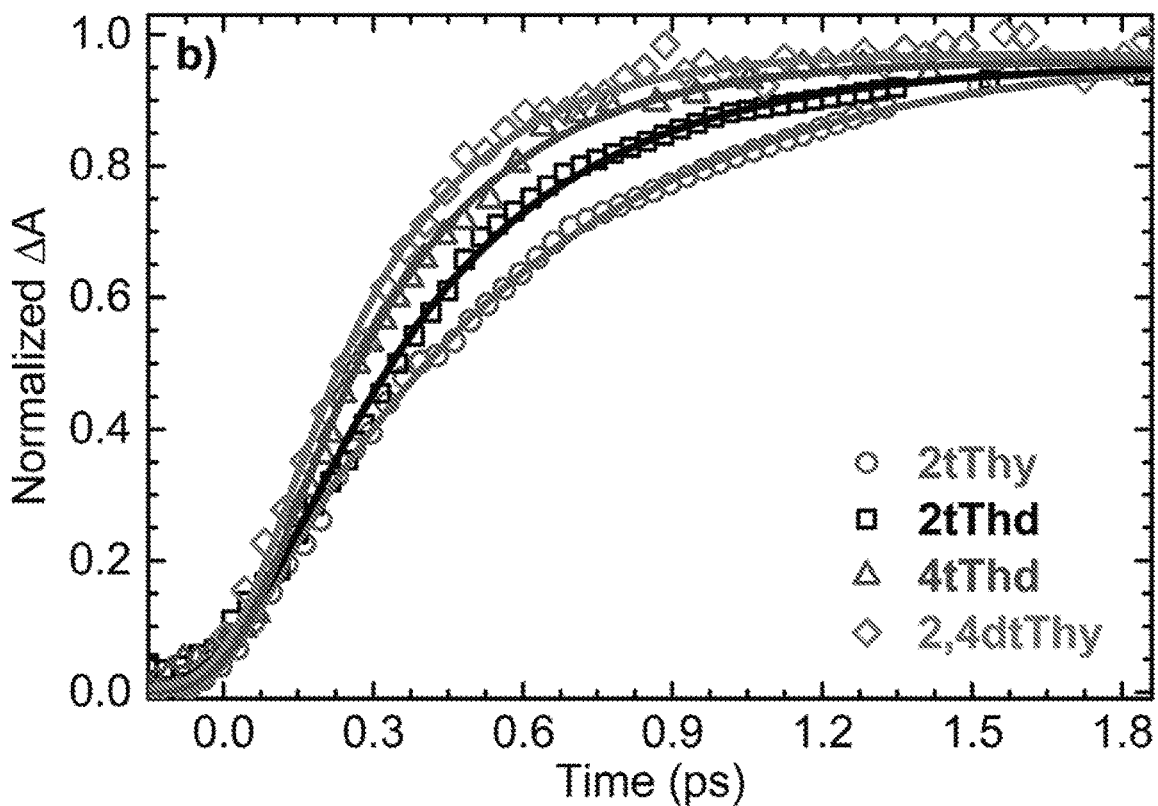
Figs. 2A-B

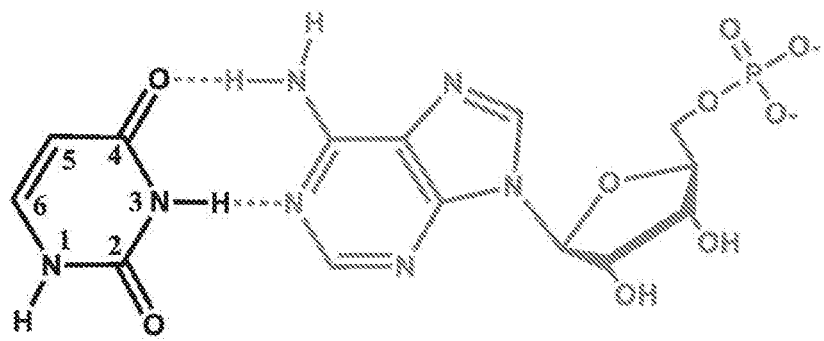
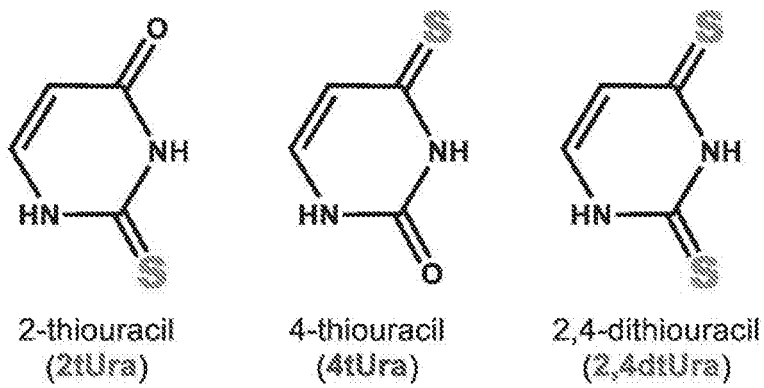
Fig. 6
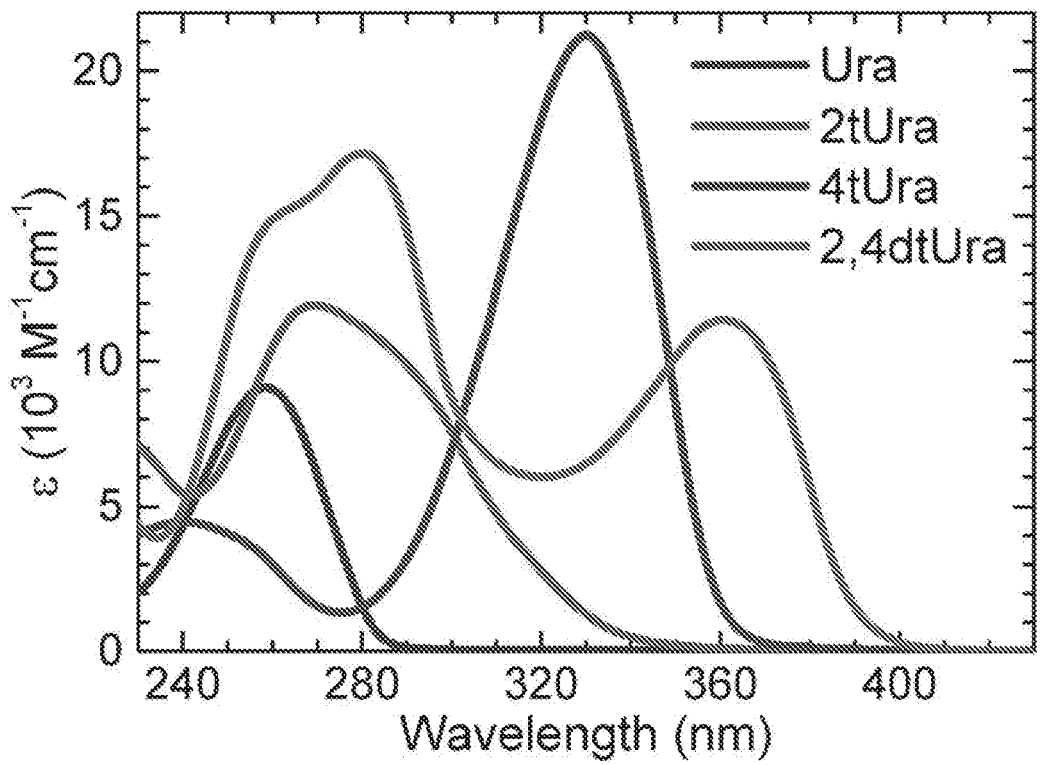
Fig. 7

THIOBASE COMPOUNDS FOR PHOTODYNAMIC THERAPY

RELATED APPLICATION

This application claims priority from U.S. Provisional Application No. 62/105,949, filed Jan. 21, 2015, the subject matter of which is incorporated herein by reference in its entirety.

GOVERNMENT FUNDING

This invention was made with government support under Grant No. CHE-1255084 awarded by The National Science Foundation. The United States government has certain rights to the invention.

BACKGROUND

Photodynamic therapy (PDT) is a therapy employed routinely in the treatment of superficial dermatological malignancies and is under investigation for a range of additional tumor types. Most applications of PDT involve the use of an active compound, known as a photosensitizer, and a light source, the wavelength of which can be chosen to be appropriate for exciting the photosensitizer.

Photochemical reactions initiated by excited photosensitizers are crucial to their efficacy because these reactions are what lead to apoptosis, or cell death, following light activation. Photosensitizers can initiate these reactions primarily in two ways. Following the absorption of light energy, the excited photosensitizer can either directly react with a biomolecule (Type I photosensitization) or it can transfer its energy to molecular oxygen. Energy transfer to molecular oxygen forms highly reactive oxygen species, such as singlet oxygen, which can then go on to damage biomolecules (Type II photosensitization). This leads to the destruction of any tissues which have either selectively taken up the photosensitizer or have been locally exposed to light.

For example, a PDT treatment of human skin cancer may involve the following steps. First, a photosensitizer is administered to the patient. The photosensitizer is taken up by the cells. The area to be treated is then exposed to light of the appropriate wavelength. The photosensitizer can absorb light and reacts with nearby tissue oxygen, resulting in reactive oxygen species. These reactive oxygen species react with biomolecules, fatally damaging some of the cells in the treatment area.

PDT has been used in the treatment of dermatological tumors where light can be readily applied to the surface of the skin; clinically substantial subsets of skin tumors are difficult to treat by conventional therapies (because of size, site or multiple lesions presentation). In the treatment of skin conditions, the photosensitizer or photosensitizer precursor can be applied topically, and locally excited by a light source. In the local treatment of internal cancer cells, on the other hand, photosensitizers or photosensitizer precursors can for example be administered intravenously and light can be delivered to the target area using endoscopes and fiber optic catheters. Compared to normal healthy tissues, most types of cancer cells are especially active in both the uptake and accumulation of photosensitizers, which makes cancer cells especially vulnerable to PDT, since having more photosensitizer present in a cell leads to more damage to that cell during PDT.

SUMMARY

Embodiments described herein relate to compounds comprising thio-substituted nucleobases, nucleosides, nucleotides, and/or analogs thereof for use in photodynamic therapy or phototherapy procedures, and particularly relate to the use of dithio-substituted pyrimidine and purine nucleobases, nucleosides, nucleotides, and/or analogs thereof for use in phototherapy procedures.

In some embodiments, a method of using a compound in a phototherapy procedure can include administering to a subject in need of treatment a therapeutically effective amount of a compound having the formula:

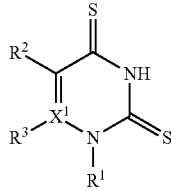

wherein $X^1$ is C or N, $R^1$ is H, OH, ribose, deoxyribose, amino acid residue(s), fatty acid residue(s), $OR_a$, where $R_a$ comprises at least one of a straight chain, branched or cyclic alkyl, CO-alkyl, CO-aryl, CO-alkoxyalkyl, arylsulfonyl, or aralkylsulfonyl, or a mono, di, or triphosphate thereof, $R^2$ and $R^3$ are the same or different and are independently selected from the group consisting of hydrogen, substituted or unsubstituted $C_1$-$C_{24}$ alkyl, $C_2$-$C_{24}$ alkenyl, $C_2$-$C_{24}$ alkynyl, $C_3$-$C_{20}$ aryl, heteroaryl, heterocycloalkenyl containing from 5-6 ring atoms (wherein from 1-3 of the ring atoms is independently selected from N, NH, N($C_1$-$C_6$ alkyl), NC(O) ($C_1$-$C_6$ alkyl), O, and S), $C_6$-$C_{24}$ alkaryl, $C_6$-$C_{24}$ aralkyl, halo, —Si($C_1$-$C_3$ alkyl)$_3$, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl (including $C_2$-$C_{24}$ alkylcarbonyl (—CO-alkyl) and $C_6$-$C_{20}$ arylcarbonyl (—CO-aryl)), acyloxy (—O-acyl), $C_2$-$C_{24}$ alkoxycarbonyl (—(CO)—O-alkyl), $C_6$-$C_{20}$ aryloxycarbonyl (—(CO)—O-aryl), $C_2$-$C_{24}$ alkylcarbonato (—O—(CO)—O-alkyl), $C_6$-$C_{20}$ arylcarbonato (—O—(CO)—O-aryl), carboxy (—COOH), carboxylato (—COO$^-$), carbamoyl (—(CO)—NH$_2$), $C_1$-$C_{24}$ alkyl-carbamoyl (—(CO)—NH($C_1$-$C_{24}$ alkyl)), arylcarbamoyl (—(CO)—NH-aryl), thiocarbamoyl (—(CS)—NH$_2$), carbamido (—NH—(CO)—NH$_2$), cyano (—CN), isocyano (—N$^+$C$^-$), cyanato (—O—CN), isocyanato (—O—N$^+$=C$^-$), isothiocyanato (—S—CN), azido (—N=N$^+$=N$^-$), formyl (—(CO)—H), thioformyl (—(CS)—H), amino (—NH$_2$), $C_1$-$C_{24}$ alkyl amino, $C_5$-$C_{20}$ aryl amino, $C_2$-$C_{24}$ alkylamido (—NH—(CO)-alkyl), $C_6$-$C_{20}$ arylamido (—NH—(CO)-aryl), imino (—CR=NH where R is hydrogen, $C_1$-$C_{24}$ alkyl, $C_5$-$C_{20}$ aryl, $C_6$-$C_{24}$ alkaryl, $C_6$-$C_{24}$ aralkyl, etc.), alkylimino (—CR=N(alkyl), where R=hydrogen, alkyl, aryl, alkaryl, aralkyl, etc.), arylimino (—CR=N (aryl), where R=hydrogen, alkyl, aryl, alkaryl, etc.), nitro (—NO$_2$), nitroso (—NO), sulfo (—SO$_2$—OH), sulfonato (—SO$_2$—O$^-$), $C_1$-$C_{24}$ alkylsulfanyl (—S-alkyl; also termed "alkylthio"), arylsulfonyl (—S-aryl; also termed "arylthio"), $C_1$-$C_{24}$ alkylsulfinyl (—(SO)-alkyl), $C_5$-$C_{20}$ arylsulfinyl (—(SO)-aryl), $C_1$-$C_{24}$ alkylsulfonyl (—SO$_2$-alkyl), $C_5$-$C_{20}$ arylsulfonyl (—SO$_2$-aryl), phosphono (—P(O)(OH)$_2$), phosphonato (—P(O)(O$^-$)$_2$), phosphinato (—P(O)(O$^-$)), phospho (—PO$_2$), phosphino (—PH$_2$), and combinations thereof, and wherein $R^2$ and $R^3$ may be linked to form a cyclic or polycyclic ring, wherein the ring is a substituted or unsubstituted aryl, a substituted or unsubstituted heteroaryl, a substituted or unsubstituted cycloalkyl, and a substituted or unsubstituted heterocyclyl, and pharmaceutically acceptable salts thereof. The compound administered to the subject can then be exposed to electromagnetic radiation.

In some embodiments, $R^2$ and $R^3$ are the same or different and are independently selected from the group consisting of a H, F, Cl, Br, I, a lower alkyl group, $(CH_2)_{n1}OR'$ (wherein n1=1, 2, or 3), $CF_3$, $CH_2$—$CH_2X$, O—$CH_2$—$CH_2X$, $CH_2$—$CH_2$—$CH_2X$, O—$CH_2$—$CH_2$—$CH_2X$ (wherein X=F, Cl, Br, or I), CN, (C=O)—R', $N(R')_2$, $NO_2$, (C=O)$N(R')_2$, O(CO)R', OR', SR', COOR' (wherein R' is H or a lower alkyl group); substituted or unsubstituted aryl, heteroaryl, cycloalkyl, or heterocyclyl, and wherein $R^2$ and $R^3$ may be linked to form a cyclic or polycyclic ring, wherein the ring is a substituted or unsubstituted aryl, a substituted or unsubstituted heteroaryl, a substituted or unsubstituted cycloalkyl, and a substituted or unsubstituted heterocyclyl, and pharmaceutically acceptable salts thereof.

In other embodiments, the compound is selected from the group consisting of:

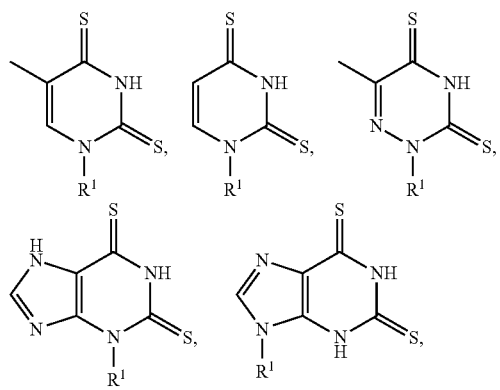

wherein $R^1$ is H, OH, ribose, deoxyribose, amino acid residue(s), fatty acid residue(s), $OR_a$, where $R_a$ comprises at least one of a straight chain, branched or cyclic alkyl, CO-alkyl, CO-aryl, CO-alkoxyalkyl, arylsulfonyl, or aralkylsulfonyl, or a mono, di, or triphosphate thereof, and pharmaceutically acceptable salts thereof.

In still other embodiments, the compound has the formula:

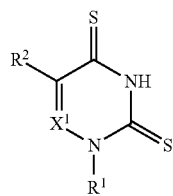

wherein $X^1$ is C or N, $R^1$ is H, OH, ribose, deoxyribose, amino acid residue(s), fatty acid residue(s), $OR_a$, where $R_a$ comprises at least one of a straight chain, branched or cyclic alkyl, CO-alkyl, CO-aryl, CO-alkoxyalkyl, arylsulfonyl, or aralkylsulfonyl, or a mono, di, or triphosphate thereof, $R^2$ is selected from the group consisting of a H, F, Cl, Br, I, a lower alkyl group, $(CH_2)_{n1}OR'$ (wherein n1=1, 2, or 3), $CF_3$, $CH_2$—$CH_2X$, O—$CH_2$—$CH_2X$, $CH_2$—$CH_2$—$CH_2X$, O—$CH_2$—$CH_2$—$CH_2X$ (wherein X=F, Cl, Br, or I), CN, (C=O)—R', $N(R')_2$, $NO_2$, (C=O)$N(R')_2$, O(CO)R', OR', SR', COOR' (wherein R' is H or a lower alkyl group); substituted or unsubstituted aryl, heteroaryl, cycloalkyl, or heterocyclyl, and pharmaceutically acceptable salts thereof.

In some embodiments, the compound absorbs electromagnetic radiation having wavelengths from about 300 nm to about 1400 nm and upon absorption of the electromagnetic radiation can cause localized cell death and injury. For example, the compound can be exposed to ultraviolet radiation to cause localized cell death or injury. In some embodiments, exposure of the administered compound to electromagnetic radiation can generate a therapeutically effective amount or reactive intermediates that can cause localized cell death or injury.

The compounds can be administered to a target tissue of the subject by local or systemic administration, such as topical, parenteral, and/or intravenous delivery. The target tissue can include, for example, colon, prostate, gastric, esophageal, uterine, endometrial, pancreatic, breast, cervical, brain, skin, gallbladder, lung, throat, kidney, testicular, prostate, gastric, or ovary tissue. The target tissue can be normal, diseased, inflamed, or neoplastic tissue, such as cancerous tissue or a tumor.

In other embodiments the phototherapy procedure can be used in the treatment of cancer or a cancer-associated disorder. The cancer or cancer-associated disorder can be, for example, colon cancer, prostate cancer, gastric cancer, esophageal cancer, uterine cancer, endometrial cancer, pancreatic cancer, breast cancer, cervical cancer, brain cancer, skin cancer, gall bladder cancer, lung cancer, or ovarian cancer. Alternatively, the phototherapy procedure can be used to treat an inflammation-associated disorder, such as psoriasis.

BRIEF DESCRIPTION OF THE DRAWINGS

FIGS. 1(A-B) illustrate (A) Structures and common ring numbering of thymine (Thy, R=H) and thymidine (Thd, R=2-deoxyribose) along with their sulfur-substituted analogues: 2-thiothymine (2tThy), 4-thiothy-mine (4tThy), and 2,4-dithiothymine (2,4dtThy), where R=H, and 2-thiothymidine (2tThd), 4-thiothymidine (4tThd), and 2,4-dithiothymidine (2,4dtThd), where R=2-deoxyribose. (B) Absorption spectra of the thymine series in phosphate buffer solution at pH 7.4.

FIGS. 2(A-B) (A) illustrate normalized absorption spectra of the lowest-energy triplet states and (B) representative growth traces of triplet-state population for 2tThy ($\lambda_{exc.}$=320 nm), 2tThd ($\lambda_{exc.}$=320 nm), 4tThd ($\lambda_{exc.}$=320 nm), and 2,4dtThy ($\lambda_{exc}$=335 or 360 nm) at 600 nm probe wavelength in pH 7.4 phosphate buffer solution. Traces are cropped at ~2 ps and normalized to show the relative rates of intersystem crossing.

FIG. 6 illustrates structures and common ring numbering of the canonical RNA-base uracil and its three thionated derivatives.

FIG. 7 illustrates a plot showing molar absorptivity spectra of the canonical uracil nucleobase and the thiouracil series studied in aqueous phosphate-buffered saline solution, pH 7.4.

DETAILED DESCRIPTION

Figure 3:
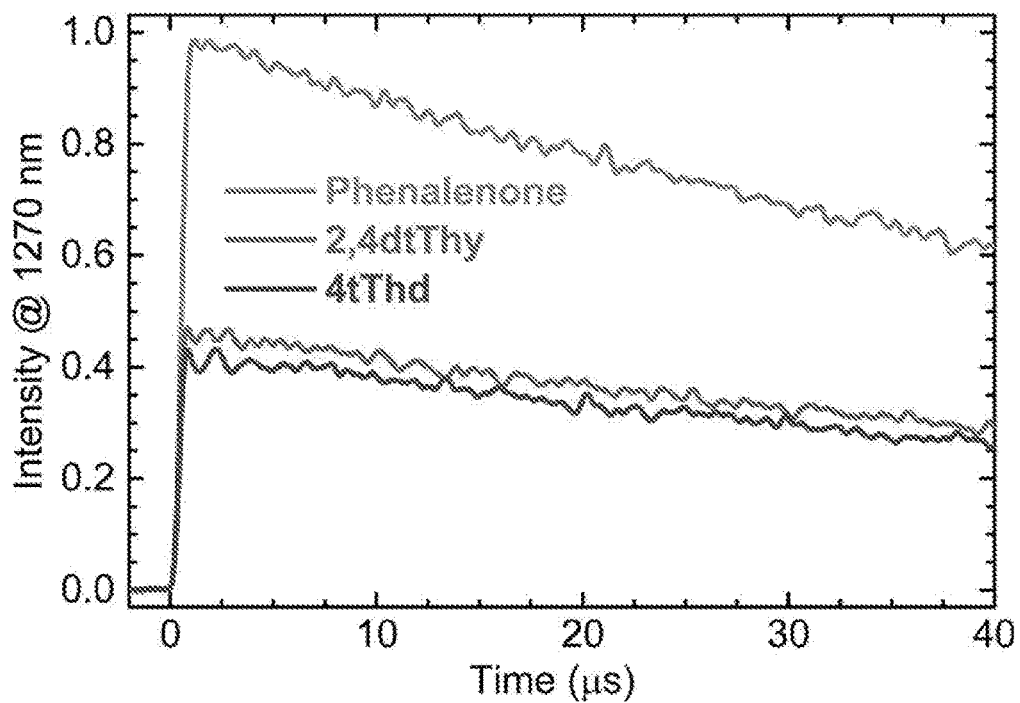
FIG. 3 illustrates a plot showing singlet oxygen phosphorescence decay traces monitored at 1270 nm and generated y pulsed photoexcitation (335 nm, 7 ns pulse length) of 2,4dtThy, 4tThd, and phenalenone in $O_2$-saturated acetonitrile solutions.

For convenience, certain terms employed in the specification, examples, and appended claims are collected here. Unless defined otherwise, all technical and scientific terms used herein have the same meaning as commonly understood by one of ordinary skill in the art to which this application belongs.

The articles "a" and "an" are used herein to refer to one or to more than one (i.e., to at least one) of the grammatical object of the article. By way of example, "an element" means one element or more than one element.

The terms "comprise," "comprising," "include," "including," "have," and "having" are used in the inclusive, open sense, meaning that additional elements may be included. The terms "such as", "e.g.", as used herein are non-limiting and are for illustrative purposes only. "Including" and "including but not limited to" are used interchangeably.

The term "or" as used herein should be understood to mean "and/or", unless the context clearly indicates otherwise.

As used herein, the term "about" or "approximately" refers to a quantity, level, value, number, frequency, percentage, dimension, size, amount, weight or length that varies by as much as 15%, 10%, 9%, 8%, 7%, 6%, 5%, 4%, 3%, 2% or 1% to a reference quantity, level, value, number, frequency, percentage, dimension, size, amount, weight or length. In one embodiment, the term "about" or "approximately" refers a range of quantity, level, value, number, frequency, percentage, dimension, size, amount, weight or length ±15%, ±10%, ±9%, ±8%, ±7%, ±6%, ±5%, ±4%, ±3%, ±2%, or ±1% about a reference quantity, level, value, number, frequency, percentage, dimension, size, amount, weight or length.

It will be noted that the structure of some of the compounds of the application include asymmetric (chiral) carbon or sulfur atoms. It is to be understood accordingly that the isomers arising from such asymmetry are included herein, unless indicated otherwise. Such isomers can be obtained in substantially pure form by classical separation techniques and by stereochemically controlled synthesis. The compounds of this application may exist in stereoisomeric form, therefore can be produced as individual stereoisomers or as mixtures.

The term "isomerism" means compounds that have identical molecular formulae but that differ in the nature or the sequence of bonding of their atoms or in the arrangement of their atoms in space. Isomers that differ in the arrangement of their atoms in space are termed "stereoisomers". Stereoisomers that are not mirror images of one another are termed "diastereoisomers", and stereoisomers that are non-superimposable mirror images are termed "enantiomers", or sometimes optical isomers. A carbon atom bonded to four nonidentical substituents is termed a "chiral center" whereas a sulfur bound to three or four different substitutents, e.g., sulfoxides or sulfinimides, is likewise termed a "chiral center".

The term "chiral isomer" means a compound with at least one chiral center. It has two enantiomeric forms of opposite chirality and may exist either as an individual enantiomer or as a mixture of enantiomers. A mixture containing equal amounts of individual enantiomeric forms of opposite chirality is termed a "racemic mixture". A compound that has more than one chiral center has 2n−1 enantiomeric pairs, where n is the number of chiral centers. Compounds with more than one chiral center may exist as either an individual diastereomer or as a mixture of diastereomers, termed a "diastereomeric mixture". When one chiral center is present, a stereoisomer may be characterized by the absolute configuration (R or S) of that chiral center. Alternatively, when one or more chiral centers are present, a stereoisomer may be characterized as (+) or (−). Absolute configuration refers to the arrangement in space of the substituents attached to the chiral center. The substituents attached to the chiral center under consideration are ranked in accordance with the Sequence Rule of Cahn, Ingold and Prelog. (Cahn et al, Angew. Chem. Inter. Edit. 1966, 5, 385; errata 511; Cahn et al., Angew. Chem. 1966, 78, 413; Cahn and Ingold, J Chem. Soc. 1951 (London), 612; Cahn et al., Experientia 1956, 12, 81; Cahn, J., Chem. Educ. 1964, 41, 116).

The term "geometric Isomers" means the diastereomers that owe their existence to hindered rotation about double bonds. These configurations are differentiated in their names by the prefixes cis and trans, or Z and E, which indicate that the groups are on the same or opposite side of the double bond in the molecule according to the Cahn-Ingold-Prelog rules. Further, the structures and other compounds discussed in this application include all atropic isomers thereof.

The term "atropic isomers" are a type of stereoisomer in which the atoms of two isomers are arranged differently in space. Atropic isomers owe their existence to a restricted rotation caused by hindrance of rotation of large groups about a central bond. Such atropic isomers typically exist as a mixture, however as a result of recent advances in chromatography techniques, it has been possible to separate mixtures of two atropic isomers in select cases.

The terms "crystal polymorphs" or "polymorphs" or "crystal forms" means crystal structures in which a compound (or salt or solvate thereof) can crystallize in different crystal packing arrangements, all of which have the same elemental composition. Different crystal forms usually have different X-ray diffraction patterns, infrared spectral, melting points, density hardness, crystal shape, optical and electrical properties, stability and solubility. Recrystallization solvent, rate of crystallization, storage temperature, and other factors may cause one crystal form to dominate. Crystal polymorphs of the compounds can be prepared by crystallization under different conditions.

The term "derivative" refers to compounds that have a common core structure, and are substituted with various groups as described herein.

The phrases "parenteral administration" and "administered parenterally" are art-recognized terms, and include modes of administration other than enteral and topical administration, such as injections, and include, without limitation, intravenous, intramuscular, intrapleural, intravascular, intrapericardial, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrastemal injection and infusion.

The term "treating" is art-recognized and includes inhibiting a disease, disorder or condition in a subject, e.g., impeding its progress; and relieving the disease, disorder or condition, e.g., causing regression of the disease, disorder and/or condition. Treating the disease or condition includes ameliorating at least one symptom of the particular disease or condition, even if the underlying pathophysiology is not affected.

The term "preventing" is art-recognized and includes stopping a disease, disorder or condition from occurring in a subject, which may be predisposed to the disease, disorder and/or condition but has not yet been diagnosed as having it. Preventing a condition related to a disease includes stopping the condition from occurring after the disease has been diagnosed but before the condition has been diagnosed.

The term "pharmaceutical composition" refers to a formulation containing the disclosed compounds in a form suitable for administration to a subject. In a preferred embodiment, the pharmaceutical composition is in bulk or in unit dosage form. The unit dosage form is any of a variety of forms, including, for example, a capsule, an IV bag, a tablet, a single pump on an aerosol inhaler, or a vial. The quantity of active ingredient (e.g., a formulation of the disclosed compound or salts thereof) in a unit dose of composition is an effective amount and is varied according to the particular treatment involved. One skilled in the art will appreciate that it is sometimes necessary to make routine variations to the dosage depending on the age and condition of the patient. The dosage will also depend on the route of administration. A variety of routes are contemplated, including oral, pulmonary, rectal, parenteral, transdermal, subcutaneous, intravenous, intramuscular, intraperitoneal, intranasal, inhalational, and the like. Dosage forms for the topical or transdermal administration of a compound described herein includes powders, sprays, ointments, pastes, creams, lotions, gels, solutions, patches, nebulized compounds, and inhalants. In a preferred embodiment, the active compound is mixed under sterile conditions with a pharmaceutically acceptable carrier, and with any preservatives, buffers, or propellants that are required.

The phrase "pharmaceutically acceptable" is art-recognized. In certain embodiments, the term includes compositions, polymers and other materials and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" is art-recognized, and includes, for example, pharmaceutically acceptable materials, compositions or vehicles, such as a liquid or solid filler, diluent, excipient, solvent or encapsulating material, involved in carrying or transporting any subject composition from one organ, or portion of the body, to another organ, or portion of the body. Each carrier must be "acceptable" in the sense of being compatible with the other ingredients of a subject composition and not injurious to the patient. In certain embodiments, a pharmaceutically acceptable carrier is non-pyrogenic. Some examples of materials which may serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, sunflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The compounds of the application are capable of further forming salts. All of these forms are also contemplated herein.

"Pharmaceutically acceptable salt" of a compound means a salt that is pharmaceutically acceptable and that possesses the desired pharmacological activity of the parent compound. For example, the salt can be an acid addition salt. One embodiment of an acid addition salt is a hydrochloride salt. The pharmaceutically acceptable salts can be synthesized from a parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile being preferred. Lists of salts are found in Remington's Pharmaceutical Sciences, 18th ed. (Mack Publishing Company, 1990).

The compounds described herein can also be prepared as esters, for example pharmaceutically acceptable esters. For example, a carboxylic acid function group in a compound can be converted to its corresponding ester, e.g., a methyl, ethyl, or other ester. Also, an alcohol group in a compound can be converted to its corresponding ester, e.g., an acetate, propionate, or other ester.

The compounds described herein can also be prepared as prodrugs, for example pharmaceutically acceptable prodrugs. The terms "pro-drug" and "prodrug" are used interchangeably herein and refer to any compound, which releases an active parent drug in vivo. Since prodrugs are known to enhance numerous desirable qualities of pharmaceuticals (e.g., solubility, bioavailability, manufacturing, etc.) the compounds can be delivered in prodrug form. Thus, the compounds described herein are intended to cover prodrugs of the presently claimed compounds, methods of delivering the same and compositions containing the same. "Prodrugs" are intended to include any covalently bonded carriers that release an active parent drug in vivo when such prodrug is administered to a subject. Prodrugs are prepared by modifying functional groups present in the compound in such a way that the modifications are cleaved, either in routine manipulation or in vivo, to the parent compound. Prodrugs include compounds wherein a hydroxy, amino, sulfhydryl, carboxy, or carbonyl group is bonded to any group that may be cleaved in vivo to form a free hydroxyl, free amino, free sulfhydryl, free carboxy or free carbonyl group, respectively. Prodrugs can also include a precursor (forerunner) of a compound described herein that undergoes chemical conversion by metabolic processes before becoming an active or more active pharmacological agent or active compound described herein.

Examples of prodrugs include, but are not limited to, esters (e.g., acetate, dialkylaminoacetates, formates, phosphates, sulfates, and benzoate derivatives) and carbamates (e.g., N,N-dimethylaminocarbonyl) of hydroxy functional groups, ester groups (e.g., ethyl esters, morpholinoethanol esters) of carboxyl functional groups, N-acyl derivatives (e.g., N-acetyl)N-Mannich bases, Schiff bases and enaminones of amino functional groups, oximes, acetals, ketals and enol esters of ketone and aldehyde functional groups in compounds, and the like, as well as sulfides that are oxidized to form sulfoxides or sulfones.

The term "protecting group" refers to a grouping of atoms that when attached to a reactive group in a molecule masks, reduces or prevents that reactivity. Examples of protecting groups can be found in Green and Wuts, Protective Groups in Organic Chemistry, (Wiley, 2.sup.nd ed. 1991); Harrison and Harrison et al., Compendium of Synthetic Organic Methods, Vols. 1-8 (John Wiley and Sons, 1971-1996); and Kocienski, Protecting Groups, (Verlag, 3$^{rd}$ ed. 2003).

The term "amine protecting group" is intended to mean a functional group that converts an amine, amide, or other nitrogen-containing moiety into a different chemical group that is substantially inert to the conditions of a particular chemical reaction. Amine protecting groups are preferably removed easily and selectively in good yield under conditions that do not affect other functional groups of the molecule. Examples of amine protecting groups include, but are not limited to, formyl, acetyl, benzyl, t-butyldimethylsilyl, t-butyldiphenylsilyl, t-butyloxycarbonyl (Boc), p-methoxybenzyl, methoxymethyl, tosyl, trifluoroacetyl, trimethylsilyl (TMS), fluorenyl-methyloxycarbonyl, 2-trimethylsilyl-ethyoxycarbonyl, 1-methyl-1-(4-biphenylyl) ethoxycarbonyl, allyloxycarbonyl, benzyloxycarbonyl (CBZ), 2-trimethylsilyl-ethanesulfonyl (SES), trityl and substituted trityl groups, 9-fluorenylmethyloxycarbonyl (FMOC), nitro-veratryloxycarbonyl (NVOC), and the like. Those of skill in the art can identify other suitable amine protecting groups.

Representative hydroxy protecting groups include those where the hydroxy group is either acylated or alkylated such as benzyl, and trityl ethers as well as alkyl ethers, tetrahydropyranyl ethers, trialkylsilyl ethers and allyl ethers.

Additionally, the salts of the compounds described herein, can exist in either hydrated or unhydrated (the anhydrous) form or as solvates with other solvent molecules. Nonlimiting examples of hydrates include monohydrates, dihydrates, etc. Nonlimiting examples of solvates include ethanol solvates, acetone solvates, etc.

The term "solvates" means solvent addition forms that contain either stoichiometric or non stoichiometric amounts of solvent. Some compounds have a tendency to trap a fixed molar ratio of solvent molecules in the crystalline solid state, thus forming a solvate. If the solvent is water the solvate formed is a hydrate, when the solvent is alcohol, the solvate formed is an alcoholate. Hydrates are formed by the combination of one or more molecules of water with one of the substances in which the water retains its molecular state as $H_2O$, such combination being able to form one or more hydrate.

The compounds, salts and prodrugs described herein can exist in several tautomeric forms, including the enol and imine form, and the keto and enamine form and geometric isomers and mixtures thereof. Tautomers exist as mixtures of a tautomeric set in solution. In solid form, usually one tautomer predominates. Even though one tautomer may be described, the present application includes all tautomers of the present compounds. A tautomer is one of two or more structural isomers that exist in equilibrium and are readily converted from one isomeric form to another. This reaction results in the formal migration of a hydrogen atom accompanied by a switch of adjacent conjugated double bonds. In solutions where tautomerization is possible, a chemical equilibrium of the tautomers will be reached. The exact ratio of the tautomers depends on several factors, including temperature, solvent, and pH. The concept of tautomers that are interconvertable by tautomerizations is called tautomerism.

Of the various types of tautomerism that are possible, two are commonly observed. In keto-enol tautomerism a simultaneous shift of electrons and a hydrogen atom occurs.

Tautomerizations can be catalyzed by: Base: 1. deprotonation; 2. formation of a delocalized anion (e.g., an enolate); 3. protonation at a different position of the anion; Acid: 1. protonation; 2. formation of a delocalized cation; 3. deprotonation at a different position adjacent to the cation.

The term "analog" refers to a chemical compound that is structurally similar to another but differs slightly in composition (as in the replacement of one atom by an atom of a different element or in the presence of a particular functional group, or the replacement of one functional group by another functional group). Thus, an analog is a compound that is similar or comparable in function and appearance, but not in structure or origin to the reference compound.

A "patient," "subject," or "host" to be treated by the subject method may mean either a human or non-human animal, such as a mammal, a fish, a bird, a reptile, or an amphibian. Thus, the subject of the herein disclosed methods can be a human, non-human primate, horse, pig, rabbit, dog, sheep, goat, cow, cat, guinea pig or rodent. The term does not denote a particular age or sex. Thus, adult and newborn subjects, as well as fetuses, whether male or female, are intended to be covered. In one aspect, the subject is a mammal. A patient refers to a subject afflicted with a disease or disorder.

The terms "prophylactic" or "therapeutic" treatment is art-recognized and includes administration to the host of one or more of the subject compositions. If it is administered prior to clinical manifestation of the unwanted condition (e.g., disease or other unwanted state of the host animal) then the treatment is prophylactic, i.e., it protects the host against developing the unwanted condition, whereas if it is administered after manifestation of the unwanted condition, the treatment is therapeutic (i.e., it is intended to diminish, ameliorate, or stabilize the existing unwanted condition or side effects thereof).

The terms "therapeutic agent", "drug", "medicament" and "bioactive substance" are art-recognized and include molecules and other agents that are biologically, physiologically, or pharmacologically active substances that act locally or systemically in a patient or subject to treat a disease or condition. The terms include without limitation pharmaceutically acceptable salts thereof and prodrugs. Such agents may be acidic, basic, or salts; they may be neutral molecules, polar molecules, or molecular complexes capable of hydrogen bonding; they may be prodrugs in the form of ethers, esters, amides and the like that are biologically activated when administered into a patient or subject.

The phrase "therapeutically effective amount" or "pharmaceutically effective amount" is an art-recognized term. In certain embodiments, the term refers to an amount of a therapeutic agent that produces some desired effect at a reasonable benefit/risk ratio applicable to any medical treatment. In certain embodiments, the term refers to that amount necessary or sufficient to eliminate, reduce or maintain a target of a particular therapeutic regimen. The effective amount may vary depending on such factors as the disease or condition being treated, the particular targeted constructs being administered, the size of the subject or the severity of the disease or condition. One of ordinary skill in the art may empirically determine the effective amount of a particular compound without necessitating undue experimentation. In certain embodiments, a therapeutically effective amount of a therapeutic agent for in vivo use will likely depend on a number of factors, including: the rate of release of an agent from a polymer matrix, which will depend in part on the chemical and physical characteristics of the polymer; the identity of the agent; the mode and method of administration; and any other materials incorporated in the polymer matrix in addition to the agent.

The term "ED50" is art-recognized. In certain embodiments, ED50 means the dose of a drug, which produces 50% of its maximum response or effect, or alternatively, the dose, which produces a pre-determined response in 50% of test subjects or preparations. The term "LD50" is art-recognized. In certain embodiments, LD50 means the dose of a drug, which is lethal in 50% of test subjects. The term "therapeutic index" is an art-recognized term, which refers to the therapeutic index of a drug, defined as LD50/ED50.

The terms "IC$_{50}$," or "half maximal inhibitory concentration" is intended to refer to the concentration of a substance (e.g., a compound or a drug) that is required for 50% inhibition of a biological process, or component of a process, including a protein, subunit, organelle, ribonucleoprotein, etc.

With respect to any chemical compounds, the present application is intended to include all isotopes of atoms occurring in the present compounds. Isotopes include those atoms having the same atomic number but different mass numbers. By way of general example and without limitation, isotopes of hydrogen include tritium and deuterium, and isotopes of carbon include C-13 and C-14.

When a bond to a substituent is shown to cross a bond connecting two atoms in a ring, then such substituent can be bonded to any atom in the ring. When a substituent is listed without indicating the atom via which such substituent is bonded to the rest of the compound of a given formula, then such substituent can be bonded via any atom in such substituent. Combinations of substituents and/or variables are permissible, but only if such combinations result in stable compounds.

When an atom or a chemical moiety is followed by a subscripted numeric range (e.g., $C_{1-6}$), it is meant to encompass each number within the range as well as all intermediate ranges. For example, "$C_{1-6}$ alkyl" is meant to include alkyl groups with 1, 2, 3, 4, 5, 6, 1-6, 1-5, 1-4, 1-3, 1-2, 2-6, 2-5, 2-4, 2-3, 3-6, 3-5, 3-4, 4-6, 4-5, and 5-6 carbons.

The term "alkyl" is intended to include both branched (e.g., isopropyl, tert-butyl, isobutyl), straight-chain e.g., methyl, ethyl, propyl, butyl, pentyl, hexyl, heptyl, octyl, nonyl, decyl), and cycloalkyl (e.g., alicyclic) groups (e.g., cyclopropyl, cyclopentyl, cyclohexyl, cycloheptyl, cyclooctyl), alkyl substituted cycloalkyl groups, and cycloalkyl substituted alkyl groups. Such aliphatic hydrocarbon groups have a specified number of carbon atoms. For example, $C_{1-6}$ alkyl is intended to include $C_1$, $C_2$, $C_3$, $C_4$, $C_5$, and $C_6$ alkyl groups. As used herein, "lower alkyl" refers to alkyl groups having from 1 to 6 carbon atoms in the backbone of the carbon chain. "Alkyl" further includes alkyl groups that have oxygen, nitrogen, sulfur or phosphorous atoms replacing one or more hydrocarbon backbone carbon atoms. In certain embodiments, a straight chain or branched chain alkyl has six or fewer carbon atoms in its backbone (e.g., $C_1$-$C_6$ for straight chain, $C_3$-$C_6$ for branched chain), for example four or fewer. Likewise, certain cycloalkyls have from three to eight carbon atoms in their ring structure, such as five or six carbons in the ring structure.

The term "substituted alkyls" refers to alkyl moieties having substituents replacing a hydrogen on one or more carbons of the hydrocarbon backbone. Such substituents can include, for example, alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Cycloalkyls can be further substituted, e.g., with the substituents described above. An "alkylaryl" or an "aralkyl" moiety is an alkyl substituted with an aryl (e.g., phenylmethyl (benzyl)). If not otherwise indicated, the terms "alkyl" and "lower alkyl" include linear, branched, cyclic, unsubstituted, substituted, and/or heteroatom-containing alkyl or lower alkyl, respectively.

The term "alkenyl" refers to a linear, branched or cyclic hydrocarbon group of 2 to about 24 carbon atoms containing at least one double bond, such as ethenyl, n-propenyl, isopropenyl, n-butenyl, isobutenyl, octenyl, decenyl, tetradecenyl, hexadecenyl, eicosenyl, tetracosenyl, cyclopentenyl, cyclohexenyl, cyclooctenyl, and the like. Generally, although again not necessarily, alkenyl groups can contain 2 to about 18 carbon atoms, and more particularly 2 to 12 carbon atoms. The term "lower alkenyl" refers to an alkenyl group of 2 to 6 carbon atoms, and the specific term "cycloalkenyl" intends a cyclic alkenyl group, preferably having 5 to 8 carbon atoms. The term "substituted alkenyl" refers to alkenyl substituted with one or more substituent groups, and the terms "heteroatom-containing alkenyl" and "heteroalkenyl" refer to alkenyl or heterocycloalkenyl (e.g., heterocylcohexenyl) in which at least one carbon atom is replaced with a heteroatom. If not otherwise indicated, the terms "alkenyl" and "lower alkenyl" include linear, branched, cyclic, unsubstituted, substituted, and/or heteroatom-containing alkenyl and lower alkenyl, respectively.

The term "alkynyl" refers to a linear or branched hydrocarbon group of 2 to 24 carbon atoms containing at least one triple bond, such as ethynyl, n-propynyl, and the like. Generally, although again not necessarily, alkynyl groups can contain 2 to about 18 carbon atoms, and more particularly can contain 2 to 12 carbon atoms. The term "lower alkynyl" intends an alkynyl group of 2 to 6 carbon atoms. The term "substituted alkynyl" refers to alkynyl substituted with one or more substituent groups, and the terms "heteroatom-containing alkynyl" and "heteroalkynyl" refer to alkynyl in which at least one carbon atom is replaced with a heteroatom. If not otherwise indicated, the terms "alkynyl" and "lower alkynyl" include linear, branched, unsubstituted, substituted, and/or heteroatom-containing alkynyl and lower alkynyl, respectively.

The terms "alkyl", "alkenyl", and "alkynyl" are intended to include moieties which are diradicals, i.e., having two points of attachment. A nonlimiting example of such an alkyl moiety that is a diradical is —$CH_2CH_2$—, i.e., a $C_2$ alkyl group that is covalently bonded via each terminal carbon atom to the remainder of the molecule.

The term "alkoxy" refers to an alkyl group bound through a single, terminal ether linkage; that is, an "alkoxy" group may be represented as —O-alkyl where alkyl is as defined above. A "lower alkoxy" group intends an alkoxy group containing 1 to 6 carbon atoms, and includes, for example, methoxy, ethoxy, n-propoxy, isopropoxy, t-butyloxy, etc. Preferred substituents identified as "$C_1$-$C_6$ alkoxy" or "lower alkoxy" herein contain 1 to 3 carbon atoms, and particularly preferred such substituents contain 1 or 2 carbon atoms (i.e., methoxy and ethoxy).

The term "aryl" refers to an aromatic substituent containing a single aromatic ring or multiple aromatic rings that are fused together, directly linked, or indirectly linked (such that the different aromatic rings are bound to a common group such as a methylene or ethylene moiety). Aryl groups can contain 5 to 20 carbon atoms, and particularly preferred aryl groups can contain 5 to 14 carbon atoms. Examples of aryl groups include benzene, phenyl, pyrrole, furan, thiophene, thiazole, isothiazole, imidazole, triazole, tetrazole, pyrazole, oxazole, isooxazole, pyridine, pyrazine, pyridazine, and pyrimidine, and the like. Furthermore, the term "aryl" includes multicyclic aryl groups, e.g., tricyclic, bicyclic, e.g., naphthalene, benzoxazole, benzodioxazole, benzothiazole, benzoimidazole, benzothiophene, methylenedioxyphenyl, quinoline, isoquinoline, napthridine, indole, benzofuran, purine, benzofuran, deazapurine, or indolizine. Those aryl groups having heteroatoms in the ring structure may also be referred to as "aryl heterocycles", "heterocycles," "heteroaryls" or "heteroaromatics". The aromatic ring can be substituted at one or more ring positions with such substituents as described above, as for example, halogen, hydroxyl, alkoxy, alkylcarbonyloxy, arylcarbonyloxy, alkoxycarbonyloxy, aryloxycarbonyloxy, carboxylate, alkylcarbonyl, alkylaminocarbonyl, aralkylaminocarbonyl, alkenylaminocarbonyl, alkylcarbonyl, arylcarbonyl, aralkylcarbonyl, alkenylcarbonyl, alkoxycarbonyl, aminocarbonyl, alkylthiocarbonyl, phosphate, phosphonato, phosphinato, cyano, amino (including alkylamino, dialkylamino, arylamino, diaryl amino, and al kylaryl amino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Aryl groups can also be fused or bridged with alicyclic or heterocyclic rings, which are not aromatic so as to form a multicyclic system (e.g., tetralin, methylenedioxyphenyl). If not otherwise indicated, the term "aryl" includes unsubstituted, substituted, and/or heteroatom-containing aromatic substituents.

The terms "heterocyclyl" or "heterocyclic group" include closed ring structures, e.g., 3- to 10-, or 4- to 7-membered rings, which include one or more heteroatoms. "Heteroatom" includes atoms of any element other than carbon or hydrogen. Examples of heteroatoms include nitrogen, oxygen, sulfur and phosphorus.

Heterocyclyl groups can be saturated or unsaturated and include pyrrolidine, oxolane, thiolane, piperidine, piperazine, morpholine, lactones, lactams, such as azetidinones and pyrrolidinones, sultams, and sultones. Heterocyclic groups such as pyrrole and furan can have aromatic character. They include fused ring structures, such as quinoline and isoquinoline. Other examples of heterocyclic groups include pyridine and purine. The heterocyclic ring can be substituted at one or more positions with such substituents as described above, as for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, trifluoromethyl, cyano, azido, heterocyclyl, or an aromatic or heteroaromatic moiety. Heterocyclic groups can also be substituted at one or more constituent atoms with, for example, a lower alkyl, a lower alkenyl, a lower alkoxy, a lower alkylthio, a lower alkylamino, a lower alkylcarboxyl, a nitro, a hydroxyl, —$CF_3$, or —CN, or the like.

The term "halo" or "halogen" refers to fluoro, chloro, bromo, and iodo. "Counterion" is used to represent a small, negatively charged species such as fluoride, chloride, bromide, iodide, hydroxide, acetate, and sulfate. The term sulfoxide refers to a sulfur attached to 2 different carbon atoms and one oxygen and the S—O bond can be graphically represented with a double bond (S═O), a single bond without charges (S—O) or a single bond with charges [S(+)—O(−)].

The terms "substituted" as in "substituted alkyl," "substituted aryl," and the like, as alluded to in some of the aforementioned definitions, is meant that in the alkyl, aryl, or other moiety, at least one hydrogen atom bound to a carbon (or other) atom is replaced with one or more non-hydrogen substituents. Examples of such substituents include, without limitation: functional groups such as halo, hydroxyl, silyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl (including $C_2$-$C_{24}$ alkylcarbonyl (—CO-alkyl) and $C_6$-$C_{20}$ arylcarbonyl (—CO-aryl)), acyloxy (—O-acyl), $C_2$-$C_{24}$ alkoxycarbonyl (—(CO)—O-alkyl), $C_6$-$C_{20}$ aryloxycarbonyl (—(CO)—O-aryl), $C_2$-$C_{24}$ alkylcarbonato (—O—(CO)—O-alkyl), $C_6$-$C_{20}$ arylcarbonato (—O—(CO)—O-aryl), carboxy (—COOH), carboxylato (—COO—), carbamoyl (—(CO)—NH$_2$), mono-($C_1$-$C_{24}$ alkyl)-substituted carbamoyl (—(CO)—NH($C_1$-$C_{24}$ alkyl)), di-($C_1$-$C_4$ alkyl)-substituted carbamoyl (—(CO)—N($C_1$-$C_{24}$ alkyl)$_2$), mono-substituted arylcarbamoyl (—(CO)—NH-aryl), thiocarbamoyl (—(CS)—NH$_2$), carbamido (—NH—(CO)—NH$_2$), cyano (—CN), isocyano (—N$^+$C$^-$), cyanato (—O—CN), isocyanato (—ON$^+$C$^-$), isothiocyanato (—S—CN), azido (—N=N$^+$=N$^-$), formyl (—(CO)—H), thioformyl (—(CS)—H), amino (—NH$_2$), mono- and di-($C_1$-$C_{24}$ alkyl)-substituted amino, mono- and di-($C_5$-$C_{20}$ aryl)-substituted amino, $C_2$-$C_{24}$ alkylamido (—NH—(CO)-alkyl), $C_6$-$C_{20}$ arylamido (—NH—(CO)-aryl), imino (—CR=NH where R=hydrogen, $C_1$-$C_{24}$ alkyl, $C_5$-$C_{20}$ aryl, $C_6$-$C_{24}$ alkaryl, $C_6$-$C_{24}$ aralkyl, etc.), alkylimino (—CR=N(alkyl), where R=hydrogen, alkyl, aryl, alkaryl, etc.), arylimino (—CR=N (aryl), where R=hydrogen, alkyl, aryl, alkaryl, etc.), nitro (—NO$_2$), nitroso (—NO), sulfo (—SO$_2$—OH), sulfonato (—SO$_2$—O$^-$), $C_1$-$C_{24}$ alkylsulfanyl (—S-alkyl; also termed "alkylthio"), arylsulfanyl (—S-aryl; also termed "arylthio"), $C_1$-$C_{24}$ alkylsulfinyl (—(SO)-alkyl), $C_5$-$C_{20}$ arylsulfinyl (—(SO)-aryl), $C_1$-$C_{24}$ alkylsulfonyl (—SO$_2$-alkyl), $C_5$-$C_{20}$ arylsulfonyl (—SO$_2$-aryl), phosphono (—P(O)(OH)$_2$), phosphonato (—P(O)(O)$_2$), phosphinato (—P(O)(O$^-$)), phospho (—PO$_2$), and phosphino (—PH$_2$); and the hydrocarbyl moieties $C_1$-$C_{24}$ alkyl, $C_2$-$C_{24}$ alkenyl, $C_2$-$C_{24}$ alkynyl, $C_5$-$C_{20}$ aryl, $C_6$-$C_{24}$ alkaryl, and $C_6$-$C_{24}$ aralkyl.

In addition, the aforementioned functional groups may, if a particular group permits, be further substituted with one or more additional functional groups or with one or more hydrocarbyl moieties such as those specifically enumerated above. Analogously, the above-mentioned hydrocarbyl moieties may be further substituted with one or more functional groups or additional hydrocarbyl moieties such as those specifically enumerated.

When the term "substituted" appears prior to a list of possible substituted groups, it is intended that the term apply to every member of that group. For example, the phrase "substituted alkyl, alkenyl, and aryl" is to be interpreted as "substituted alkyl, substituted alkenyl, and substituted aryl." Analogously, when the term "heteroatom-containing" appears prior to a list of possible heteroatom-containing groups, it is intended that the term apply to every member of that group. For example, the phrase "heteroatom-containing alkyl, alkenyl, and aryl" is to be interpreted as "heteroatom-containing alkyl, substituted alkenyl, and substituted aryl.

"Optional" or "optionally" means that the subsequently described circumstance may or may not occur, so that the description includes instances where the circumstance occurs and instances where it does not. For example, the phrase "optionally substituted" means that a non-hydrogen substituent may or may not be present on a given atom, and, thus, the description includes structures wherein a non-hydrogen substituent is present and structures wherein a non-hydrogen substituent is not present.

The terms "stable compound" and "stable structure" are meant to indicate a compound that is sufficiently robust to survive isolation, and as appropriate, purification from a reaction mixture, and formulation into an efficacious therapeutic agent.

The terms "free compound" is used herein to describe a compound in the unbound state.

Throughout the description, where compositions are described as having, including, or comprising, specific components, it is contemplated that compositions also consist essentially of, or consist of, the recited components. Similarly, where methods or processes are described as having, including, or comprising specific process steps, the processes also consist essentially of, or consist of, the recited processing steps. Further, it should be understood that the order of steps or order for performing certain actions is immaterial so long as the compositions and methods described herein remains operable. Moreover, two or more steps or actions can be conducted simultaneously.

The term "inflammation" generally refers to a biological response of tissues to harmful stimuli, such as pathogens, damaged cells, irritants, etc Inflammation can be either acute or chronic. Acute inflammation is an initial response of the body to harmful stimuli and can be achieved by the increased movement of plasma and leukocytes from the blood into injured tissues. An inflammatory response can involve the local vascular system, the immune system, and/or various cells within the injured tissue. Prolonged inflammation, referred to as chronic inflammation, can lead to a progressive shift in the type of cells which are present at the site of inflammation can be characterized by simultaneous destruction and healing of the tissue from the inflammatory process.

The term "neoplasm" refers to any abnormal mass of cells or tissue as a result of neoplasia. The neoplasm may be benign, potentially malignant (precancerous), or malignant (cancerous). An adenoma is an example of a neoplasm.

The term "neoplastic cell" refers to a cell that shows aberrant cell growth, such as increased, uncontrolled cell growth. A neoplastic cell can be a hyperplastic cell, a cell from a cell line that shows a lack of contact inhibition when grown in vitro, a tumor cell, or a cancer cell that is capable of metastasis in vivo. Alternatively, a neoplastic cell can be termed a "cancer cell." Non-limiting examples of cancer cells can include lymphoma cells, melanoma cells, sarcoma cells, leukemia cells, retinoblastoma cells, hepatoma cells, myeloma cells, glioma cells, mesothelioma cells, carcinoma cells and adenocarcinoma cells.

"Phototherapy procedure" refers to a therapeutic procedure involving administration of a phototherapeutic agent to a patient followed by subsequent excitation by exposure to applied electromagnetic radiation, such as electromagnetic radiation having wavelengths in the ultraviolet and/or near IR region of the electromagnetic spectrum such as wavelengths in the range of about 300 nm to about 1400 nm, so as to generate a therapeutically effective amount of excited phototherapeutic agent. Phototherapy includes, but is not limited to, photodynamic therapy. As used herein phototherapy includes procedures involving administration of Type 1 and/or Type 2 phototherapeutic agents, optionally further including administration of one or more additional therapeutic agents. In an embodiment, the invention provides methods for carrying out a phototherapy procedure for treatment of cancer, inflammation, stenosis and vascular disease.

The term "tumor" refers to an abnormal mass or population of cells that result from excessive cell division, whether malignant or benign, and all pre-cancerous and cancerous cells and tissues.

All percentages and ratios used herein, unless otherwise indicated, are by weight.

Embodiments described herein relate to compounds comprising thio-substituted nucleobases, nucleosides, nucleotides, and/or analogs thereof for use in photodynamic therapy or phototherapy procedures, and particularly relate to the use of dithio-substituted pyrimidine and purine nucleobases, nucleosides, nucleotides, and/or analogs thereof for use in phototherapy procedures.

Sulfur substitution of a carbonyl atom in any of the natural DNA or RNA bases produces a family of nucleic acid analogues known as thiobases. Dithio-substituted nucleobases, such as dithio-substituted pyrimidine and purine nucleobases, nucleosides, nucleotides, and/or analogs thereof, were found to strongly absorb light within the ultraviolet-A (UVA) to infrared region of the electromagnetic spectrum that is at least about 25 nm red-shifted compared to similar mono-thio-substituted nucleobases, and facilitate at least 30% deeper tissue treatment upon administration compared to similar mono-thio-substituted nucleobases. Advantageously, upon absorption of light within the ultraviolet-A (UVA) to infrared region of the electromagnetic spectrum, the dithio-substituted nucleobases, nucleosides, nucleotides, and/or analogs thereof were found to populate long-lived and highly reactive excited states, which favor photochemical reaction over photostability.

In some embodiments, dithio-substituted nucleobases, nucleosides, nucleotides, and/or analogs thereof for use in photodynamic therapy or phototherapy procedures described herein can include a compound having the formula:

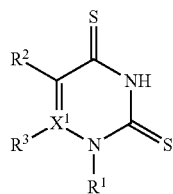

wherein $X^1$ is C or N, $R^1$ is H, OH, ribose, deoxyribose, amino acid residue(s), fatty acid residue(s), $OR_a$, where $R_a$ comprises at least one of a straight chain, branched or cyclic alkyl, CO-alkyl, CO-aryl, CO-alkoxyalkyl, arylsulfonyl, or aralkylsulfonyl, or a mono, di, or triphosphate thereof, $R^2$ and $R^3$ are the same or different and are independently selected from the group consisting of hydrogen, substituted or unsubstituted $C_1$-$C_{24}$ alkyl, $C_2$-$C_{24}$ alkenyl, $C_2$-$C_{24}$ alkynyl, $C_3$-$C_{20}$ aryl, heteroaryl, heterocycloalkenyl containing from 5-6 ring atoms (wherein from 1-3 of the ring atoms is independently selected from N, NH, N($C_1$-$C_6$ alkyl), NC(O) ($C_1$-$C_6$ alkyl), O, and S), $C_6$-$C_{24}$ alkaryl, $C_6$-$C_{24}$ aralkyl, halo, —Si($C_1$-$C_3$ alkyl)$_3$, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl (including $C_2$-$C_{24}$ alkylcarbonyl (—CO-alkyl) and $C_6$-$C_{20}$ arylcarbonyl (—CO-aryl)), acyloxy (—O-acyl), $C_2$-$C_{24}$ alkoxycarbonyl (—(CO)—O-alkyl), $C_6$-$C_{20}$ aryloxycarbonyl (—(CO)—O-aryl), $C_2$-$C_{24}$ alkylcarbonato (—O—(CO)—O-alkyl), $C_6$-$C_{20}$ arylcarbonato (—O—(CO)—O-aryl), carboxy (—COOH), carboxylato (—COO$^-$), carbamoyl (—(CO)—NH$_2$), $C_1$-$C_{24}$ alkyl-carbamoyl (—(CO)—NH($C_1$-$C_{24}$ alkyl)), arylcarbamoyl (—(CO)—NH-aryl), thiocarbamoyl (—(CS)—NH$_2$), carbamido (—NH—(CO)—NH$_2$), cyano (—CN), isocyano (—N$^+$C$^-$), cyanato (—O—CN), isocyanato (—O—N$^+$=C$^-$), isothiocyanato (—S—CN), azido (—N=N$^+$=N$^-$), formyl (—(CO)—H), thioformyl (—(CS)—H), amino (—NH$_2$), $C_1$-$C_{24}$ alkyl amino, $C_5$-$C_{20}$ aryl amino, $C_2$-$C_{24}$ alkylamido (—NH—(CO)-alkyl), $C_6$-$C_{20}$ arylamido (—NH—(CO)-aryl), imino (—CR=NH where R is hydrogen, $C_1$-$C_{24}$ alkyl, $C_5$-$C_{20}$ aryl, $C_6$-$C_{24}$ alkaryl, $C_6$-$C_{24}$ aralkyl, etc.), alkylimino (—CR=N(alkyl), where R=hydrogen, alkyl, aryl, alkaryl, aralkyl, etc.), arylimino (—CR=N (aryl), where R=hydrogen, alkyl, aryl, alkaryl, etc.), nitro (—NO$_2$), nitroso (—NO), sulfo (—SO$_2$—OH), sulfonato (—SO$_2$—O$^-$), $C_1$-$C_{24}$ alkylsulfanyl (—S-alkyl; also termed "alkylthio"), arylsulfonyl (—S-aryl; also termed "arylthio"), $C_1$-$C_{24}$ alkylsulfinyl (—(SO)-alkyl), $C_5$-$C_{20}$ arylsulfinyl (—(SO)-aryl), $C_1$-$C_{24}$ alkylsulfonyl (—SO$_2$-alkyl), $C_5$-$C_{20}$ arylsulfonyl (—SO$_2$-aryl), phosphono (—P(O)(OH)$_2$), phosphonato (—P(O)(O$^-$)$_2$), phosphinato (—P(O)(O$^-$)), phospho (—PO$_2$), phosphino (—PH$_2$), and combinations thereof, and wherein $R^2$ and $R^3$ may be linked to form a cyclic or polycyclic ring, wherein the ring is a substituted or unsubstituted aryl, a substituted or unsubstituted heteroaryl, a substituted or unsubstituted cycloalkyl, and a substituted or unsubstituted heterocyclyl, and pharmaceutically acceptable salts thereof. The compound administered to the subject can then be exposed to electromagnetic radiation.

In some embodiments, $R^2$ and $R^3$ are the same or different and are independently selected from the group consisting of a H, F, Cl, Br, I, a lower alkyl group, $(CH_2)_{n1}OR'$ (wherein n1=1, 2, or 3), $CF_3$, $CH_2$—$CH_2X$, O—$CH_2$—$CH_2X$, $CH_2$—$CH_2$—$CH_2X$, O—$CH_2$—$CH_2X$ (wherein X=F, Cl, Br, or I), CN, (C=O)—R', N(R')$_2$, NO$_2$, (C=O)N(R')$_2$, O(CO)R', OR', SR', COOR' (wherein R' is H or a lower alkyl group); substituted or unsubstituted aryl, heteroaryl, cycloalkyl, or heterocyclyl, and wherein $R^2$ and $R^3$ may be linked to form a cyclic or polycyclic ring, wherein the ring is a substituted or unsubstituted aryl, a substituted or unsubstituted heteroaryl, a substituted or unsubstituted cycloalkyl, and a substituted or unsubstituted heterocyclyl, and pharmaceutically acceptable salts thereof.

In other embodiments, the compound can be selected from the group consisting of:

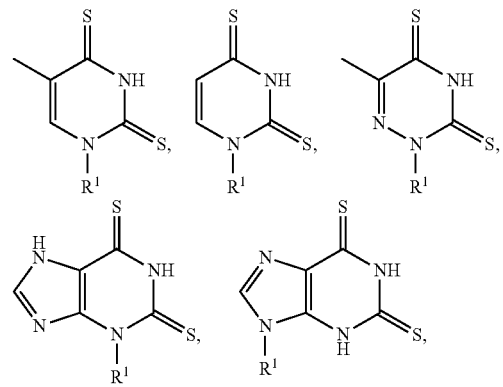

wherein $R^1$ is H, OH, ribose, deoxyribose, amino acid residue(s), fatty acid residue(s), $OR_a$, where $R_a$ comprises at least one of a straight chain, branched or cyclic alkyl, CO-alkyl, CO-aryl, CO-alkoxyalkyl, arylsulfonyl, or aralkylsulfonyl, or a mono, di, or triphosphate thereof, and pharmaceutically acceptable salts thereof.

In still other embodiments, the compound can have the formula:

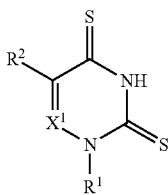

wherein $X^1$ is C or N, $R^1$ is H, OH, ribose, deoxyribose, amino acid residue(s), fatty acid residue(s), $OR_a$, where $R_a$ comprises at least one of a straight chain, branched or cyclic alkyl, CO-alkyl, CO-aryl, CO-alkoxyalkyl, arylsulfonyl, or aralkylsulfonyl, or a mono, di, or triphosphate thereof, and a. $R^2$ is selected from the group consisting of a H, F, Cl, Br, I, a lower alkyl group, $(CH_2)_{n1}OR'$ (wherein n1=1, 2, or 3), $CF_3$, $CH_2$—$CH_2X$, O—$CH_2$—$CH_2X$, $CH_2$—$CH_2$—$CH_2X$, O—$CH_2$—$CH_2X$ (wherein X=F, Cl, Br, or I), CN, (C=O)—R', $N(R')_2$, $NO_2$, (C=O)$N(R')_2$, O(CO)R', OR', SR', COOR' (wherein R' is H or a lower alkyl group); substituted or unsubstituted aryl, heteroaryl, cycloalkyl, or heterocyclyl, and pharmaceutically acceptable salts thereof. For example, $R^2$ can be selected from group consisting of H, F, Cl, Br, I, a lower alkyl group, $(CH_2)_{n1}OR'$ (wherein n1=1, 2, or 3), $CF_3$, $CH_2$—$CH_2X$, O—$CH_2$—$CH_2X$, $CH_2$—$CH_2$—$CH_2X$, O—$CH_2$—$CH_2X$ (wherein X=F, Cl, Br, or I), CN, (C=O)—R', $N(R')_2$, $NO_2$, (C=O)$N(R')_2$, O(CO)R', OR', SR', and COOR' (wherein R' is H or a lower alkyl group).

The compounds described herein can be used in phototherapy procedures to treat a subject having or suspected of having a disease, disorder, or condition, such as cancer, a cancer associated disorder, and/or an inflammation associated disorder. In some embodiments, a method of using the compound in a phototherapy procedure can include administering to a subject in need of treatment a therapeutically effective amount of the compound. Upon administration, the compound is allowed to accumulate in target regions of interest (e.g., target tissue, tumor, or organ). To induce selective tissue damage, the compound can be activated by exposure to electromagnetic radiation. In an embodiment, the compound is activated after an effective concentration of the compound has accumulated in a target tissue. An effective concentration of the compound depends on the nature of the formulation, method of delivery, target tissue, activation method and toxicity to the surrounding normal non-target tissue. Exposure to electromagnetic radiation and activation of the compound may occur during or after administration of the compound and accumulation at the target tissue.

For photoactivation, the target region is illuminated with electromagnetic radiation having wavelengths in the ultraviolet A region to the infrared region of the electromagnetic spectrum, for example, in the range of about 300 nm to about 1400 nm, about 350 nm to about 1300 nm, or about 350 nm to about 900 nm. In one particular embodiment UV light is used that has a wavelength of from about 300 nm to about 400 nm, such as from about 350 nm to about 400 nm, and such as about 365 nm to about 395 nm. However, other wavelengths of light energy (e.g., blue-violet light having a wavelength of about 380 nm to about 465 nm) may be utilized.

The targeted cells can be illuminated with the light energy for any desired time determined according to the treatment guidelines. Generally, the treatment process can involve repeated exposure to light energy for short intervals of time (e.g., from about 2 minutes to about 10 minutes); however, any period of exposure can be utilized according to particular treatment plan prescribed by the attending physician(s).

The light source can be any of the commercially available light sources, which are commonly available having a light source of, for example, about 365 nm to about 395 nm.

In some embodiments, the wavelengths of the electromagnetic radiation correspond to a peak in the absorption spectrum of the compound, for example is within 20 nanometers of a peak in the absorption spectrum of the compound. In some phototherapeutic procedures, the target site is exposed to electromagnetic radiation having sufficient fluence and/or power sufficient to activate the compound so as to induce cell death, for example via necrosis or apoptosis processes. In some embodiments, electromagnetic radiation of low energy, power and/or fluence is needed to activate the compound. If the region of interest is, for example a lesion on the skin surface, the region can be directly illuminated. Otherwise, endoscopic catheters equipped with an electromagnetic radiation source may be employed to provide a photodiagnostic and/or the phototherapeutic effect.

Appropriate power and intensity of the electromagnetic radiation depends on the size, depth, and the pathology of the lesion, as is known to one skilled in the art. In an embodiment, the fluence of the electromagnetic radiation is preferably, but not always, kept below 200 mW/cm² to minimize undesirable thermal effects. The intensity, power, and duration of the illumination, and the wavelength of the electromagnetic radiation may vary widely depending on the body location, the lesions site, the effect to be achieved, etc. Appropriate power depends on the size, depth, and the pathology of the lesion, as is known to one skilled in the art. In an embodiment, the power is selected over the range of 1-500 mW/cm², and optionally selected over the range of 1-200 mW/cm². In an embodiment, the duration of the exposure to electromagnetic radiation is selected over the range of 1 second to 60 minutes.

The compounds described herein can be formulated into pharmaceutical, therapeutic and/or diagnostic compositions for enteral (oral or rectal), parenteral, topical, or cutaneous administration. Topical or cutaneous delivery of the compounds may also include aerosol formulation, creams, gels, solutions, etc. The compounds are administered in doses effective to achieve the desired diagnostic or therapeutic effect. Such doses may vary widely depending upon the particular complex employed, the organs or tissues to be examined, the equipment employed in the clinical procedure, the efficacy of the treatment achieved, and the like.

In some embodiments, a method of using the compounds in a phototherapy procedure includes administering to a subject a therapeutically effective amount of the compound having the following formula:

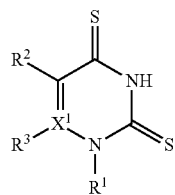

wherein $X^1$ is C or N, $R^1$ is H, OH, ribose, deoxyribose, amino acid residue(s), fatty acid residue(s), $OR_a$, where $R_a$ comprises at least one of a straight chain, branched or cyclic alkyl, CO-alkyl, CO-aryl, CO-alkoxyalkyl, arylsulfonyl, or aralkylsulfonyl, or a mono, di, or triphosphate thereof, a. $R^2$ and $R^3$ are the same or different and are independently selected from the group consisting of hydrogen, substituted or unsubstituted $C_1$-$C_{24}$ alkyl, $C_2$-$C_{24}$ alkenyl, $C_2$-$C_{24}$ alkynyl, $C_3$-$C_{20}$ aryl, heteroaryl, heterocycloalkenyl containing from 5-6 ring atoms (wherein from 1-3 of the ring atoms is independently selected from N, NH, N($C_1$-$C_6$ alkyl), NC(O)($C_1$-$C_6$ alkyl), O, and S), $C_6$-$C_{24}$ alkaryl, $C_6$-$C_{24}$ aralkyl, halo, —Si($C_1$-$C_3$ alkyl)$_3$, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl (including $C_2$-$C_{24}$ alkylcarbonyl (—CO-alkyl) and $C_6$-$C_{20}$ arylcarbonyl (—CO-aryl)), acyloxy (—O-acyl), $C_2$-$C_{24}$ alkoxycarbonyl (—(CO)—O-alkyl), $C_6$-$C_{20}$ aryloxycarbonyl (—(CO)—O-aryl), $C_2$-$C_{24}$ alkylcarbonato (—O—(CO)—O-alkyl), $C_6$-$C_{20}$ arylcarbonato (—O—(CO)—O-aryl), carboxy (—COOH), carboxylato (—COO$^-$), carbamoyl (—(CO)—NH$_2$), $C_1$-$C_{24}$ alkyl-carbamoyl (—(CO)—NH($C_1$-$C_{24}$ alkyl)), arylcarbamoyl (—(CO)—NH-aryl), thiocarbamoyl (—(CS)—NH$_2$), carbamido (—NH—(CO)—NH$_2$), cyano (—CN), isocyano (—N$^+$C$^-$), cyanato (—O—CN), isocyanato (—O—N$^+$=C$^-$), isothiocyanato (—S—CN), azido (—N=N$^+$=N$^-$), formyl (—(CO)—H), thioformyl (—(CS)—H), amino (—NH$_2$), $C_1$-$C_{24}$ alkyl amino, $C_5$-$C_{20}$ aryl amino, $C_2$-$C_{24}$ alkylamido (—NH—(CO)-alkyl), $C_6$-$C_{20}$ arylamido (—NH—(CO)-aryl), imino (—CR=NH where R is hydrogen, $C_1$-$C_{24}$ alkyl, $C_5$-$C_{20}$ aryl, $C_6$-$C_{24}$ alkaryl, $C_6$-$C_{24}$ aralkyl, etc.), alkylimino (—CR=N(alkyl), where R=hydrogen, alkyl, aryl, alkaryl, aralkyl, etc.), arylimino (—CR=N(aryl), where R=hydrogen, alkyl, aryl, alkaryl, etc.), nitro (—NO$_2$), nitroso (—NO), sulfo (—SO$_2$—OH), sulfonato (—SO$_2$—O$^-$), $C_1$-$C_{24}$ alkylsulfanyl (—S-alkyl; also termed "alkylthio"), arylsulfonyl (—S-aryl; also termed "arylthio"), $C_1$-$C_{24}$ alkylsulfinyl (—(SO)-alkyl), $C_5$-$C_{20}$ arylsulfinyl (—(SO)-aryl), $C_1$-$C_{24}$ alkylsulfonyl (—SO$_2$-alkyl), $C_5$-$C_{20}$ arylsulfonyl (—SO$_2$-aryl), phosphono (—P(O)(OH)$_2$), phosphonato (—P(O)(O$^-$)$_2$), phosphinato (—P(O)(O$^-$)), phospho (—PO$_2$), phosphino (—PH$_2$), and combinations thereof, and wherein $R^2$ and $R^3$ may be linked to form a cyclic or polycyclic ring, wherein the ring is a substituted or unsubstituted aryl, a substituted or unsubstituted heteroaryl, a substituted or unsubstituted cycloalkyl, and a substituted or unsubstituted heterocyclyl, and pharmaceutically acceptable salts thereof. The compound administered to the subject can then be exposed to electromagnetic radiation.

In some embodiments, $R^2$ and $R^3$ are the same or different and are independently selected from the group consisting of a H, F, Cl, Br, I, a lower alkyl group, (CH$_2$)$_{n1}$OR' (wherein n1=1, 2, or 3), CF$_3$, CH$_2$—CH$_2$X, O—CH$_2$—CH$_2$X, CH$_2$—CH$_2$—CH$_2$X, O—CH$_2$—CH$_2$X (wherein X=F, Cl, Br, or I), CN, (C=O)—R', N(R')$_2$, NO$_2$, (C=O)N(R')$_2$, O(CO)R', OR', SR', COOR' (wherein R' is H or a lower alkyl group); substituted or unsubstituted aryl, heteroaryl, cycloalkyl, or heterocyclyl, and wherein $R^2$ and $R^3$ may be linked to form a cyclic or polycyclic ring, wherein the ring is a substituted or unsubstituted aryl, a substituted or unsubstituted heteroaryl, a substituted or unsubstituted cycloalkyl, and a substituted or unsubstituted heterocyclyl, and pharmaceutically acceptable salts thereof.

In other embodiments, the compound can selected from the group consisting of:

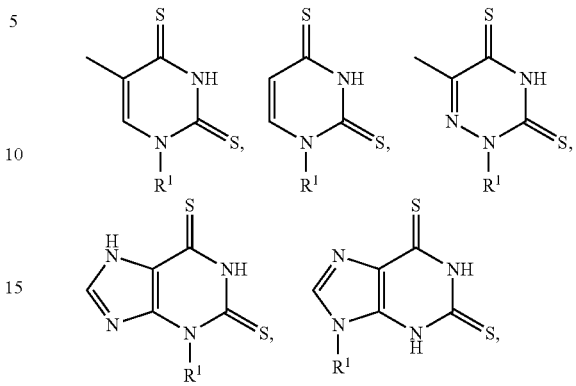

wherein $R^1$ is H, OH, ribose, deoxyribose, amino acid residue(s), fatty acid residue(s), OR$_a$, where R$_a$ comprises at least one of a straight chain, branched or cyclic alkyl, CO-alkyl, CO-aryl, CO-alkoxyalkyl, arylsulfonyl, or aralkylsulfonyl, or a mono, di, or triphosphate thereof, and pharmaceutically acceptable salts thereof.

Embodiments of this aspect may comprise a method of carrying out an in vivo therapeutic and/or diagnostic procedure, such as an in vivo phototherapeutic, photoactivation, and/or photosensitizing procedure. The present methods have broad clinical utility which includes, but is not limited to, phototherapy of tumors, inflammatory processes, and impaired vasculature. In some embodiments, subjects may be any mammal, such as a human, and optionally the subject of the present methods is a patient in need of treatment and/or diagnosis. The present methods are also useful in ex vivo and in vitro procedures, including medical therapeutic and diagnostic procedures.

Methods described herein may optionally further comprise a number of other steps. In an embodiment, the present methods further comprise the step of administering the compound into a bodily fluid of the subject. The compound may be introduced into the patient by any suitable method, including intravenous, intraperitoneal or subcutaneous injection or infusion, oral administration, transdermal absorption through the skin, or by inhalation. In an embodiment, the method further comprises contacting a target tissue, such as an organ, tissue, tumor, lesion, or cell type with a compound prior to or during the exposure step. In an embodiment, the method further comprises allowing the compound to accumulate in a target tissue prior to exposure of the compound to electromagnetic radiation. In an embodiment, the method further comprises targeting compound to a selected organ, tissue, tumor, inflammation, lesion, or cell type. In an embodiment, the compound is administered to the skin, a tumor, surgical site, or a wound site. In an embodiment, the compound is administered and/or delivered to a blood vessel, lung, heart, throat, ear, rectum, bladder, stomach, intestines, esophagus, liver, brain, prostrate, breast or pancreas of the subject.

In some embodiments, a therapeutically effective amount of the compound is provided to the subject. For example, parenteral administration advantageously contains a sterile aqueous solution or suspension of the compound. Parenteral formulations can have a concentration of the compound selected over the range of 1 μM to 10 mM. Such solutions may also contain pharmaceutically acceptable buffers, emulsifiers, surfactants, and, optionally, electrolytes, such as sodium chloride. In an embodiment, the dose of the compound may vary from 0.1 to 500 mg/kg body weight, for example, from 0.5 to 2 mg/kg body weight.

In some methods, the compound can be formulated for enteral (oral or rectal), parenteral, topical, or cutaneous administration. Topical or cutaneous delivery of the compound may also include aerosols, creams, gels, solutions, emulsions and colloids. The compositions are administered in doses effective to achieve the desired diagnostic or therapeutic objective. Such doses may vary widely depending upon the particular complex employed, the organs or tissues to be examined or treated, the equipment employed in the clinical procedure, the efficacy of the treatment achieved, and the like. These compositions contain an effective amount of the compound along with conventional pharmaceutical carriers and excipients appropriate for the type of administration contemplated. These compositions may also include stabilizing agents and skin penetration enhancing agents and also may contain pharmaceutically acceptable buffers, emulsifiers, surfactants, and, optionally, electrolytes, such as sodium chloride. Formulations for enteral administration may vary widely, as is well known in the art. In general, such formulations are liquids, which include an effective amount of the compound in aqueous solution or suspension. Such enteral compositions may optionally include buffers, surfactants, emulsifiers, thixotropic agents, and the like. Compounds for oral administration may also contain flavoring agents and other ingredients for enhancing their organoleptic qualities. Formulations for topical delivery may also contain liquid or semisolid excipients to assist in the penetration of the photosensitizer. The compounds may also be delivered in an aerosol spray.

As will be understood by one having skill in the art, the conditions for the step of exposing the compound administered to the patient to electromagnetic radiation will vary considerably with the (i) therapeutic and/or diagnostic objectives, and (ii) the condition of the subject (e.g., height, weight, state of health etc.).

In an embodiment, the applied electromagnetic radiation has wavelengths, energy and/or fluence sufficient to achieve a desired therapeutic and/or diagnostic result. In an embodiment, the electromagnetic radiation has wavelengths, energy and/or fluence sufficient to activate the compound.

In some methods, the electromagnetic radiation used to expose the compound has wavelengths selected over the range of about 300 nm to about 1400 nm, for example, about 350 nm to about 900 nm. In an embodiment, the electromagnetic radiation used to expose the compound has wavelengths corresponding to a maximum in the absorption spectrum of the compound, for example, a maximum in the ultraviolet-A or near infrared regions of the electromagnetic spectrum. Optionally, excitation is achieved using electromagnetic substantially free (e.g., less than about 10% of total radiant energy), of ultraviolet radiation, for example, to minimize exposure of the subject to electromagnetic radiation capable of causing unwanted cell or tissue damage. Electromagnetic radiation may be provided to the compound using a range of optical sources and/or surgical instrumentation, including a laser, light emitting diodes, fiber optic device, endoscope, catheter, optical filters, or any combination of these.

Compounds and formula(s) described herein include pharmaceutically-acceptable salts and esters of those compounds. In some embodiments, salts include any salts derived from the acids and bases of the formulas herein which are acceptable for use in human or veterinary applications. The term ester refers to hydrolyzable esters of compounds of the names and formulas herein. Salts and esters of the compounds of the formulas herein can include those which have the same or better therapeutic, diagnostic, or pharmaceutical (human or veterinary) general properties as the compounds of the formulas described herein. In one example, a composition described herein is a compound or salt or ester thereof suitable for pharmaceutical formulations.

Compounds described herein can also have prodrug forms. Prodrugs of the compounds are useful in embodiments including compositions and methods. Any compound that will be converted in vivo to provide a biologically, pharmaceutically, diagnostically, or therapeutically active form of a compound is a prodrug. Various examples and forms of prodrugs are well known in the art. Examples of prodrugs are found, inter alia, in: Design of Prodrugs, edited by H. Bundgaard, (Elsevier, 1985); Methods in Enzymology, Vol. 42, at pp. 309-396, edited by K. Widder, et. al. (Academic Press, 1985); A Textbook of Drug Design and Development, edited by Krosgaard-Larsen and H. Bundgaard, Chapter 5, "Design and Application of Prodrugs," by H. Bundgaard, at pp. 113-191 (1991); H. Bundgaard, Advanced Drug Delivery Reviews, Vol. 8, p. 1-38 (1992); H. Bundgaard, et al., Journal of Pharmaceutical Sciences, Vol. 77, p. 285 (1988); and Nogrady (1985) Medicinal Chemistry A Biochemical Approach, Oxford University Press, New York, pages 388-392). A prodrug, such as a pharmaceutically acceptable prodrug, can represent prodrugs of the compounds described herein which are, within the scope of sound medical judgment, suitable for use in contact with the tissues of humans and lower animals without undue toxicity, irritation, allergic response, and the like, commensurate with a reasonable benefit/risk ratio, and effective for their intended use. Prodrugs can be rapidly transformed in vivo to a parent compound of a compound described herein, for example, by hydrolysis in blood or by other cell, tissue, organ, or system processes. Further discussion is provided in: T. Higuchi and V. Stella, Pro-drugs as Novel Delivery Systems, V. 14 of the A.C.S. Symposium Series; and in Edward B. Roche, ed., Bioreversible Carriers in Drug Design, American Pharmaceutical Association and Pergamon Press (1987).

In some embodiments, compounds described herein can be formulated with pharmaceutically-acceptable anions and/or cations. Pharmaceutically-acceptable cations include among others, alkali metal cations (e.g., $Li^+$, $Na^+$, $K^+$), alkaline earth metal cations (e.g., $Ca^{2+}$, $Mg^{2+}$), non-toxic heavy metal cations and ammonium ($NH^{4+}$) and substituted ammonium ($N(R')_4$, where R' is hydrogen, alkyl, or substituted alkyl, i.e., including, methyl, ethyl, or hydroxyethyl, specifically, trimethyl ammonium, triethyl ammonium, and triethanol ammonium cations). Pharmaceutically-acceptable anions include, among others, halides (e.g., $F^-$, $Cl^-$, $Br^-$, $At^-$), sulfate, acetates (e.g., acetate, trifluoroacetate), ascorbates, aspartates, benzoates, citrates, and lactate.

Pharmaceutically acceptable salts can include metal complexes and salts of both inorganic and organic acids. Pharmaceutically acceptable salts can also include metal salts such as aluminum, calcium, iron, magnesium, manganese and complex salts. For example, pharmaceutically acceptable salts can include acid salts, such as acetic, aspartic, alkylsulfonic, arylsulfonic, axetil, benzenesulfonic, benzoic, bicarbonic, bisulfuric, bitartaric, butyric, calcium edetate, camsylic, carbonic, chlorobenzoic, cilexetil, citric, edetic, edisylic, estolic, esyl, esylic, formic, fumaric, gluceptic, gluconic, glutamic, glycolic, glycolylarsanilic, hexamic, hexylresorcjnoic, hydrabamic, hydrobromic, hydrochloric, hydroiodic, hydroxynaphthoic, isethionic, lactic, lactobionic, maleic, malic, malonic, mandelic, methanesulfonic, methylnitric, methylsulfuric, mucic, muconic, napsylic, nitric, oxalic, p-nitromethanesulfonic, pamoic, pantothenic, phosphoric, monohydrogen phosphoric, dihydrogen phosphoric, phthalic, polygalactouronic, propionic, salicylic, stearic, succinic, sulfamic, sulfanlic, sulfonic, sulfuric, tannic, tartaric, teoclic, toluenesulfonic, and the like. Pharmaceutically acceptable salts can be derived from amino acids, such as, cysteine. Other pharmaceutically acceptable salts can be found, for example, in Stahl et al., Handbook of Pharmaceutical Salts: Properties, Selection, and Use, Wiley-VCH, Verlag Helvetica Chimica Acta, Zurich, 2002. (ISBN 3-906390-26-6).

Typically, a compound described herein, or pharmaceutically acceptable salt thereof, is administered to a subject in a diagnostically or therapeutically effective amount. One skilled in the art generally can determine an appropriate dosage.

Compounds formulated as compositions for oral administration can be, for example, prepared in a manner, such that a single dose in one or more oral preparations contains at least about 20 mg of the compound per square meter of subject body surface area, or at least about 50, 100, 150, 200, 300, 400, or 500 mg of the compound per square meter of subject body surface area (the average body surface area for a human is, for example, 1.8 square meters). In particular, a single dose of a composition for oral administration can contain from about 20 to about 600 mg, and in certain aspects from about 20 to about 400 mg, in another aspect from about 20 to about 300 mg, and in yet another aspect from about 20 to about 200 mg of the compound per square meter of subject body surface area. Compositions for parenteral administration can be prepared in a manner such that a single dose contains at least about 20 mg of the compound per square meter of subject body surface area, or at least about 40, 50, 100, 150, 200, 300, 400, or 500 mg of the compound per square meter of subject body surface area. In particular, a single dose in one or more parenteral preparations contains from about 20 to about 500 mg, and in certain aspects from about 20 to about 400 mg, and in another aspect from about 20 to about 450 mg, and in yet another aspect from about 20 to about 350 mg of the compound per square meter of subject body surface area. It should be recognized that these oral and parenteral dosage ranges represent examples of dosage ranges, and are not intended to limit the invention. The dosage regimen actually employed can vary widely, and, therefore, can deviate from the generally preferred dosage regimen. It is contemplated that one skilled in the art will tailor these ranges to the individual subject.

Toxicity and therapeutic efficacy of such compounds can be determined by standard pharmaceutical procedures in cell cultures or experimental animals for determining the $LD_{50}$ (the dose lethal to 50% of the population) and the $ED_{50}$, (the dose therapeutically effective in 50% of the population). The dose ratio between toxic and therapeutic effects is the therapeutic index that can be expressed as the ratio $LD_{50}/ED_{50}$. Compounds that exhibit large therapeutic indices are preferred. While compounds exhibiting toxic side effects can be used, care should be taken to design a delivery system that targets such compounds to the site affected by the disease or disorder in order to minimize potential damage to unaffected cells and reduce side effects.

Data obtained from the cell culture assays and animal studies can be used in formulating a range of dosages for use in humans and other mammals. The dosage of such compounds can fall within a range of circulating plasma or other bodily fluid concentrations that include the $ED_{50}$ and provides clinically efficacious results (i.e., reduction in disease symptoms). The dosage can vary within this range depending upon the dosage form employed and the route of administration utilized. For any compound described herein, the therapeutically effective amount can be estimated initially from cell culture assays. A dosage can be formulated in animal models to achieve a circulating plasma concentration range that includes the $ED_{50}$ (the concentration of the test compound that achieves a half-maximal inhibition of symptoms) as determined in cell culture. Such information can be used to more accurately determine useful dosages in humans and other mammals. Compound levels in plasma can be measured, for example, by high performance liquid chromatography.

An amount of a compound that can be combined with a pharmaceutically acceptable carrier to produce a single dosage form will vary depending upon the patient treated and the particular mode of administration. It will be appreciated by those skilled in the art that the unit content of a compound contained in an individual dose of each dosage form need not in itself constitute a therapeutically effective amount, as the necessary therapeutically effective amount could be reached by administration of a number of individual doses. The selection of dosage depends upon the dosage form utilized, the condition being treated, and the particular purpose to be achieved according to the determination of those skilled in the art.

The dosage and dosage regime for treating a disease or condition can be selected in accordance with a variety of factors, including the type, age, weight, sex, diet and/or medical condition of the patient, the route of administration, pharmacological considerations, such as activity, efficacy, pharmacokinetic and/or toxicology profiles of the particular compound employed, whether a compound delivery system is utilized, and/or whether the compound is administered as a pro-drug or part of a drug combination. Thus, the dosage regime actually employed can vary widely from subject to subject, or disease to disease and different routes of administration can be employed in different clinical settings.

Any route of administration can be used as long as the target of the compound or pharmaceutically acceptable salt is available via that route. Suitable routes of administration include, for example, oral, intravenous, parenteral, inhalation, rectal, nasal, topical (e.g., transdermal and intraocular), intravesical, intrathecal, enteral, pulmonary, intralymphatic, intracavital, vaginal, transurethral, intradermal, aural, intramammary, buccal, orthotopic, intratracheal, intralesional, percutaneous, endoscopical, transmucosal, sublingual, and intestinal administration.

In some embodiments, a method for treating a medical condition includes administering to a subject (e.g. patient) in need thereof, a therapeutically effective amount of a composition that includes a compound described herein. The medical condition can be cancer, or various other diseases, injuries, and disorders, including cardiovascular disorders such as atherosclerosis and vascular restenosis, inflammatory diseases, ophthalmic diseases and dermatological diseases.

The diagnostic and therapeutic formulations can be administered alone, but can be administered with a pharmaceutical carrier selected upon the basis of the chosen route of administration and standard pharmaceutical practice.

The present compositions, preparations and formulations can be formulated into diagnostic or therapeutic compositions for enteral, parenteral, topical, aerosol, inhalation, or cutaneous administration. Topical or cutaneous delivery of the compositions, preparations and formulations can also include aerosol formulation, creams, gels, solutions, etc. The present compositions, preparations and formulations are administered in doses effective to achieve the desired diagnostic and/or therapeutic effect. Such doses can vary widely depending upon the particular compositions employed in the composition, the organs or tissues to be examined, the equipment employed in the clinical procedure, the efficacy of the treatment achieved, and the like. These compositions, preparations and formulations contain an effective amount of the composition(s), along with conventional pharmaceutical carriers and excipients appropriate for the type of administration contemplated. These compositions, preparations and formulations can also optionally include stabilizing agents and skin penetration enhancing agents.

Compounds described herein can be formulated for parenteral administration by injection (e.g., by bolus injection or continuous infusion). Formulations for injection can be presented in unit dosage form in ampoules or in multi-dose containers with an optional preservative added. The parenteral preparation can be enclosed in ampoules, disposable syringes or multiple dose vials made of glass, plastic or the like. The formulation can take such forms as suspensions, solutions or emulsions in oily or aqueous vehicles, and can contain formulatory agents such as suspending, stabilizing and/or dispersing agents.

For example, a parenteral preparation can be a sterile injectable solution or suspension in a nontoxic parenterally acceptable diluent or solvent (e.g., as a solution in 1,3-butanediol). Among the acceptable vehicles and solvents that can be employed are water, Ringer's solution, and isotonic sodium chloride solution. In addition, sterile, fixed oils are conventionally employed as a solvent or suspending medium. For this purpose any bland fixed oil can be employed including synthetic mono- or di-glycerides. In addition, fatty acids such as oleic acid can be used in the parenteral preparation.

Alternatively, compounds described herein can be formulated in powder form for constitution with a suitable vehicle, such as sterile pyrogen-free water, before use. For example, a compound suitable for parenteral administration can include a sterile isotonic saline solution containing between 0.1 percent and 90 percent weight per volume of the compound. By way of example, a solution can contain from about 5 percent to about 20 percent, from about 5 percent to about 17 percent, from about 8 to about 14 percent, and about 10 percent weight per volume of the compound. The solution or powder preparation can also include a solubilizing agent and a local anesthetic, such as lidocaine to ease pain at the site of the injection. Other methods of parenteral delivery of compounds will be known to the skilled artisan and are within the scope of the invention.

For oral administration, a compound described herein can be formulated to take the form of tablets or capsules prepared by conventional means with one or more pharmaceutically acceptable carriers (e.g., excipients such as binding agents, fillers, lubricants and disintegrants).

Controlled-release (or sustained-release) preparations can be formulated to extend the activity of a compound and reduce dosage frequency. Controlled-release preparations can also be used to effect the time of onset of action or other characteristics, such as blood levels of the compound, and consequently affect the occurrence of side effects.

Controlled-release preparations can be designed to initially release an amount of the compound to produce the desired therapeutic effect, and gradually and continually release other amounts of the compound to maintain the level of therapeutic effect over an extended period of time. In order to maintain a near-constant level of a compound in the body, the compound can be released from the dosage form at a rate that will replace the amount of compound being metabolized and/or excreted from the body. The controlled-release of a compound can be stimulated by various inducers, e.g., change in pH, change in temperature, enzymes, water, and/or other physiological conditions or molecules.

Controlled-release systems can include, for example, an infusion pump which can be used to administer the compound in a manner similar to that used for delivering chemotherapy to the body generally, or to specific organs or tumors. Typically, using such a system, the compound is administered in combination with a biodegradable, biocompatible polymeric implant that releases the compound over a controlled period of time at a selected site. Examples of polymeric materials include polyanhydrides, polyorthoesters, polyglycolic acid, polylactic acid, polyethylene vinyl acetate, and copolymers and combinations thereof. In addition, a controlled release system can be placed in proximity of a therapeutic target (e.g., organ, tissue, or group of cells), thus requiring only a fraction of a systemic dosage.

Compounds described herein can be administered by other controlled-release means or delivery devices that are well known to those of ordinary skill in the art. These include, for example, hydropropylmethyl cellulose, other polymer matrices, gels, permeable membranes, osmotic systems, multilayer coatings, microparticles, liposomes, microspheres, or the like, or a combination of any of the above to provide the desired release profile in varying proportions. Other methods of controlled-release delivery of compounds will be known to the skilled artisan and are within the scope of the invention.

Compounds described herein can be administered directly to the lung of a patient/subject by inhalation. For administration by inhalation, a compound can be conveniently delivered to the lung by a number of different devices. For example, a Metered Dose Inhaler ("MDI") which utilizes canisters that contain a suitable low boiling point propellant, e.g., dichlorodifluoromethane, trichlorofluoromethane, dichlorotetrafluoroethane, carbon dioxide or other suitable gas can be used to deliver a compound directly to the lung. MDI devices are available from a number of suppliers such as 3M Corporation, Aventis, Boehringer Ingleheim, Forest Laboratories, GlaxoSmithKline, Merck & Co. and Vectura.

Alternatively, a Dry Powder Inhaler (DPI) device can be used to administer a compound to the lung. DPI devices typically use a mechanism such as a burst of gas to create a cloud of dry powder inside a container, which can then be inhaled by the patient. DPI devices are also well known in the art and can be purchased from a number of vendors which include, for example, GlaxoSmithKline, Nektar Therapeutics, Innovata and Vectura. A popular variation is the multiple dose DPI ("MDDPI") system, which allows for the delivery of more than one therapeutic dose. MDDPI devices are available from companies such as AstraZeneca, GlaxoSmithKline, TEVA, Merck & Co., SkyePharma and Vectura. For example, capsules and cartridges of gelatin for use in an inhaler or insufflator can be formulated containing a powder mix of the compound and a suitable powder base such as lactose or starch for these systems.

Another type of device that can be used to deliver a compound to the lung is a liquid spray device supplied, for example, by Aradigm Corporation. Liquid spray systems use extremely small nozzle holes to aerosolize liquid compound formulations that can then be directly inhaled into the lung. For example, a nebulizer device can be used to deliver a compound to the lung. Nebulizers create aerosols from liquid compound formulations by using, for example, ultrasonic energy to form fine particles that can be readily inhaled. Examples of nebulizers include devices supplied by Aventis and Battelle.

Compounds described herein can be formulated as a depot preparation. Such long-acting formulations can be administered by implantation (e.g., subcutaneously or intramuscularly) or by intramuscular injection. Accordingly, the compound can be formulated with suitable polymeric or hydrophobic materials such as an emulsion in an acceptable oil or ion exchange resin, or as sparingly soluble derivatives such as a sparingly soluble salt. Other methods of depot delivery of compounds will be known to the skilled artisan and are within the scope of the invention.

For topical application, a compound can be combined with a pharmaceutically acceptable carrier so that an effective dosage is delivered, based on the desired activity ranging from an effective dosage, for example, of 1.0 µM to 1.0 mM. A topical formulation of the compound can be applied to the skin. The pharmaceutically acceptable carrier can be in the form of, for example, and not by way of limitation, an ointment, cream, gel, paste, foam, aerosol, suppository, pad or gelled stick.

A topical formulation can include a therapeutically effective amount of the compound in an acceptable excipient, such as buffered saline, mineral oil, vegetable oils such as corn or arachis oil, petroleum jelly, Miglyol 182, alcohol solutions, or liposomes or liposome-like products. Any of these formulations of such compounds can include preservatives, antioxidants, antibiotics, immunosuppressants, and other, biologically or pharmaceutically effective agents that do not exert a significant detrimental effect on the compound. Other methods of topical delivery of compounds will be known to the skilled artisan and are within the scope of the invention.

Various other delivery systems are known in the art and can be used to administer the compounds. Moreover, these and other delivery systems can be combined and/or modified to promote optimization of the administration of compounds. Exemplary formulations that include compounds are described elsewhere herein.

In some embodiments, the compounds can be administered to cancer cells, such as skin cancer cells (e.g., melanoma). Cancers that can be treated, prevented, or managed by methods employing the compounds described herein and pharmaceutical compositions thereof can include but are not limited: leukemias, such as but not limited to, acute leukemia, acute lymphocytic leukemia, acute myelocytic leukemias, such as, myeloblastic, promyelocytic, myelomonocytic, monocytic, and erythroleukemia leukemias and myelodysplastic syndrome; chronic leukemias, such as but not limited to, chronic myelocytic (granulocytic) leukemia, chronic lymphocytic leukemia, hairy cell leukemia; polycythemia vera; lymphomas such as but not limited to Hodgkin's disease, non-Hodgkin's disease; multiple myelomas such as but not limited to smoldering multiple myeloma, nonsecretory myeloma, osteosclerotic myeloma, plasma cell leukemia, solitary plasmacytoma and extramedullary plasmacytoma; Waldenstrom's macroglobulinemia; monoclonal gammopathy of undetermined significance; benign monoclonal gammopathy; heavy chain disease; bone and connective tissue sarcomas such as but not limited to bone sarcoma, osteosarcoma, chondrosarcoma, Ewing's sarcoma, malignant giant cell tumor, fibrosarcoma of bone, chordoma, periosteal sarcoma, soft-tissue sarcomas, angiosarcoma (hemangiosarcoma), fibrosarcoma, Kaposi's sarcoma, leiomyosarcoma, liposarcoma, lymphangiosarcoma, neurilemmoma, rhabdomyosarcoma, synovial sarcoma; brain tumors such as but not limited to, glioma, astrocytoma, brain stem glioma, ependymoma, oligodendroglioma, nonglial tumor, acoustic neurinoma, craniopharyngioma, medulloblastoma, meningioma, pineocytoma, pineoblastoma, primary brain lymphoma; breast cancer including but not limited to ductal carcinoma, adenocarcinoma, lobular (small cell) carcinoma, intraductal carcinoma, medullary breast cancer, mucinous breast cancer, tubular breast cancer, papillary breast cancer, Paget's disease, and inflammatory breast cancer; adrenal cancer such as but not limited to pheochromocytom and adrenocortical carcinoma; thyroid cancer such as but not limited to papillary or follicular thyroid cancer, medullary thyroid cancer and anaplastic thyroid cancer; pancreatic cancer such as but not limited to, insulinoma, gastrinoma, glucagonoma, vipoma, somatostatin-secreting tumor, and carcinoid or islet cell tumor; pituitary cancers such as but limited to Cushing's disease, prolactin-secreting tumor, acromegaly, and diabetes insipius; eye cancers such as but not limited to ocular melanoma such as iris melanoma, choroidal melanoma, and cilliary body melanoma, and retinoblastoma; vaginal cancers such as squamous cell carcinoma, adenocarcinoma, and melanoma; vulvar cancer such as squamous cell carcinoma, melanoma, adenocarcinoma, basal cell carcinoma, sarcoma, and Paget's disease; cervical cancers such as but not limited to, squamous cell carcinoma, and adenocarcinoma; uterine cancers such as but not limited to endometrial carcinoma and uterine sarcoma; ovarian cancers such as but not limited to, ovarian epithelial carcinoma, borderline tumor, germ cell tumor, and stromal tumor; esophageal cancers such as but not limited to, squamous cancer, adenocarcinoma, adenoid cystic carcinoma, mucoepidermoid carcinoma, adenosquamous carcinoma, sarcoma, melanoma, plasmacytoma, verrucous carcinoma, and oat cell (small cell) carcinoma; stomach cancers such as but not limited to, adenocarcinoma, fungating (polypoid), ulcerating, superficial spreading, diffusely spreading, malignant lymphoma, liposarcoma, fibrosarcoma, and carcinosarcoma; colon cancers; rectal cancers; liver cancers such as but not limited to hepatocellular carcinoma and hepatoblastoma; gallbladder cancers such as adenocarcinoma; cholangiocarcinomas such as but not limited to papillary, nodular, and diffuse; lung cancers such as non-small cell lung cancer, squamous cell carcinoma (epidermoid carcinoma), adenocarcinoma, large-cell carcinoma and small-cell lung cancer; testicular cancers such as but not limited to germinal tumor, seminoma, anaplastic, classic (typical), spermatocytic, nonseminoma, embryonal carcinoma, teratoma carcinoma, choriocarcinoma (yolk-sac tumor), prostate cancers such as but not limited to, prostatic intraepithelial neoplasia, adenocarcinoma, leiomyosarcoma, and rhabdomyosarcoma; penal cancers; oral cancers such as but not limited to squamous cell carcinoma; basal cancers; salivary gland cancers such as but not limited to adenocarcinoma, mucoepidermoid carcinoma, and adenoidcystic carcinoma; pharynx cancers such as but not limited to squamous cell cancer, and verrucous; skin cancers such as but not limited to, basal cell carcinoma, squamous cell carcinoma and melanoma, superficial spreading melanoma, nodular melanoma, lentigo malignant melanoma, acral lentiginous melanoma; kidney cancers such as but not limited to renal cell carcinoma, adenocarcinoma, hypernephroma, fibrosarcoma, transitional cell cancer (renal pelvis and/or uterer); Wilms' tumor; bladder cancers such as but not limited to transitional cell carcinoma, squamous cell cancer, adenocarcinoma, carcinosarcoma. In addition, cancers include myxosarcoma, osteogenic sarcoma, endotheliosarcoma, lymphangioendotheliosarcoma, mesothelioma, synovioma, hemangioblastoma, epithelial carcinoma, cystadenocarcinoma, bronchogenic carcinoma, sweat gland carcinoma, sebaceous gland carcinoma, papillary carcinoma and papillary adenocarcinomas (for a review of such disorders, see Fishman et al., 1985, Medicine, 2d Ed., J. B. Lippincott Co., Philadelphia and Murphy et al., 1997, Informed Decisions: The Complete Book of Cancer Diagnosis, Treatment, and Recovery, Viking Penguin, Penguin Books U.S.A., Inc., United States of America)

Accordingly, therapeutic methods employing the compounds described herein are useful in the treatment or prevention of a variety of cancers or other abnormal proliferative diseases, including (but not limited to) the following: carcinoma, including that of the bladder, breast, prostate, rectal, colon, kidney, liver, lung, ovary, pancreas, stomach, cervix, thyroid and skin; including squamous cell carcinoma; hematopoietic tumors of lymphoid lineage, including leukemia, acute lymphocytic leukemia, acute lymphoblastic leukemia, B-cell lymphoma, T-cell lymphoma, Burkitt's lymphoma; hematopoictic tumors of myeloid lineage, including acute and chronic myelogenous leukemias and promyclocytic leukemia; tumors of mesenchymal origin, including fibrosarcoma and rhabdomyoscarcoma; other tumors, including melanoma, seminoma, tetratocarcinoma, neuroblastoma and glioma; tumors of the central and peripheral nervous system, including astrocytoma, neuroblastoma, glioma, and schwannomas; tumors of mesenchymal origin, including fibrosarcoma, rhabdomyoscarama, and osteosarcoma; and other tumors, including melanoma, xeroderma pigmentosum, keratoactanthoma, seminoma, thyroid follicular cancer and teratocarcinoma. It is also contemplated that cancers caused by aberrations in apoptosis would also be treated by the methods and compositions of the invention. Such cancers may include but not be limited to follicular lymphomas, carcinomas with p53 mutations, hormone dependent tumors of the breast, prostate and ovary, and precancerous lesions such as familial adenomatous polyposis, and myelodysplastic syndromes. In specific embodiments, malignancy or dysproliferative changes (such as metaplasias and dysplasias), or hyperproliferative disorders, are treated or prevented in the skin, lung, colon, rectum, breast, prostate, bladder, kidney, pancreas, ovary, or uterus. In other specific embodiments, sarcoma, melanoma, or leukemia is treated or prevented.

In certain embodiments, the compounds described herein can be delivered to cancer cells by site-specific means. Cell-type-specific delivery can be provided by conjugating the compounds to a targeting molecule, for example, one that selectively binds to the affected cells. Methods for targeting include conjugates, such as those described in U.S. Pat. No. 5,391,723. Targeting vehicles, such as liposomes, can be used to deliver a compound, for example, by encapsulating the compound in a liposome containing a cell-specific targeting molecule. Methods for targeted delivery of compound to particular cell types are well-known to those skilled in the art.

In some embodiments, the compounds described herein can be used in combination and adjunctive therapies for treating cancer. The phrase "combination therapy" embraces the administration of the compositions described herein and an additional therapeutic agent as part of a specific treatment regimen intended to provide a beneficial effect from the co-action of these therapeutic agents. Administration of these compounds described herein in combination typically is carried out over a defined time period (usually minutes, hours, days or weeks depending upon the combination selected).

A combination therapy is intended to embrace administration of the compounds described herein in a sequential manner, that is, wherein different therapeutic agents are administered at a different time, as well as administration of the compounds described herein, or at least two of the therapeutic agents, in a substantially simultaneous manner. Substantially simultaneous administration can be accomplished, for example, by administering to the subject a single capsule having a fixed ratio of each therapeutic agent or in multiple, single capsules for each of the therapeutic agents. Sequential or substantially simultaneous administration of therapeutic agents can be effected by an appropriate routes including, but not limited to, oral routes, intravenous routes, intramuscular routes, and direct absorption through mucous membrane tissues. The therapeutic agents can be administered by the same route or by different routes. The sequence in which the therapeutic agents are administered is not narrowly critical.

Combination therapy also can embrace the administration of the compounds in further combination with other biologically active ingredients (such as, but not limited to, a second and different therapeutic agent) and non-drug therapies (such as, but not limited to, surgery or radiation treatment). Where the combination therapy further comprises radiation treatment, the radiation treatment may be conducted at a suitable time so long as a beneficial effect from the co-action of the combination of the compounds and radiation treatment is achieved. For example, in appropriate cases, the beneficial effect is still achieved when the radiation treatment is temporally removed from the administration of the therapeutic agents, perhaps by days or even weeks.

In some embodiments, the compounds described herein can be administered in combination with an anti-proliferative agent or anti-cancer agent. The phrase "anti-proliferative agent" and "anti-cancer agent" can include agents that exert antineoplastic, chemotherapeutic, antiviral, antimitotic, antitumorgenic, and/or immunotherapeutic effects, e.g., prevent the development, maturation, or spread of neoplastic cells, directly on the tumor cell, e.g., by cytostatic or cytocidal effects, and not indirectly through mechanisms, such as biological response modification. There are large numbers of anti-proliferative agents available in commercial use, in clinical evaluation and in pre-clinical development, which can be included in this application by combination drug chemotherapy. Examples of anti-proliferative agents are ACE inhibitors, alkylating agents, angiogenesis inhibitors, angiostatin, anthracyclines/DNA intercalators, anti-cancer antibiotics or antibiotic-type agents, antimetabolites, antimetastatic compounds, asparaginases, bisphosphonates, cGMP phosphodiesterase inhibitors, calcium carbonate, cyclooxygenase-2 inhibitors, DHA derivatives, DNA topoisomerase, endostatin, epipodophylotoxins, genistein, hormonal anticancer agents, hydrophilic bile acids (URSO), immunomodulators or immunological agents, integrin antagonists, interferon antagonists or agents, MMP inhibitors, miscellaneous antineoplastic agents, monoclonal antibodies, nitrosoureas, NSAIDs, ornithine decarboxylase inhibitors, pBATTs, radio/chemo sensitizers/protectors, retinoids, selective inhibitors of proliferation and migration of endothelial cells, selenium, stromelysin inhibitors, taxanes, vaccines, and vinca alkaloids.

The major categories that some anti-proliferative agents fall into include antimetabolite agents, alkylating agents, antibiotic-type agents, hormonal anticancer agents, immunological agents, interferon-type agents, and a category of miscellaneous antineoplastic agents. Some anti-proliferative agents operate through multiple or unknown mechanisms and can thus be classified into more than one category.

In certain embodiments, the compounds can be administered with an anti-cancer agent that induces stress in the cancer cells. The stress applied to the cancer cell can include, for example, radiation therapy or ionizing radiation, thermal stress or thermal therapy, irreversible electroporation (IRE), and oxidative stress.

Radiation therapy may include both "sealed" and "unsealed" sources of therapeutic radiation including, but not limited to, ionizing radiation therapy, brachytherapy, sealed source radiation therapy, systemic radioisotope therapy, unsealed source radiotherapy, radionuclide therapy, external beam radiation therapy, radiation surgery, charged-particle radiotherapy, neutron radiotherapy, x-ray therapy, and cobalt therapy.

Thermal stress or therapy can include focused ultrasound (FUS or HIFU), radiofrequency, infrared sauna, microwave heating, induction heating, magnetic hyperthermia, infusion of warmed liquids, or direct application of heat. The thermal stress can include local hyperthermia and/or regional hyperthermia. The thermal stress or thermal therapy can also include exposure to sub-lethal heat. For example, a hyperthermia modality may heat a cancer cell too much lower therapeutic temperatures (in general <45° C.) compared to other tissue ablation techniques. For instance, the elevation above a normal body temperature of 37° C. typically will fall within a range of 42° C. to 45° C.

Irreversible electroporation uses a series of microsecond electrical pulses instead of extreme heat, freezing, radiation or microwave energy—to permanently open cell membranes in cancerous tumors. Once the cell membrane pores are opened, the death of the targeted cancer cells is induced. Surrounding veins, nerves and ducts within the targeted area are largely unaffected by the process around them, providing a compelling tool for procedures in difficult-to-treat parts of the body.

The exposure to stress may also be imaged guided. For example, clinical HIFU procedures are typically image-guided to permit treatment planning and targeting before applying a therapeutic or ablative level of ultrasound energy. When MRI is used for guidance, the technique is sometimes called Magnetic Resonance-guided Focused Ultrasound, often shortened to MRgFU. When ultrasonography is used, the technique is sometimes called Ultrasound-guided Focused Ultrasound, often shortened to USgFUS.

A subject having cancer, tumor, or at least one cancer or tumor cell, may be identified using methods known in the art. For example, the anatomical position, gross size, and/or cellular composition of cancer cells or a tumor may be determined using contrast-enhanced MRI or CT. Additional methods for identifying cancer cells can include, but are not limited to, ultrasound, bone scan, surgical biopsy, and biological markers (e.g., serum protein levels and gene expression profiles). An imaging solution comprising a cell-sensitizing composition of the present invention may be used in combination with MRI or CT, for example, to identify cancer cells.

The location(s) where compounds administered to the subject may be determined based on the subject's individual need, such as the location of the cancer cells (e.g., the position of a tumor, the size of a tumor, and the location of a tumor on or near a particular organ). For example, the composition may be injected directly (i.e., intratumorally) into a tumor. Alternatively, the compounds may be injected intravenously into the subject. It will be appreciated that other routes of injection may be used including, for example, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal routes.

Cancer therapies and their dosages, routes of administration and recommended usage are known in the art and have been described in such literature as the Physician's Desk Reference (56th ed., 2002).

As can be appreciated from the disclosure above, the present invention has a wide variety of applications. The invention is further illustrated by the following examples, which are only illustrative and are not intended to limit the definition and scope of the invention in any way.

Example 1

In this Example, we investigated the photophysical properties of the thiobase series 2-thiothymine (2tThy), 2-thiothymidine (2tThd), 4-thiothymidine (4tThd), and 2,4-dithiothymine (2,4dtThy) and compare them to those recently reported for thymidine (Thd), 2tThy/2tThd, and 4tThd. We determined: (1) how the site and degree of sulfur substitution affects the photosensitization properties of this series (shown in FIG. 1A), and (2) measured quantitative yields of singlet oxygen in order to scrutinize their prospective use as photochemotherapeutic agents.

Materials and Methods
Materials and Steady-State Spectroscopy 2-thiothymine (2tThy, 98% purity) was obtained from AK Scientific, 4-thiothymidine (4tThd, 99% purity) was obtained from Carbosynth Ltd., and 2-thiothymidine (2tThd) and 2,4-dithiothymine (2,4dtThy) were obtained from Sigma Aldrich. All compounds were used as received. The purity of these compounds was ensured by using fluorescence spectroscopy and by comparison with the published absorption maxima and their corresponding extinction coefficients. Phosphate buffer solutions were freshly prepared using 0.12 g of sodium dihydrogen phosphate and 0.089 g of disodium hydrogen phosphate dissolved in 100 mL of ultrapure water and adjusted to pH 7.4 using a 2 M NaOH solution. Steady-state absorption spectra were measured using a Cary 100 Bio spectrometer. All absorption spectra were corrected for the solvent background by subtraction of the absorption of the solvent.

Transient Absorption Spectroscopy

Femtosecond transient absorption spectroscopy was performed using a Ti— Sapphire regenerative amplifier laser system (Libra-HE, Coherent, Inc.; 800 nm, 100 fs, 4.0 W at 1 kHz). 2.6 W of the 800 nm beam were used to pump an optical parametric amplifier (TOPAS, Quantronix/Light Conversion) to generate the excitation beam at selected wavelengths of 320, 335, and 360 nm. Contributions to the excitation beam from other wavelengths and polarizations were removed by a reflective wavelength filter (λ-filter) and a Glan-Taylor polarizer, respectively, and the polarization was randomized using a depolarizing plate in order to prevent rotational effects from contributing to the dynamics, as described in details elsewhere.

A Helios spectrometer (Ultrafast Systems, LLC.) was used for pump-probe measurements. A fraction of the fundamental (800 nm) beam from the Libra-HE was used to generate white light continuum (WLC). The Helios spectrometer uses an optical delay line with a maximum delay of ~3 ns for the 800 nm beam, which was used to pump a continuously-moving 2 mm CaF2 plate for generation of the WLC broadband probe pulse covering the spectral range from ~320-700 nm. The probe light was then passed through a 730 nm low-pass dichroic optical filter, so as to block residual fundamental beam and to avoid saturating the complementary metal-oxide-semiconductor (CMOS) detectors. The probe pulse was then split into two beams, both of which were recollimated and focused into the optical fibers leading to their respective CMOS detectors. In this setup, one of the beams serves as reference, while the other is used to probe the sample of interest. A synchronized chopper wheel was used to block every other pump pulse, such that the difference in absorption between two consecutive measurements gives the transient spectrum. The excitation beam was attenuated to 1 µJ/pulse at the sample using a neutral density optical filter before entering the spectrometer. The excitation pulse was focused to a beam diameter three times larger than that of the probe beam at the sample position. Detection time windows of 20 and 200 ps were used in this work.

All solutions were prepared using pH 7.4 aqueous phosphate buffer, with a total phosphate concentration of 16 mM. The solution was continuously stirred in a 2 mm optical path length quartz cell (Starna Cells, Inc.) using a Teflon-coated magnetic stirring bar so as to bring fresh sample to the pump-probe region for each measurement. The solution in the cuvette was replaced with a fresh sample, from the same stock solution, every 5-7 scans, so that all scans had no more than 5% decrease in absorbance at the lowest-energy absorption-band maximum as determined by steady-state absorption spectroscopy. Importantly, individual scans showed no evidence of photoproduct(s) contamination under the experimental conditions used.

Transient Absorption Data Analysis

All broadband transient absorption data were corrected for group velocity dispersion (GVD) of the WLC using a home-made LabView program (National Instruments, Inc.) as previously described. 3 Analysis of transient absorption kinetics was performed in Igor Pro 6.32A (WaveMetrics, Inc.) using the target analysis method, as described previously, and a sequential kinetic model convoluted with an instrument response function of ~200 fs (FWHM). The instrument response was determined from the coherence signal of neat methanol generated at the sample cell. Global fitting analysis was performed using 15 to 30 representative kinetic traces covering the full range of probe wavelengths. At least three independent datasets (i.e., recorded on three different days) were used in the analysis and all uncertainties are reported as twice the standard deviation of the average lifetime. Decay associated spectra shown in FIG. 7A were extracted from the global fitting analysis of the transient decay traces taken every third probe wavelength across the entire WLC range.

Singlet Oxygen Quantum Yields

Singlet oxygen phosphorescence measurements were performed using a modified Fluorolog-3 spectrometer (HORIBA, Jobin Yvon) in conjunction with a NIR sensitive photomultiplier tube (H10330A-45, Hamamatsu). A 450 W Xe lamp was used for steady state excitation to record singlet oxygen phosphorescence spectra and a Spectra Physics GCR-150-30 Nd:YAG laser (355 nm, 7 ns pulse width) was used for pulsed excitation to collect singlet oxygen phosphorescence decay traces at 1270 nm, which were stored on a digital oscilloscope (TDS 360, Tektronics).

$O_2$-saturated acetonitrile solutions of the thiobases and standard (phenalenone) with matching absorbance at 355 nm (O.D.=0.3 at 1 cm optical path length) were prepared. The measurements were performed in a 1×1 cm quartz cell. Singlet oxygen quantum yields were determined from the phosphorescence intensity at 1270 nm at the end of the laser pulse using phenalenone as standard ($\Phi_\Delta$=0.98).

Results

FIG. 1b shows that the site and degree of sulfur substitution have striking effects on the absorption spectra of the thiobases, both within the series and compared to the absorption spectrum of the canonical DNA base. Specifically, sulfur substitution of the C2 carbonyl in thymine results in about a 10 nm redshift in the absorption maximum, whereas substitution at the C4 position results in a redshift of about 70 nm. Remarkably, double-substitution results in about a 100 nm redshift of the lowest-energy absorption band of thymidine ($\Delta E$=9905 cm$^{-1}$), without an appreciable change in the magnitude of the extinction coefficient at the corresponding wavelengths ($1 \times 10^4$ M$^{-1}$ cm$^{-1}$). Replacement of an oxygen atom by a sulfur atom in a carbonyl bond is expected to shift the absorption spectrum to the red because the thiocarbonyl is weaker than the carbonyl bond and the excited electronic states in thiocarbonyl compounds are typically found at lower energies. However, the difference in bond strengths between a carbonyl and thiocarbonyl bond cannot solely explain the large spectral shift observed between 2tThy/2tThd and 4tThd. Furthermore, the redshift in the absorption spectrum of 2,4dtThy cannot simply be expressed as a linear combination of the absorption spectra of the 2tThy/2tThd and 4tThd derivatives. In addition, these large spectral shifts do not arise from the presence or absence of a sugar at the N1 position of the thiothymine chromophore. Glycosylation of 2tThy, generating 2tThd, results in a 2 nm redshift in the absorption maximum and about 2-fold increase in the molar absorptivity coefficients (FIG. 1B). The same effect has been previously documented in the natural bases and in other thiobases. Therefore, glycosylation of 2,4dtThy to form 2,4-dithiothymidine is expected to redshift the absorption spectrum slightly and to increase the molar absorptivity coefficients.

Femtosecond broad-band transient absorption spectroscopy was employed to further investigate the effect that varying the degree and position of sulfur substitution has on the electronic properties of these thiothymine derivatives. Solutions were continuously stirred to replenish the excited-state volume and replaced with fresh solutions as necessary to ensure no contamination of the transient absorption data by photoproducts. The focus of this set of experiments was to measure the intersystem crossing rate and to determine the relative triplet yields for the thiothymine series from back-to-back experiments (Table 1). As observed previously for 2tThy/2tThd19,20 and 4tThd,14,16 the excited triplet state of 2,4dtThy can be probed selectively at wavelengths longer than 500 nm (FIG. 2A). Representative growth traces are shown in FIG. 2B. These traces were taken at 600 nm probe wavelength and show that the triplet state is populated on the femtosecond time scale in all four thiothymine derivatives of this series. Glycosylation of 2tThy shortens the intersystem crossing lifetime from about 620 to 410 fs. Furthermore, FIG. 2 and Table 1 show that 2,4dtThy has the shortest intersystem crossing lifetime of the series, which is in fact the fastest rate of intersystem crossing measured for any thiobase derivative to date.

TABLE 1

Triplet-State Properties and Singlet Oxygen Yields of Thymidine and Its Sulfur-Substituted Analogues

|  | $\tau_{ISC}{}^a$ (fs) | $\Phi_T{}^b$ | $\Phi_\Delta{}^c$ |
|---|---|---|---|
| Thd | 760 | 0.014 ± 0.001 | 0.07 ± 0.01 |
| 2tThy | 620 ± 60 | 0.9 ± 0.1 | 0.36 ± 0.02 |
| 2tThd | 410 ± 60 | 0.9 ± 0.1 |  |
| 4tThd | 240 ± 20 | 0.85 ± 0.15 | 0.42 ± 0.02 |
| 2,4dtThy | 180 ± 40 | >0.9 | 0.46 ± 0.02 |

$^a$Intersystem crossing lifetimes and
$^b$triplet quantum yields in pH 7.4 phosphate buffer solution.
$^c$Singlet oxygen quantum yields in $O_2$-saturated acetonitrile solution.

Comparison of the triplet-state dynamics of this series to the dynamics of the parent thymine nucleoside indicates that ultrafast intersystem crossing is an intrinsic property of the thymine monomer, and possibly of pyrimidines in general, rather than explicitly the result of sulfur substitution. However, the results presented in Table 1 demonstrate that sulfur substitution does greatly enhance intersystem crossing from being a minor relaxation pathway in thymidine, to being the overwhelmingly primary mode of relaxation in these thiothymine derivatives, independent of the site or the degree of sulfur substitution. The transient absorption results support the idea that the triplet yield of 2,4dtThy is equal to or higher than those previously reported for 2tThy/2tThd and 4tThd under similar experimental conditions. This is further supported by the shorter intersystem crossing lifetime of 2,4dtThy, indicating a higher probability for population transfer to the triplet manifold. The sub-200 fs population of the triplet state and its near-unity yield suggest that the spin-orbit and vibronic coupling interactions in 2,4dtThy are close to saturation because of the addition of a second sulfur substituent to the thiothymine base. Hence, intersystem crossing occurs in the strongly non-adiabatic regime between non-equilibrated excited states, where the ability of active vibrational modes in the singlet manifold to couple and explore the singlet-triplet crossing regions may control the intersystem crossing rates in this important series of biomolecules.

Figure 4:
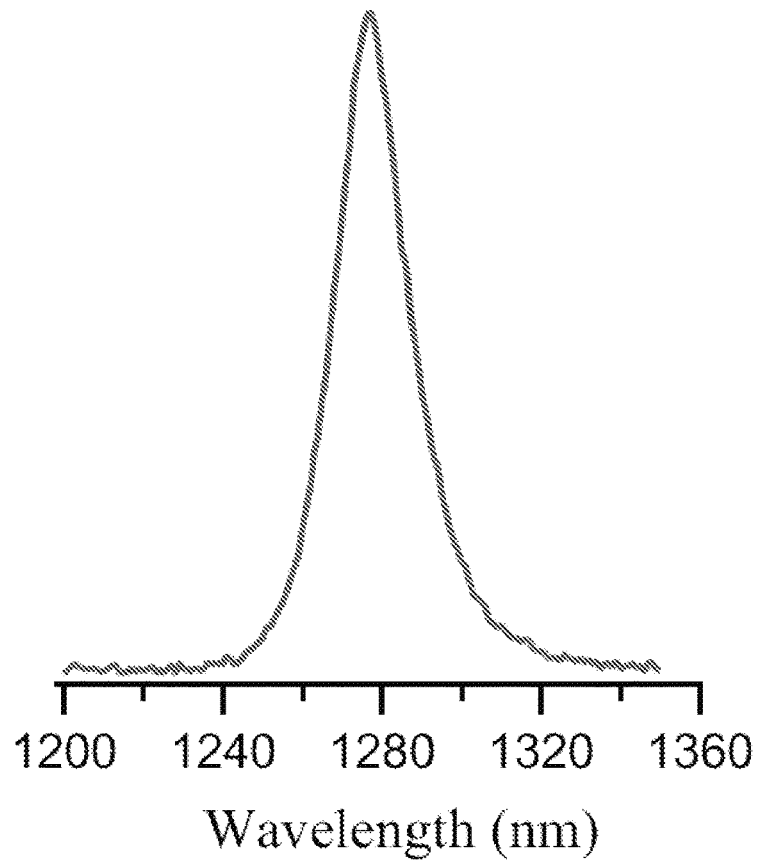
FIG. 4 illustrates a plot showing singlet oxygen phosphorescence spectrum generated by photo-excitation at 355 nm of 4tThd in $O_2$-saturated acetonitrile solution.

While ultrafast internal conversion to the ground state and the low triplet yield in thymidine provide the nucleobase with its high degree of photostability, the near-unity triplet yields in the thiothymine series account for their potent photo-sensitization properties. We have obtained evidence for significant photoreactivity of these triplet states by performing time-resolved energy transfer experiments to molecular oxygen, thus generating singlet oxygen, as monitored by its characteristic phosphorescence at 1270 nm (FIG. 3 and FIG. 4). The singlet oxygen quantum yields for 4tThd and 2,4dtThy were determined using phenalenone as a standard ($\Phi_\Delta$=0.98) and are summarized in Table 1. It should be remarked that quantification of the singlet oxygen yield is one of the primary methods used to determine the efficacy of a prospective photosensitizer for phototherapeutic applications. To our knowledge, this is the first work to report the singlet oxygen yield of 2,4dtThy. Although, we did not measure the singlet oxygen yield of 2tThy or 2tThd because of the limited UVA absorption of these thiobase derivatives, the singlet oxygen yield of 2tThy was previously measured in acetonitrile under $O_2$-saturated conditions. Consistent with the spectroscopic analysis herein, the singlet oxygen yield of 2tThy is smaller than those of 4tThd and 2,4dtThy.

Importantly, it has been shown that 4tThd in conjunction with a low dose of UVA radiation can effectively kill cancerous cell lines in vitro, treat bladder cancer in animal models, and induce cytotoxic lesions in the lower epidermis of 3D human skin models. However, 4tThd exhibits limited absorption of near-visible UVA radiation, which has raised concerns as to the practicality of this thiobase in clinical applications. We show that 2,4dtThy has the potential to act as a more effective deep-tissue UVA photosensitizer than 4tThd because of its higher rate of intersystem crossing and increased propensity to generate singlet oxygen, in addition to its ability to absorb UVA radiation more strongly near the visible region of the spectrum, as shown in FIG. 1B.

Figure 5:
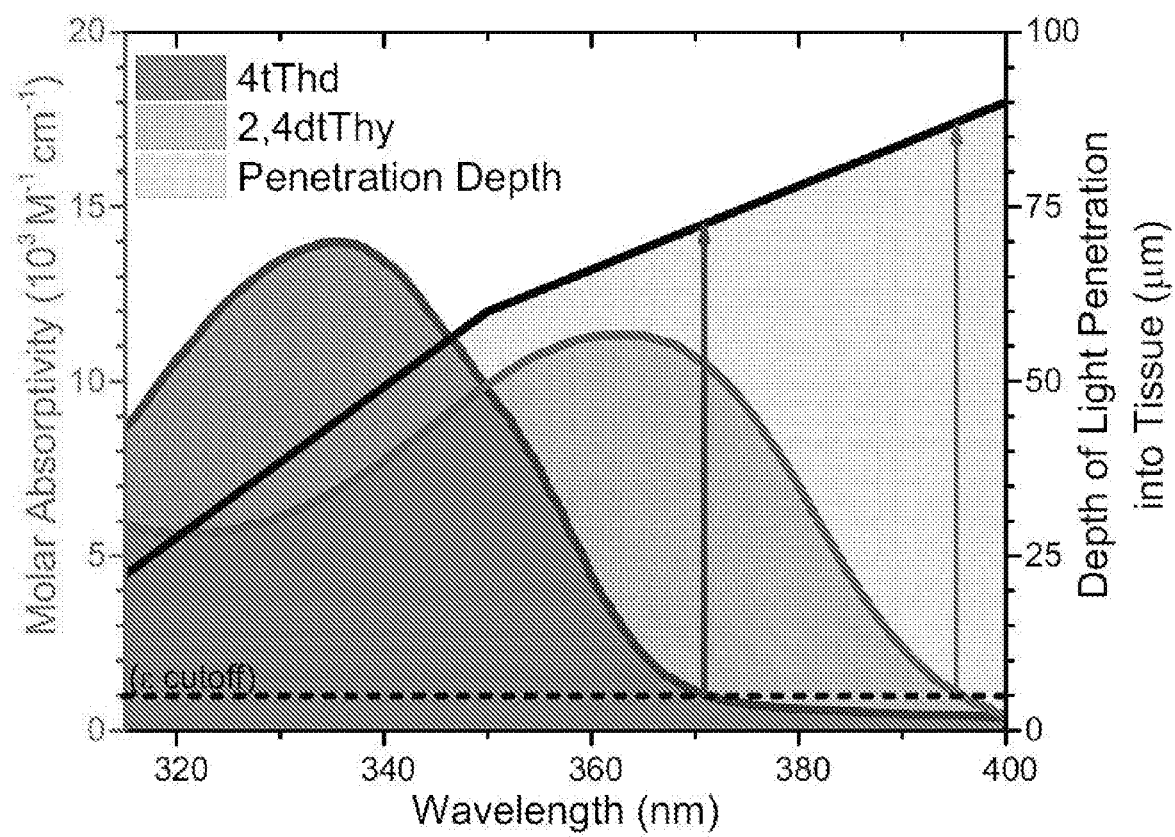
FIG. 5 illustrates a plot showing molar absorptivity coefficients of 4tThd and 2,4dtThy in the UVA region of the spectrum overlaid with the wavelength-dependent penetration depth of UVA light into tissue.

Longer wavelengths of light are able to penetrate deeper into tissues due to less scattering and reduced absorption by natural biomolecules (FIG. 5). Therefore, the redshifted absorption of 2,4dtThy as compared to 4tThd opens up the possibility for it to be effectively used as a photosensitizer in deeper tissue UVA-activated therapies. The maximum treatment depth for these two compounds was estimated by defining an arbitrary absorption cutoff of $\varepsilon$=1000 $M^{-1}$ $cm^{-1}$ (i.e., 371 nm for 4tThd and 395 nm for 2,4dtThy; FIG. 5). This revealed treatment depths of 71 and 87 μm, respectively, corresponding to a lower bound of approximately 23% increase in the maximum treatment depth of 2,4dtThy as compared to 4tThd. This simple method, however, does not provide the total relative increase in treatment depth because it does not take into account the wavelength dependency of the penetration depth across the entire UVA range (315-400 nm). In order to account for this, the area under the penetration depth curve (FIG. 5) was integrated up to the respective absorption cutoff for each compound. Using this integration method the total increase in treatment depth of 2,4dtThy relative to 4tThd was determined to be about 67%. This increase likely serves as an upper bound limit for the actual relative increase because the molar absorptivity coefficients of the compounds will no doubt play a role. However, because the absorption of radiation at a given wavelength is not only dependent on a photosensitizer's molar absorptivity coefficients but also on its concentration in the tissue, our best estimation is that 2,4dtThy could facilitate UVA-activated treatment in tissues 23 to 67% deeper than those that can be effectively treated by 4tThd.

In summary, we have shown that the site and degree of sulfur substitution have significant effects on the photophysical and photodynamic properties of the 2tThy, 2tThd, 4tThd, and 2,4dtThy series. Surprisingly, the degree and position at which the sulfur atom is substituted play key roles in the magnitude of the intersystem crossing rate constant, showing a 1.2-, 3.2-, and 4.2-fold rate increase for 2tThy, 4tThd, and 2,4dtThy, respectively, relative to that of Thd. It appears that glycosylation also enhances the intersystem crossing rate in this series, at least for the 2tThy/2tThd pair. This paradigm is further highlighted by comparing the photophysical properties of this series to those of the natural thymidine monomer. The lowest-energy absorption band shifts from a maximum at ~267 nm ($\varepsilon \approx 9.9 \times 10^3$ $M^{-1}$ $cm^{-1}$) in Thd to 363 nm ($\varepsilon \approx 9.7 \times 10^3$ $M^{-1}$ $cm^{-1}$) in 2,4dtThy. The triplet and singlet oxygen yields increase from 1.4% and 7% in Thd, respectively, to approximately 90% and 50% in 2,4dtThy. A single sulfur atom substitution leads to near-unity triplet yields in this series, as observed in other thiobases.

Of paramount relevance for photochemotherapeutic applications, we have shown that, from this series, 2,4dtThy fulfills three of the most basic requirements of a potent UVA sensitizer: (1) strong absorption cross sections in the UVA spectral region, (2) near-unity triplet yields, and (3) high yields of singlet oxygen generation. On the basis of these photophysical properties, we show that 2,4dtThy can outperform 2tThd and 4tThd for deeper-tissue UVA chemotherapies.

Example 2

We investigated the thio-RNA series 2-thiouracil (2tUra), 4-thiouracil (4tUra), and 2,4-dithiouracil (2,4dtUra) under equal experimental conditions (FIG. 6). From a fundamental perspective, the detailed set of experiments provide important, insights into the structural and electronic factors that control the photoreactivity and photosensitizing efficacy of this thio-RNA series. From an application-based standpoint, our results reveal that 2,4dtUra has the highest photosensitizing and photoreactivity efficacy when compared side-by-side to the widely used 4tUra. More importantly, 2,4dtUra provides a basis for developing novel RNA-targeting phototherapeutic agents, which can find applications in clinical settings.

EXPERIMENTAL

Chemicals

2-Thiouracil (2tUra, ≥99% purity), 4-thiouracil (4tUra, 97% purity), 2,4-dithiouracil (2,4dtUra, 98% purity), and adenosine 5'-monophosphate (5'-AMP, ≥99% purity) were obtained from Sigma-Aldrich and used as received. Phenalenone (97% purity) was also from Sigma-Aldrich and purified by recrystallization from ethanol. Aqueous phosphate-buffered saline solutions were freshly prepared in 100 mL of ultrapure water at pH 7.4 (0.12 g of sodium dihydrogen phosphate and 0.089 g of disodium hydrogen phosphate) and pH 5.4 (0.185 g of sodium dihydrogen phosphate and 0.009 g of disodium hydrogen phosphate). Solutions were adjusted to their specified pH by drop-wise addition of 2 M aqueous NaOH. Acetonitrile (≥99.9% purity) was obtained from Fisher Scientific and used as received.

Steady-State Spectroscopy

Steady-state absorption spectra were measured using a Cary 100 Bio spectrometer. All absorption spectra were background corrected by subtracting the absorption of the neat solvent. Molar absorptivity coefficients were determined from the absorption spectra of serial dilutions of stock solutions with known concentrations.

Transient Absorption Spectroscopy

A detailed description of the transient absorption instrumentation used in this work has been described previously. Briefly, 800 nm, 100 fs fundamental pulses were generated with a Ti-Sapphire regenerative amplifier laser system (Libra-HE, Coherent, Inc.: 4.0 W, 1 kHz). The fundamental beam was used to produce pump wavelengths of 320, 335, and 350 nm via an optical parametric amplifier (TOPAS, Quantronix/Light Conversion). Unwanted wavelengths were removed from the pump beam using a reflective wavelength filter and a Glan-Taylor polarizer. A fraction of the remaining fundamental beam was focused into a continuously moving CaF2 plate (2 mm thick) to generate broadband white light probe pulses (320-700 nm). The intensity of the excitation beam was attenuated to 1 mJ per pulse at the sample position. The polarization of the pump beam was randomized before being focused into the sample to overlap with the white light continuum probe at a 3:1 beam diameter ratio. Pump-probe experiments were collected using a Helios spectrometer (Ultrafast Systems, LLC) and a home-made data acquisition software (LabView, National Instruments, Inc.).

Solutions of the 2tUra, 4tUra, and 2,4dtUra derivatives were prepared in aqueous phosphate-buffered saline at pH 7.4. In the case of 2,4dtUra, solutions were also prepared at pH 5.4 due to its lower pKa (7.4) as compared to those of 2tUra (7.74) and 4tUra (8.0). The absorption spectrum of the excited deprotonated species of 2,4dtUra contributed slightly to the transient absorption spectra observed at pH 7.4. However, the intersystem crossing lifetime of 2,4dtUra at both pHs was identical within experimental uncertainties (220±40 vs. 210±50 fs). Solutions were investigated in 2 mm optical path length quartz cells and the irradiated volume was continuously refreshed by stirring with a Teflon-coated magnetic stir bar. Contributions to the transient data from any putative photoproduct formation were prevented by replacing the solution with fresh stock solution every 5 scans, or before 6% sample degradation (as monitored by a decrease in the steady-state absorbance of the lowest-energy absorption band). The UVA excitation wavelength used was varied depending on the absorption spectrum of the specific thiouracil derivative investigated. For 2tUra, an excitation wavelength of 320 nm was used, whereas 2,4dtUra was excited at 335 and 350 nm, and 4tUra was excited at all three of these UVA wavelengths. The dynamics did not display any excitation wavelength dependence in this range.

Decay of the triplet state of 4tUra and 2,4dtUra to the ground state was monitored using the same excitation and detection setups but probing with an electronically triggered broadband white light source (Eos, Ultrafast Systems, LLC) that has been conveniently integrated into the Helios spectrometer. This probe source has a spectral window from B375 to 800 nm, a time resolution of about 400 ps, and a temporal window of up to 120 ms. Aqueous buffer solutions of each thiouracil derivative were prepared at 24 µM in 1 cm path length septum-topped cuvettes and purged with ultrapure nitrogen for 30 min prior to testing. Data were collected with the solutions under a constant nitrogen flow, and exciting at 350 nm with 3 mJ per pulse for 10 min, corresponding to less than 5% degradation.

Transient Absorption Data Analysis

A home-made LabView program (National Instruments, Inc.) was used to correct all transient absorption data for group velocity dispersion of the white light probe, as described in detail elsewhere. For each data set, between 50 and 100 traces were selected across the entire range of probe wavelengths and globally analyzed in Igor Pro 6.32A (WaveMetrics, Inc.). Specifically, data sets for all thiouracil derivatives fit well to a sequential kinetic model, which was convoluted with an instrument response function of B200 fs (FWHM), as determined by the coherence signal of methanol at the sample position. 83 The uncertainties reported for the triplet population lifetimes are twice the standard deviation from the average fitting of at least three independent datasets (i.e., recorded on three different days). Triplet-triplet absorption spectra were extracted from the global fitting analysis.

Determination of the Triplet-Triplet Extinction Coefficients and Triplet Yields

The extinction coefficients for the triplet-triplet absorption bands of 4tUra and 2,4dtUra were determined using the singlet depletion method. This method is convenient for the thiobases, as previously shown for 4-thiothymidine 85 and 6-thioguanosine, because the bleaching signal can be selectively probed for both compounds within our probe wavelength range. Under these experimental conditions, the excited triplet state concentration, $[^3M^*]$, at any given delay time can be obtained using eqn (1), where $\Delta A_{GS}(\lambda_1)$ is the intensity of the ground state bleaching signal at $\lambda_1$, $\varepsilon_{GS}(\lambda_1)$ is the molar absorptivity of the ground state absorption at $\lambda_1$, and l is the path length of the cuvette (0.2 cm).

$$\Delta A_{GS}(\lambda_1) = -\varepsilon_{GS}(\lambda_1)[^3M^*]l \qquad (1)$$

Eqn (2) can then be used to determine the triplet-triplet extinction coefficient, $\varepsilon_{T-T}*(\lambda_2)$, at $\lambda_2$ using $[_3M^*]$ from eqn (1) and the absorption intensity of the triplet band at 2, $\Delta A_T(\lambda_1)$. The wavelength of triplet-triplet absorption, $\lambda_2$, must be well-separated from the ground state bleaching signal.

$$\Delta A_{GS}(\lambda 2) = -\varepsilon_{T-T}*(\lambda 2)[^3M^*]l \qquad (2)$$

Using the singlet depletion method, the triplet-triplet extinction coefficients of 4tUra and 2,4dtUra were determined to be 3000±600 M$^{-1}$ cm$^{-1}$ and 2500±600 M$^{-1}$ cm$^{-1}$ at 600 nm, respectively. With these $\varepsilon_{T-T}*$ values, the triplet quantum yields can be determined using the relative actinometry method and eqn (3).

$$\Phi_T(U) = \frac{\Delta A_U(\lambda 4) \Phi_T(R) \varepsilon_R *(\lambda 3)^l}{\Delta A_R(\lambda 3) \varepsilon_U *(\lambda 4)} \qquad (3)$$

This method requires back-to-back transient absorption data collection with a triplet reference compound that has a known triplet quantum yield, FT(R). The back-to-back experiments must be performed using sample and reference solutions having the same optical density at the excitation wavelength and pumping with the same power. In this particular case we used 4-thiothymidine as the reference compound, which has a reported triplet yield of 1.0±0.1.[87] It should be noted that our determination of the triplet-triplet extinction coefficient for 4-thiothymidine using the above singlet depletion method is in agreement with that previously reported (2500±700 M$^{-1}$ cm$^{-1}$ at 520 nm), further supporting the use of this method herein. From the back-to-back transient absorption experiments, the intensity of the triplet-triplet absorption of the reference compound, $\Delta A_R(\lambda_3)$, and the unknown, $\Delta A_R(\lambda_4)$, are obtained. These can be taken at different wavelengths ($\lambda_3$ and $\lambda_4$, respectively) for the reference (R) and unknown (U), as long as the wavelengths chosen are well separated from the ground state bleaching signals and the triplet-triplet extinction coefficients are respectively known, $\varepsilon_R*(\lambda_3)$ and $\varepsilon U*(\lambda_4)$. Having all this information, eqn (3) is then used to find the triplet quantum yield of the unknown, $\Phi_T(U)$.

The triplet-triplet extinction coefficient of 2tUra was not determined using the singlet depletion method because the ground state absorption of 2tUra does not extend into the probe wavelength region used in this work. However, the triplet-triplet extinction coefficients and triplet yield of the structurally similar 2-thiothymine have recently been reported. Hence, the triplet yield of 2tUra was estimated from back-to-back experiments with the 2-thiothymine by assuming they have equal triplet-triplet extinction coefficients. This seems to be a good assumption given the comparable shapes and intensities of the triplet-triplet absorption spectra of these two compounds when testing solutions with identical optical densities at the excitation wavelength.

Singlet Oxygen Quantum Yields

Solutions of 4tUra, 2,4dtUra, and the singlet oxygen standard (phenalenone; $\Phi_\Delta$=0.98) were prepared in acetonitrile, each with an absorbance of 0.3 at 355 nm in a 1×1 cm quartz cuvette. The solutions were purged with oxygen for 30 min, followed by the determination of quantum yields from back-to-back measurements of the singlet oxygen phosphorescence intensity at 1270 nm. The $O_2$-saturated solutions were excited at 355 nm (Spectra Physics GCR-150-30: 7 ns pulse width) and the phosphorescence at 1270 nm was detected with a NIR sensitive photomultiplier tube (H10330A-45, Hamamatsu).

Photoreactivity Measurements

Aqueous phosphate-buffered saline solutions, pH 7.4, containing either 4tUra or 2,4dtUra were prepared with and without 5'-AMP and loaded into 1×1 cm septum-top quartz cuvettes. The concentrations of the thiouracil derivatives and 5'-AMP were 24 and 120 mM, respectively. These concentrations were chosen in order to favor the bimolecular photoreaction between the thiouracil derivative and 50-AMP, while simultaneously maintaining the absorbance of the solutions within the linear dynamic range limit of the UV-visible spectrophotometer used. All solutions were purged with ultrapure nitrogen for 30 min and kept under constant nitrogen flow throughout the irradiation period. An optical parametric amplifier (TOPAS, Quantronix/Light Conversion) pumped by our Libra laser system (described above) was used for monochromatic (±1 nm) irradiation of the samples. The irradiation beam diameter was approximately 7 mm at 1/e$^2$ and had a power of 10 mW at the sample position, corresponding to an average intensity of 0.26 Jm$^{-2}$ at the sample. Absorbance changes in the thiouracil solutions, with and without 5'-AMP, were monitored periodically using UV-visible spectroscopy (Cary 100 Bio) during irradiation at 365 nm for up to 90 min and while stored in the dark for up to three and a half days.

Results

Steady-State Absorption Spectra

FIG. 7 shows the molar absorptivity spectra of the thiouracil series investigated in this work and compares them to that of the canonical uracil nucleobase (Ura). Thionation at the C2 position of the uracil chromophore redshifts the absorption maximum by 11 nm and increases the molar absorptivity by 1.4-fold, whereas thionation at the C4 position redshifts the absorption maximum about 70 nm and more than doubles the molar absorptivity. Furthermore, substitution of the oxygen atoms by sulfur atoms in both carbonyl groups of uracil red-shifts the absorption spectrum by more than 100 nm (11 058 cm$^{-1}$) relative to that of the canonical nucleobase, while simultaneously increasing the molar absorptivity of the lowest-energy absorption band by 1.3-fold.

Figure 8A:
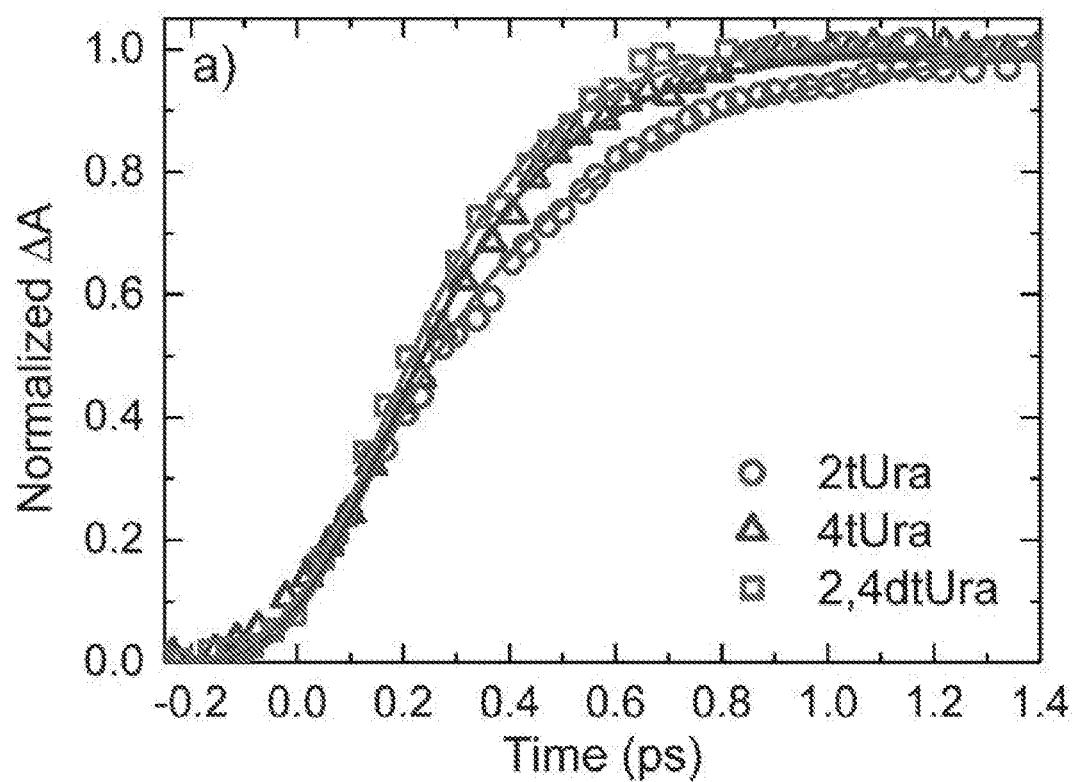
FIGS. 8(A-B) illustrate plots showing growth of triplet-state population (A) and the corresponding triplet-triplet absorption spectrum (B) of 2tUra, 4tUra, and 2,4dtUra in aqueous buffer solution at pH 7.450 following femtosecond UVA excitation at 320, 335, and 350 nm, respectively. Triplet state populations were monitored at 600 nm to avoid overlap from other transient species. Growth traces are normalized and cropped at 1.4 ps to clearly show the relative rates of intersystem crossing. Triplet state extinction coefficients were determined using the singlet depletion method.
Figure 8B:
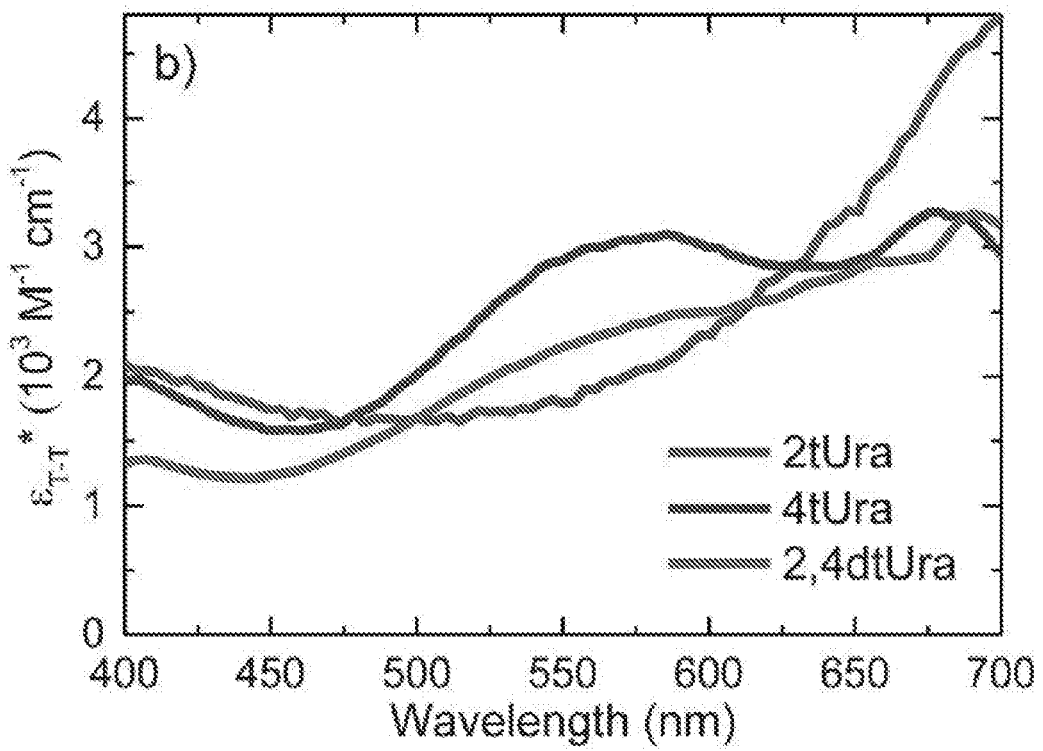

Measurement of Intersystem Crossing Rates, Triplet Yields, and Rates of Triplet-State Decay Femtosecond to microsecond broadband transient absorption spectroscopy was used to measure the rates of intersystem crossing to the triplet manifold, the triplet yields, and the rates of triplet-state decay back to the ground state. The triplet state of the thiouracil derivatives can be selectively probed at wavelengths longer than 600 nm without the interference of other transient absorption species. FIG. 8a shows the triplet growth traces recorded at 600 nm, which were normalized to highlight their relative rates of triplet-state population. The population lifetimes (tISC) obtained from a global analysis of the broadband transient absorption data are presented in Table 2. Thionation at the C4 position results in faster intersystem crossing than thionation at the C2 position. Doubling thionation results in intersystem crossing with a shorter lifetime than that measured for 4tUra. FIG. 8b shows that the triplet-triplet absorption spectrum of each derivative is broad and almost featureless; spanning the entire probe range from 400 to 700 nm.

TABLE 2

Triplet-state properties in aqueous buffer and singlet oxygen yields in O$_2$-saturated acetonitrile measured for 2tUra, 4tUra, and 2,4dtUra and compared to literature values for the uracil nucleobase

|  | $\tau_{ISC}{}^a$ (fs) | $\Phi_T{}^b$ | $\kappa_T{}^c$ (10$^6$ s$^{-1}$) | $\Phi_\Delta{}^d$ |
|---|---|---|---|---|
| Ura | <10 | 0.023 | 2.9 | 0.15 ± 0.02 |
| 2tUra | 360 ± 30 | 0.75 ± 0.20 | — | — |
| 4tUra | 240 ± 20 | 0.90 ± 0.15 | 1.7 ± 0.3 | 0.49 ± 0.02 |
| 2,4dtUra | 220 ± 40 | 0.90 ± 0.15 | 4.3 ± 0.9 | 0.49 ± 0.02 |

$^a$Intersystem crossing lifetime,
$^b$triplet quantum yield, and
$^c$tripletstate decay rate in aqueous phosphate-buffered saline solution, pH 7.4. The thiouracil triplet decay rates were collected in 24 mM solutions.
$^d$Singlet oxygen quantum yield in O$_2$-saturated acetonitrile.

Figure 9:
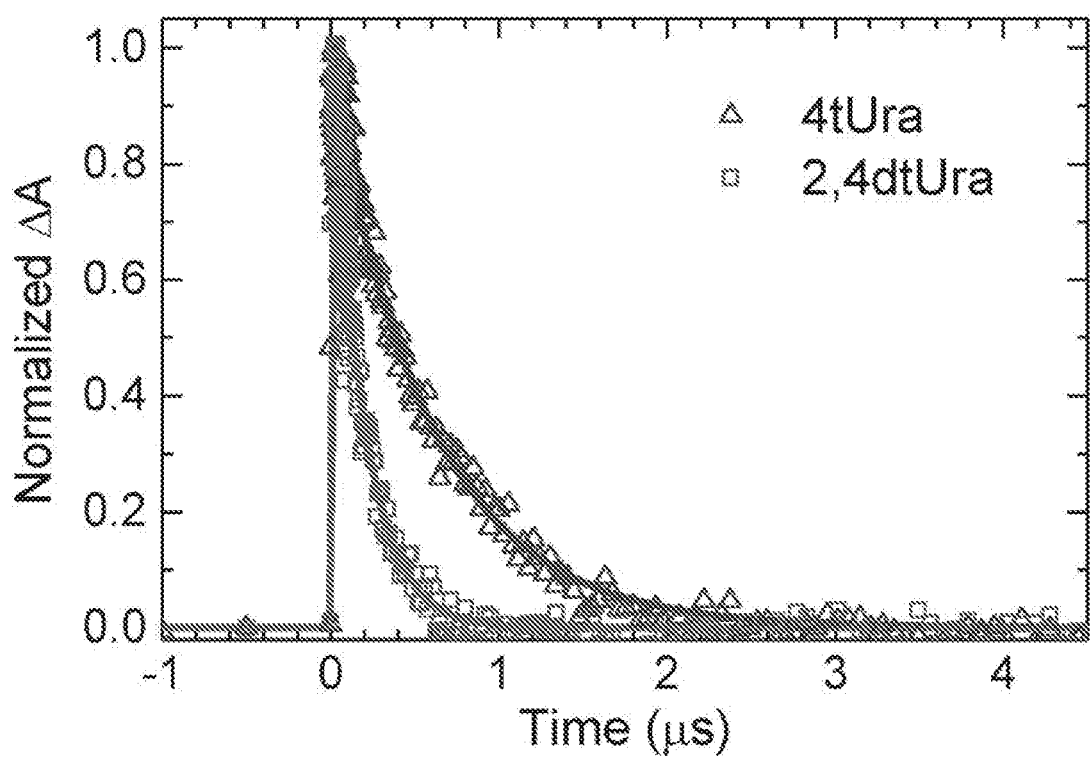
FIG. 9 illustrates a plot showing triplet-state decay traces of 4tUra and 2,4dtUra following 350 nm excitation at concentrations of 24 mM in nitrogen-purged aqueous buffer solutions. Global fitting of several decay traces from the broadband transient spectra produced the fit lines shown and the rates of triplet-state decay (kT) reported in Table 1.

Back-to-back transient absorption measurements of the 2tUra, 4tUra, and 2,4dtUra series were also performed under the same experimental conditions in order to determine their triplet-triplet extinction coefficients ($\varepsilon_{T-T}*$) and triplet quantum yields ($\Phi_T$). Analysis of these measurements indicate that all three thiouracil derivatives populate the triplet state with nearly unity yield (Table 2), FIG. 7 Molar absorptivity spectra of the canonical uracil nucleobase and the thiouracil series studied in aqueous phosphate-buffered saline solution, pH 7.4 in agreement with previous measurements for 4tUra51 and its nucleoside. For 4tUra and 2,4dtUra, the triplet-triplet absorption band decays back to the ground state in hundreds of nanoseconds at thiouracil concentrations of 24 μM in N$_2$-saturated aqueous buffer solutions (FIG. 9 and Table 2). The triplet-state of 4tUra decays on the same time scale as that measured for its nucleoside under similar experimental conditions. The rate of triplet-state decay of 2,4dtUra is reported for the first time in this work, whereas that of 2tUra decays on a similar time scale in N$_2$-saturated acetonitrile solution and was not determined in aqueous solution.

Measurement of Singlet Oxygen Yields

Figure 10:
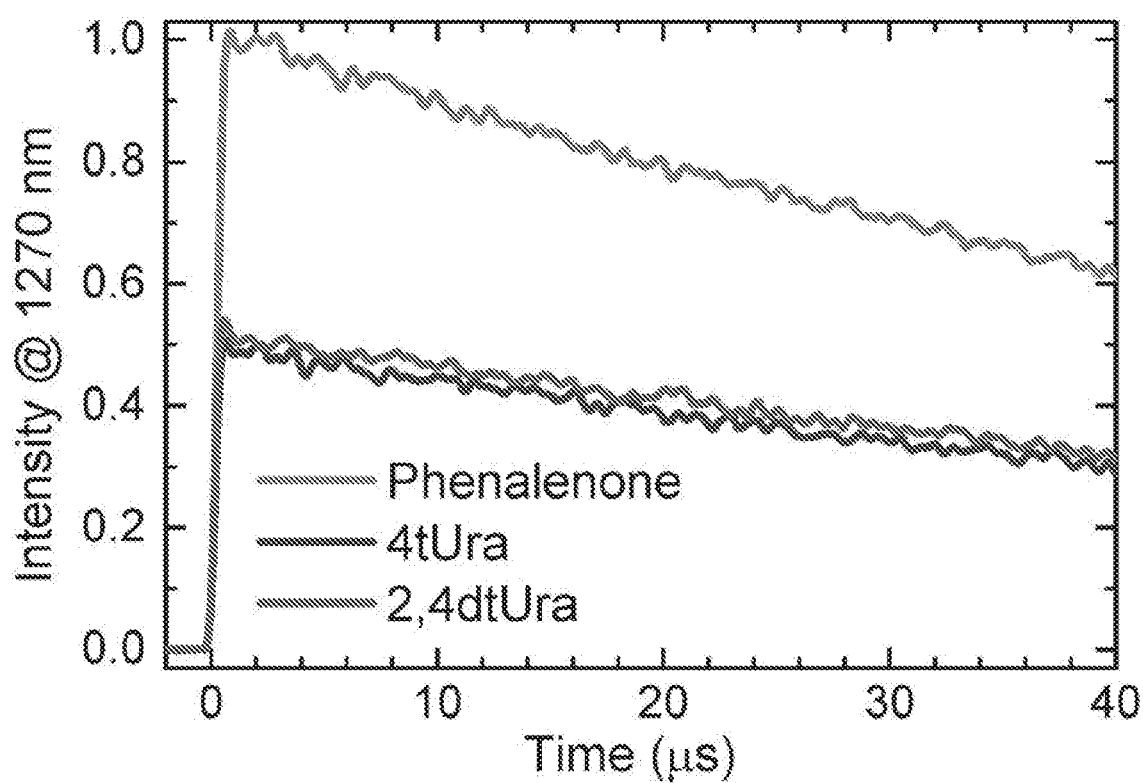
FIG. 10 illustrates a plot showing singlet oxygen generation from 4tUra and 2,4dtUra following nanosecond excitation at 355 nm as monitored by the characteristic phosphorescence of singlet oxygen at 1270 nm in $O_2$-saturated acetonitrile solutions. Quantum yields were determined by comparison with the standard phenalenone ($\Phi_A$=0.98).

The singlet oxygen ($^1$O$_2$) quantum yields of 4tUra and 2,4dtUra were measured by monitoring the characteristic phosphorescence of $^1$O$_2$ at 1270 nm with nanosecond time resolution. To the best of our knowledge, these yields are reported for the first time for both thiobases. As shown in Table 2 and FIG. 10, both derivatives exhibit a $^1$O$_2$ quantum yield of 0.49±0.02 in O$_2$-saturated acetonitrile solutions. The yield measured for 4tUra in this work is in excellent agreement with that determined previously for the 4tUra nucleoside under similar experimental conditions. No attempt was made to measure the $^1$O$_2$ yield of 2tUra because this derivative has limited absorption at 355 nm; the excitation wavelength used for these measurements.

Photoreactivity of 4tUra and 2,4dtUra with Adenosine 5'-Monophosphate

In order to scrutinize the light-induced reactivity of these sensitizers toward biomolecules, aqueous phosphate-buffered saline solutions of either 4tUra or 2,4dtUra were prepared in the presence of the RNA monomer adenosine 5'-monophosphate (5'-AMP) at a 1:5 molar ratio. 5'-AMP is used as a model biomolecule because 5'-AMP is the canonical Watson-Crick base-pairing partner of uracil in RNA. The experimental conditions were chosen in order to facilitate the extraction of relative photoreaction rates from the changes in the steady-state absorption spectra with irradiation time. Specifically, (1) the changes in absorbance of the solutions with irradiation time were monitored during the initial, linear regime of the photoreaction process where the slope of the data can be related directly to the reaction rate; (2) the concentrations of the thiobase and 5'-AMP were selected in such a way as to enhance the rate of the thiobase-5'-AMP bimolecular reaction, while simultaneously minimizing triplet self-quenching and self-reaction pathways in the thiouracil derivatives; 11,54 and (3) the solutions were irradiated with monochromatic UVA-laser light at (365±1) nm and were continuously purged with ultrapure nitrogen gas in order to eliminate quenching of the triplet state of the thiobase by molecular oxygen and to avoid any putative side reactions of 5'-AMP or the thiobase with reactive oxygen species. Finally, we remark that the photoproducts formed between the thiouracil derivatives and 5'-AMP do not absorb significantly at wavelengths longer than 320 nm and, therefore, the progression of the bimolecular thiobase-5'-AMP photoreactions can be monitored selectively by following the decay of the UVA absorption band in each solution (see the ESI† for details).

Figure 11:
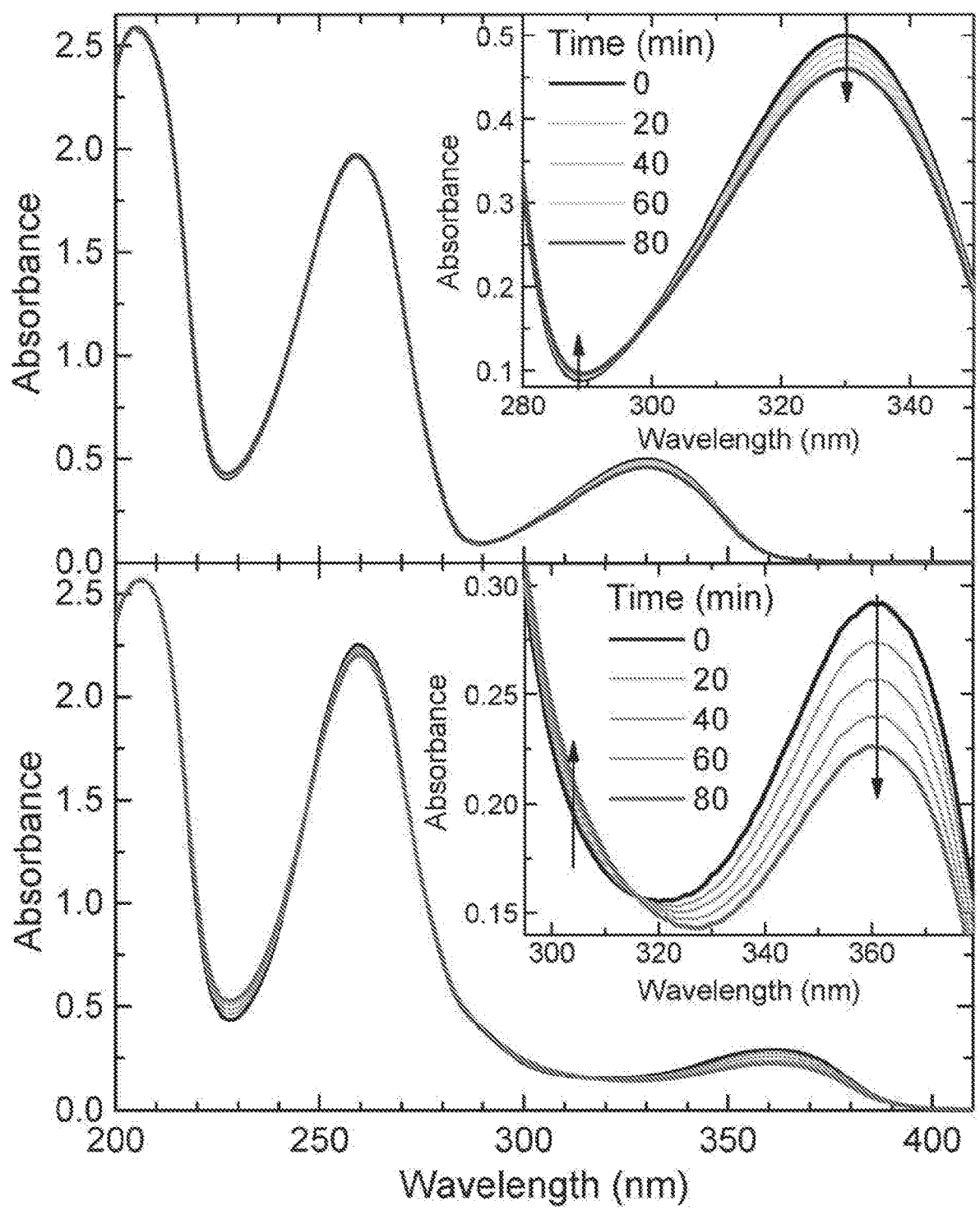
FIG. 11 illustrates plots showing changes in the steady-state absorption spectra used to monitor the reaction of 4tUra (top) or 2,4dtUra (bottom) with 50-AMP upon 365 nm irradiation. Solutions were prepared at 1:5, thiouracil:50-AMP ratios and continuously purged with ultrapure $N_2$. The decrease in absorbance in the UVA region and simultaneous increase in absorbance at shorter wavelengths (highlighted in the inset) provides direct evidence of the oxygen independent photoreaction between the thiouracil and 50-AMP in each solution. The similar spectral changes suggest that the photoreaction mechanism and primary photoproduct are similar in both solutions mixtures.

FIG. 11 shows changes in the absorbance of these solutions upon irradiation at 365 nm, as monitored by steady-state absorption spectroscopy. Both solutions exhibit a linear decrease in their UVA absorption band with a simultaneous increase in their absorbance at wavelengths shorter than B320 nm. Isosbestic points occur at 246, 270, and 300 nm in the spectra of the 4tUra-5'-AMP mixture, whereas they appear slightly red-shifted in the 2,4dtUra-5'-AMP mixture at 246, 275, and 318 nm. The isosbestic points are indicative of the formation of photoproducts. A further spectral analysis described in the ESI† shows that only one major photoproduct is formed in each solution, which is depicted in the difference absorption spectrum (ESI†) for each solution mixture. As discussed in detail in the ESI†, the difference absorption spectra obtained for the 4tUra-5'-AMP and 2,4dtUra-5'-AMP mixtures are both comparable to the absorption spectrum of the major photoproduct formed between the structurally-similar thiobase, 4-thiothymidine, and adenosine.

Figure 12:
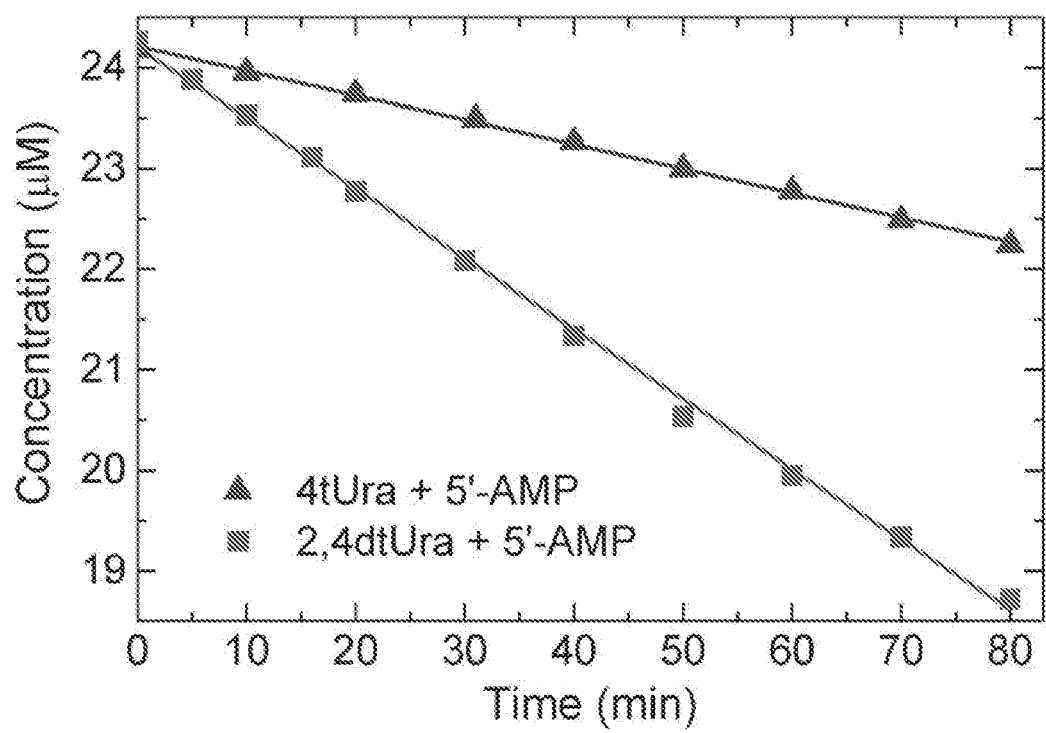
FIG. 12 illustrates a plot showing relative photoreaction rates observed for 4tUra and 2,4dtUra in N2-saturated aqueous buffer solutions containing 50-AMP. Solutions were irradiated with 365 nm laser light and the decrease in thiouracil concentration was monitored by steady-state absorption spectroscopy. The photoreaction rates reported in the text were obtained from the slope of the linear regression.

FIG. 12 shows the change in concentration of 4tUra and 2,4dtUra as a function of irradiation time in solutions containing 5'-AMP. The relative photoreaction rates were estimated from the slopes of linear regression fittings of the data reported in FIG. 16. Significantly, 2,4dtUra exhibits a photoreaction rate of $(1.2±0.2)×10^{-9}$ M s$^{-1}$, approximately three times faster than the photoreaction rate measured for 4tUra, $(0.39±0.04)×10^{-9}$ M s$^{-1}$, under the same experimental conditions. The importance of this threefold increase in the photoreaction rate is highlighted in the discussion section.

Photophysical Characterization of the Thiouracil Series

An important property in the characterization of the photosensitizing potential of the thiouracil series is the determination of their ground-state molar absorptivity spectra. The molar absorptivity spectra shown in FIG. 7 demonstrate that the electronic structure of the canonical uracil nucleobase is greatly perturbed upon thionation and that the extent of the perturbation depends sensitively on the carbon position at which the double-bonded oxygen atom is substituted for a sulfur atom. In comparison to the uracil nucleobase, each of the thionated derivatives displays a redshifted absorption spectrum into the UVA region (315 to 400 nm). The maximum of the lowest-energy absorption band is shifted considerably further to the red (60 nm, 6734 cm$^{-1}$) upon sulfur substitution of the oxygen atom at the C4 position compared to when the substitution is made at the C2 position. Doubling thionation induces the greatest redshift in absorption, with 2,4dtUra exhibiting an absorption tail that extends into the visible region of the spectrum. In fact, based on the molar absorptivity spectra, the absorption efficiency of 2,4dtUra at nearvisible wavelengths (380 to 400 nm) is about 27-fold greater than that of 4tUra (see ESI† for details). The ability of these thiouracil derivatives to absorb longer wavelengths of light than uracil facilitates their selective excitation over the canonical DNA and RNA nucleobases. This photophysical property is essential for their prospective use in in vitro and in vivo photosensitizing applications.

Absorption at longer wavelengths and with larger absorption coefficients than the canonical DNA and RNA bases is an important property of effective photosensitizers. However, a photosensitizer must also populate long-lived, highly-reactive excited states upon the absorption of light in order to be truly effective. A hallmark of an efficient photosensitizer is population of the triplet state in high yield. The data shown in FIG. 8 and Table 2 provide direct evidence that intersystem crossing to the triplet manifold occurs in hundreds of femtoseconds and in nearly unity yield in all three of the thiouracil derivatives. Assignment of the transient absorption growth traces (FIG. 8A) to the population of the triplet state in both 2tUra and 4tUra is supported by the excellent agreement of the absorption spectra associated with these transient species (FIG. 8B) with those previously reported for the triplet states of 2tUra48 and the 4tUra nucleoside. The triplet-triplet absorption spectrum of 2,4dtUra has not been reported previously. However, several experimental observations point toward the assignment of the transient spectrum shown in FIG. 8B to the triplet state absorption of 2,4dtUra. In particular, the slow rate at which this transient species decays to repopulate the ground state (FIG. 9) strongly supports its assignment as the lowest energy triplet state. Furthermore, this transient species is readily quenched by molecular oxygen, producing a $^1O_2$ yield of ca. 50%.

The triplet yield of all three thiouracil derivatives is more than thirtyfold higher than the parent nucleobase uracil (Table 2). The thirtyfold increase in triplet-state population upon thionation of the uracil chromophore originates from the presence of the heavier sulfur atom(s). Thionation increases the density of states and the spin-orbit coupling interaction between the singlet and triplet manifolds, while simultaneously reducing the relevant singlet-triplet energy gaps of the uracil chromophore. Hence, intersystem crossing becomes highly favored over internal conversion back to the ground state.

The nearly unity triplet yields should also increase the photoreactivity of these thiouracil derivatives, and therefore, their efficacy as photosensitizers. One established method for quantifying the reactivity of a sensitizer's triplet state is to determine its ability to generate $^1O_2$. The results shown in FIG. 10 demonstrate that both 4tUra and 2,4dtUra generate $^1O_2$ with ca. 50% yield following UVA excitation. This is 3.3-fold higher than the amount of $^1O_2$ generated by uracil when these nucleobases are directly excited to their lowest-energy absorption band. The increase in the $^1O_2$ yield is also consistent with the more than thirtyfold increase in the triplet yield of 4tUra and 2,4dtUra compared to uracil (Table 2).

Photoreactivity of 2,4dtUra Versus 4tUra with 50-AMP

The generation of 1O2 by a photosensitizer and the subsequent reaction of this highly oxidizing species with biomolecules is an indirect mode of photochemical reaction known as Type II photosensitization. Oxidatively generated damage to cellular components mediated by Type II photosensitization and the formation of other reactive oxygen species can eventually lead to cell death and is a common mode of photodynamic therapy. Above, we have shown that UVA excitation of 2,4dtUra results in ca. 50% $^1O_2$ yield, evidencing the unsurpassed potential of 2,4dtUra in photosensitization applications compared to the other members of the series. This qualification warrants further investigation into the reactivity of 2,4dtUra as a photocrosslinking agent.

Direct photocycloaddition reaction between the excited-state of a sensitizer and a biomolecule is also an important mechanism that is widely used in photocrosslinking structural-biology studies based on 4tUra. Photoaddition reactions can play an equal or greater role than $^1O_2$ generation in phototherapeutic applications, especially in oxygen-deprived environments such as hypoxic solid tumors. Therefore, it is important to evaluate the potential of 2,4dtUra as a photocycloaddition sensitizer for both structural biology and phototherapeutic applications.

To investigate the ability of 2,4dtUra to participate in photocycloaddition reactions with nucleic acid bases, we have measured the photoreactivity of 2,4dtUra with 5'-AMP in N2-saturated aqueous solutions-experimental conditions that prevent $^1O_2$ generation. Similar photoreactivity experiments were performed using 4tUra as the sensitizer in order to determine the relative efficacies of 2,4dtUra and 4tUra in undergoing these reactions. Efficient photocycloaddition between 4-thiouridine and adenosine has been reported, and the mechanism of photoproduct formation between 4-thiothymidine and adenosine has been characterized in-depth. 63 Furthermore, both 4-thiouridine and 4-thiothymidine are structurally-similar to 2,4dtUra and their reaction with adenosine is expected to be similar to that of 2,4dtUra with 5'-AMP. We present evidence in the ESI† that all three of these photocycloaddition reactions are analogous and propose a mechanism for the formation of the primary photoproduct between 2,4dtUra and 5'-AMP.

FIG. 11 shows that irradiation of the 2,4dtUra-5'-AMP and 4tUra-5'-AMP solutions at 365 nm results in a decrease of the UVA absorption band of the thiobase and a corresponding increase in absorption at shorter wavelengths. The spectral changes observed for the 2,4dtUra-5'-AMP mixture closely resemble those of the 4tUra-5'-AMP mixture, suggesting that the photoreaction mechanism between 2,4dtUra and 50-AMP and 4tUra and 5'-AMP are comparable, as articulated above. The photoproduct absorption spectra (ESI†) reinforce the idea that 4tUra and 2,4dtUra undergo a similar photoreaction with 5'-AMP and that it is analogous to the one previously reported between 4-thiothymidine and adenosine (see ESI† for further discussion). More important to the present discussion is the fact that the photoproduct formed in this reaction has negligible absorption in the UVA region where 4tUra and 2,4dtUra absorb, allowing the relative rates of photoreaction to be quantified directly from the steady-state absorption data. The results reveal that the rate of photocycloaddition observed between 2,4dtUra and 5'-AMP is threefold greater than that between 4tUra and 5'-AMP upon irradiation with monochromatic, 365 nm laser light in solutions containing the same concentrations of reactants (FIG. 12). Furthermore, the photoreactivity experiments show that 2,4dtUra (and 4tUra) can react with 50-AMP by an oxygen-independent photocycloaddition mechanism. They also suggest the potential of using dithionated RNA derivatives for near-visible phototherapeutic applications in oxygen-deprived biological environments where Type II photosensitization may not be effective.

Figure 13:
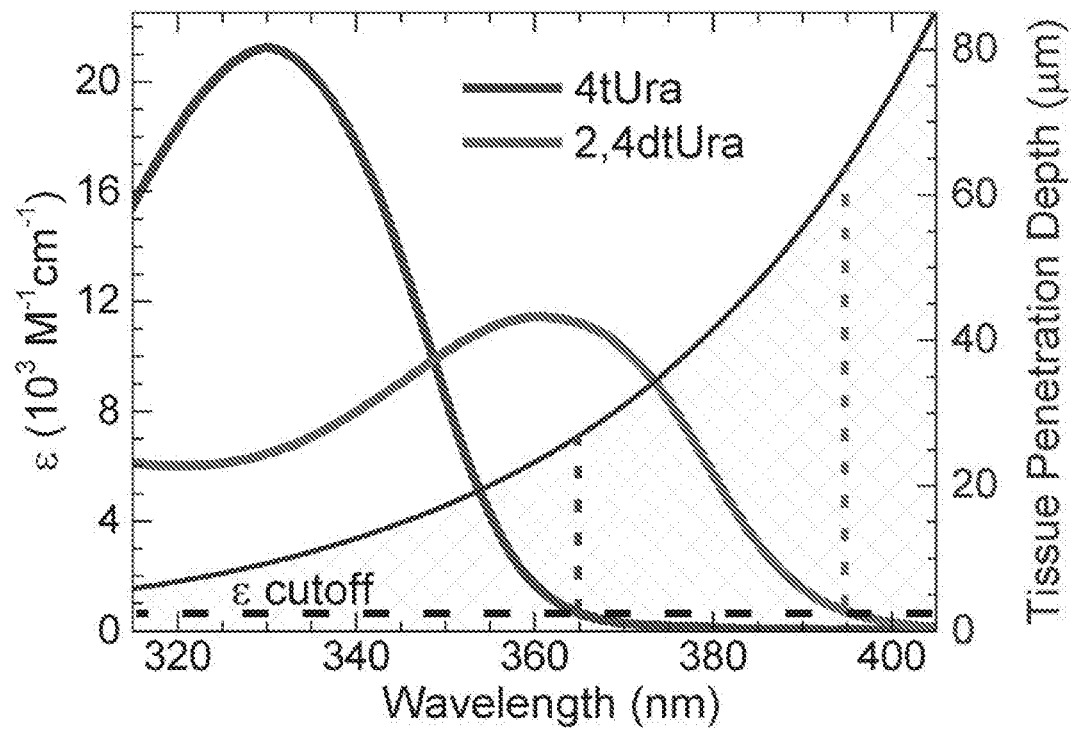
FIG. 13 illustrates a plot showing molar absorptivity spectra of 4tUra and 2,4dtUra overlaid with the function of the wavelength-dependent penetration depth of light into unpigmented tissue. The ε cutoff is defined by the molar absorptivity of 4tUra at 365 nm; the excitation wavelength typically used in its photosensitization applications.

On the Enhancement of Photocrosslinking and Phototherapeutic Applications Using 2,4dtUra as the Sensitizer The photochemical characterization of the thiouracil series presented above shows that 2,4dtUra can outperform 4tUra in its current uses as a photocrosslinking agent and can potentially enable phototherapies based on thio-RNA derivatives. Importantly, many of the current applications employing 4tUra and other UVA photosensitizers (e.g. psoralen derivatives) use radiation at 365 nm as the excitation source. The use of longer UVA wavelengths reduces direct excitation of other biomolecules, thereby increasing photosensitization efficiency and minimizing unwanted side reactions. However, the requirement of using relatively high concentrations of the sensitizer and/or long irradiation times are two major drawbacks in the current use of 4tUra in photocrosslinking studies as well as in PUVA (psoralen+UVA) photochemotherapies. The threefold higher photoreaction rate of 2,4dtUra as compared to 4tUra at 365 nm (FIG. 12) can facilitate the use of lower sensitizer concentrations and/or shorter irradiation times in photocrosslinking and phototherapeutic applications. More importantly, 2,4dtUra enables the use of lower-energy excitation wavelengths, as long as 395 nm (see FIG. 13), considering a molar absorptivity cutoff criterion equal to that currently used for 4tUra (see ESI† for a more thorough justification of this cutoff criterion). In other words, the use of 2,4dtUra enables excitation at 395 nm while maintaining the same absorption efficiency and photoreactivity as that of 4tUra at 365 nm. The ability to use longer irradiation wavelengths afforded by 2,4dtUra should also improve the selective excitation of the sensitizer, while simultaneously enabling photosensitization deeper within the skin and other tissues. This is because irradiation at a wavelength of 365 nm leads to a photosensitization depth of about 27 mm into tissues, whereas radiation at 395 nm can penetrate as deep as 65 mm (FIG. 13). Hence, the replacement of 4tUra by 2,4dtUra in current in vivo photocrosslinking studies is expected to increase the effective photosensitization depth by up to 140%. The greater tissue depths at which 2,4dtUra can be photoactivated, together with its enhanced photosensitization properties, have the potential to move thiouracil derivatives into mainstream phototherapeutic application and could offer a viable substitute for psoralen derivatives in PUVA treatment without the late-stage side effects.

Structure-Photoreactivity Relationships Between the DNA and RNA Thiopyrimidine Families and with Other Pyrimidine Monomers A comparison of the results presented for the thiouracil series with those for the thiothymine series shows that the methyl group at the C5 position of the pyrimidine ring plays a considerable role in modulating the photophysical properties of these thiopyrimidine families. For instance, the ground-state absorption spectra of the thiothymine series are slightly red-shifted (B5 nm) and show a moderate decrease in molar absorptivity as compared to those of the thiouracil series. These observations mirror earlier reports between the canonical uracil and thymine nucleobases. Similarly, the rate of intersystem crossing in the thiothymine series is more sensitive to the degree of thionation than is the intersystem crossing rate in the thiouracil series. That is, the thiothymine series exhibits a 3.5-fold increase in the rate of intersystem crossing in going from 2-thiothymine to 2,4-dithiothymine (2,4dtThy), whereas a 1.6-fold increase is observed in going from 2tUra to 2,4dtUra in this work. The rate of triplet-state decay has also been shown to be modulated by C5-functionalization, being faster in 2tUra than in 2-thiothymine. This is consistent with their relative rates of intersystem crossing and with the slightly different magnitude of singlet-triplet energy gaps between the two families of thiobases. The observation that the intersystem crossing lifetime reported in this work for 2,4dtUra (220±40 fs) is the same as that reported recently for 2,4dtThy (180±40 fs), within the experimental uncertainties, lends strong support to the idea that spin-orbit coupling in these compounds is saturated upon doubling thionation. 11 Another observation is that the magnitude of the $^1O_2$ yields for 2,4dtThy and 4-thiothymidine (4tThd) are 6 and 14% lower, respectively, than those measured for the corresponding thiouracil derivatives. These differences in the triplet-state properties of the thiopyrimidine families are in line with previous works, where the C5-substituent is shown to modulate the photophysical properties of uracil in comparison to thymine and other uracil derivatives.

The results presented herein for the thiothymine series also show that the functional groups at the C2 and C4 positions of the pyrimidine ring play important roles in modulating the photochemical properties of the thiothymine and thiouracil series. The absorption spectra, the rate of intersystem crossing, and the triplet and $^1O_2$ yields are uniquely sensitive to the specific position at which the thymine and uracil nucleobase are thionated. In particular, the structure-photoreactivity relationships observed in the thiopyrimidine families lend further support to the idea that functionalization at the C4 position of the pyrimidine ring, plays a more important role than functionalization at the C2 position in enhancing the photoreactivity of the pyrimidine nucleobases in solution. However, a detailed investigation of the excited-state dynamics of both thiopyrimidine families, as well as of other pyrimidine analogues, is necessary before these structure-photoreactivity relationships can be further generalized.

Finally, an important distinction between the thiouracil and the thiothymine families is their specific role in biochemistry; particularly, the targeted incorporation of thiouracil derivatives into cellular RNAs rather than DNA. This biological distinction enables an alternative, broader range of intracellular sites for photochemical and photocrosslinking reactions, which has facilitated the continued use of 4tUra as an informative photocrosslinking probe in RNA structural-biology studies over the past five decades. It is surprising, however, that while thio-DNA derivatives have been shown to be effective sensitizers in the photodynamic treatment of various cancers, the use of thio-RNA derivatives in phototherapeutic applications have received considerably less scrutiny. Thio-RNA derivatives are not limited to interactions with DNA and proteins within the nucleus, but can also interact with proteins and other RNAs throughout the cell. Furthermore, highly-targeted therapeutics based on short, interfering RNA sequences (siRNAs) and on RNA aptamers that bind to intra- and extra-cellular proteins are rapidly emerging. These therapies can readily incorporate 2,4dtUra to promote irreversible binding of their cellular targets through photocros slinking reactions. Indeed, RNA aptamers containing 4tUra are able to target and photocrosslink with extracellular marker proteins in live breast cancer cell cultures. The results presented herein suggest that 2,4dtUra could be even more effective in these types of applications. Furthermore, the increased targeting ability and higher $^1O_2$ yield of 2,4dtUra, as compared to 4tThd and 2,4dtThy, suggest that this sensitizer could have greater photodynamic activity than these thio-DNA sensitizers, or could be used as a complementary photosensitizer to target DNA and RNA simultaneously.

From the above description of the invention, those skilled in the art will perceive improvements, changes and modifications. Such improvements, changes and modifications within the skill of the art are intended to be covered by the appended claims. All references, publications, and patents cited in the present application are herein incorporated by reference in their entirety.

Having described the invention, we claim:

1. A method of using a compound in a phototherapy procedure, the method comprising:
   administering to a subject in need of treatment a therapeutically effective amount of compound having the formula:

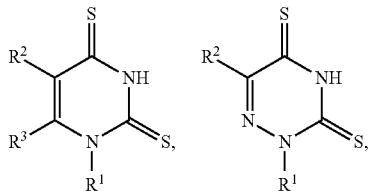

or pharmaceutically acceptable salts thereof;
   wherein $R^1$ is H, OH, ribose, deoxyribose, amino acid residue(s), fatty acid residue(s), $OR_a$, where $R_a$ comprises at least one of a straight chain, branched or cyclic alkyl, CO-alkyl, CO-aryl, CO-alkoxyalkyl, arylsulfonyl, or aralkylsulfonyl, or a mono, di, or triphosphate thereof,
   $R^2$ and $R^3$ are independently the same or different and are each selected from the group consisting of a H, F, Cl, Br, I, a lower alkyl group, $(CH_2)_{n1}OR'$ (wherein n1=1, 2, or 3), $CF_3$, $CH_2$—$CH_2X$, O—$CH_2$—$CH_2X$, $CH_2$—$CH_2$—$CH_2X$, O—$CH_2$—$CH_2X$ (wherein X=F, Cl, Br, or I), CN, (C=O)—R', $N(R')_2$, $NO_2$, (C=O)$N(R')_2$, O(CO)R', OR', SR', COOR' (wherein R' is H or a lower alkyl group), or a substituted or unsubstituted aryl, heteroaryl, cycloalkyl, or heterocyclyl, and wherein $R^2$ and $R^3$ if present may be linked to form a cyclic or polycyclic ring, wherein the ring is a substituted or unsubstituted aryl, heteroaryl, cycloalkyl, or heterocyclyl; and
   exposing the administered compound to electromagnetic radiation.

2. The method of claim 1 wherein the compound absorbs electromagnetic radiation having wavelengths from about 300 nm to about 1400 nm.

3. The method of claim 1, wherein the compound is exposed to ultraviolet radiation to cause localized cell death or injury.

4. The method of claim 1, wherein the compound is selected from the group consisting of:

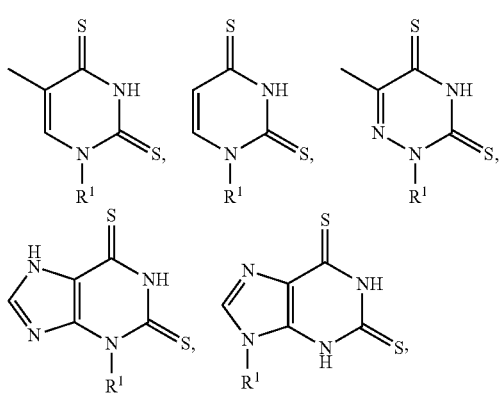

and pharmaceutically acceptable salts thereof, wherein $R^1$ is H, OH, ribose, deoxyribose, amino acid residue(s), fatty acid residue(s), $OR_a$, where $R_a$ comprises at least one of a straight chain, branched or cylclic alkyl, CO-alkyl, CO-aryl, CO-alkoxyalkyl, arylsulfonyl, or aralkylsulfonyl, or a mono, di, or triphosphate thereof.

5. The method of claim 1, wherein exposing the administered compound to electromagnetic radiation generates a therapeutically effective amount of reactive intermediates causing localized cell death or injury.

6. The method of claim 1, wherein the procedure comprises contacting a target tissue of the subject with the administered compound.

7. The method of claim 6, wherein the target tissue is a colon, prostate, gastric, esophageal, uterine, endometrial, pancreatic, breast, cervical, brain, skin, gallbladder, lung, throat, kidney, testicular, prostrate, gastric, or ovary tissue.

8. The method of claim 6, wherein the target tissue is cancerous tissue.

9. The method of claim 6, wherein the target tissue is a tumor.

10. The method of claim 1, for use in treatment of cancer or a cancer-associated disorder, wherein the cancer or cancer-associated disorder is colon cancer, prostate cancer, gastric cancer, esophageal cancer, uterine cancer, endometrial cancer, pancreatic cancer, breast cancer, cervical cancer, brain cancer, skin cancer, gall bladder cancer, lung cancer, or ovarian cancer.

11. The method of claim 1, for use in treatment of an inflammation-associated disorder.

12. A method of treating cancer or a cancer-associated disorder in a subject in need thereof, the method comprising:
    administering to a subject in need of treatment a therapeutically effective amount of compound having the formula:

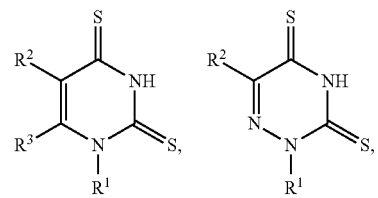

or pharmaceutically acceptable salts thereof;
    wherein $R^1$ is H, OH, ribose, deoxyribose, amino acid residue(s), fatty acid residue(s), $OR_a$, where $R_a$ comprises at least one of a straight chain, branched or cyclic alkyl, CO-alkyl, CO-aryl, CO-alkoxyalkyl, arylsulfonyl, or aralkylsulfonyl, or a mono, di, or triphosphate thereof,
    $R^2$ and $R^3$ are independently the same or different and are each selected from the group consisting of a H, F, Cl, Br, I, a lower alkyl group, $(CH_2)_{n1}OR'$ (wherein n1=1, 2, or 3), $CF_3$, $CH_2$—$CH_2X$, O—$CH_2$—$CH_2X$, $CH_2$—$CH_2$—$CH_2X$, O—$CH_2$—$CH_2X$ (wherein X=F, Cl, Br, or I), CN, (C=O)—R', $N(R')_2$, NO2, (C=O)$N(R')_2$, O(CO)R', OR', SR', COOR' (wherein R' is H or a lower alkyl group), or a substituted or unsubstituted aryl, heteroaryl, cycloalkyl, or heterocyclyl, and wherein $R^2$ and $R^3$ if present may be linked to form a cyclic or polycyclic ring, wherein the ring is a substituted or unsubstituted aryl, heteroaryl, cycloalkyl, or a heterocyclyl; and exposing the administered compound to electromagnetic radiation effective to treat the cancer or cancer-associated disorder.

13. The method of claim 12 wherein the compound absorbs electromagnetic radiation having wavelengths from about 300 nm to about 1400 nm.

14. The method of claim 12, wherein the compound is exposed to ultraviolet radiation to cause localized cell death or injury.

15. The method of claim 12, wherein the compound is selected from the group consisting of:

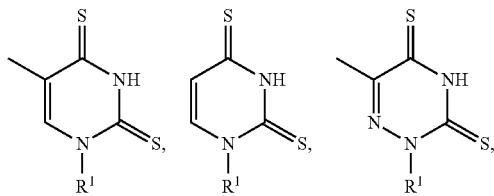

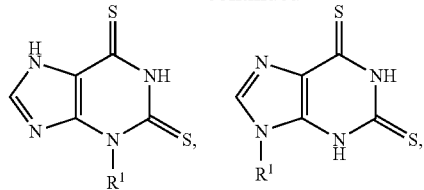

and pharmaceutically acceptable salts thereof;

wherein $R^1$ is H, OH, ribose, deoxyribose, amino acid residue(s), fatty acid residue(s), $OR_a$, where $R_a$ comprises at least one of a straight chain, branched or cylclic alkyl, CO-alkyl, CO-aryl, CO-alkoxyalkyl, arylsulfonyl, or aralkylsulfonyl, or a mono, di, or triphosphate thereof.

16. The method of claim 12, wherein exposing the administered compound to electromagnetic radiation generates a therapeutically effective amount of reactive intermediates causing localized cell death or injury.

17. The method of claim 12, for use in treatment of cancer or a cancer-associated disorder, wherein the cancer or cancer-associated disorder is colon cancer, prostate cancer, gastric cancer, esophageal cancer, uterine cancer, endometrial cancer, pancreatic cancer, breast cancer, cervical cancer, brain cancer, skin cancer, gall bladder cancer, lung cancer, or ovarian cancer.

* * * * *